United States Patent
Furcht et al.

(10) Patent No.: US 7,838,289 B2
(45) Date of Patent: Nov. 23, 2010

(54) ASSAY UTILIZING MULTIPOTENT ADULT STEM CELLS

(75) Inventors: Leo T. Furcht, Minneapolis, MN (US); Catherine M. Verfaillie, St. Paul, MN (US); Morayma Reyes, Minneapolis, MN (US)

(73) Assignees: ABT Holding Company, Cleveland, OH (US); Regents of the University of Minnesota, St. Paul, MN (US)

(*) Notice: Subject to any disclaimer, the term of this patent is extended or adjusted under 35 U.S.C. 154(b) by 1308 days.

(21) Appl. No.: 10/467,963

(22) PCT Filed: Feb. 14, 2002

(86) PCT No.: PCT/US02/04652

§ 371 (c)(1),
(2), (4) Date: Jan. 5, 2004

(87) PCT Pub. No.: WO02/064748

PCT Pub. Date: Aug. 22, 2002

(65) Prior Publication Data

US 2004/0107453 A1    Jun. 3, 2004

Related U.S. Application Data

(60) Provisional application No. 60/343,386, filed on Oct. 25, 2001, provisional application No. 60/310,625, filed on Aug. 7, 2001, provisional application No. 60/269,062, filed on Feb. 15, 2001, provisional application No. 60/268,786, filed on Feb. 14, 2001.

(51) Int. Cl.
    *C12N 5/00* (2006.01)
(52) U.S. Cl. .................. 435/372; 435/325; 435/366
(58) Field of Classification Search ............... None
    See application file for complete search history.

(56) References Cited

U.S. PATENT DOCUMENTS

| | | |
|---|---|---|
| 4,714,680 A | 12/1987 | Civin |
| 4,965,204 A | 10/1990 | Civin |
| 5,035,994 A | 7/1991 | Civin |
| 5,061,620 A | 10/1991 | Tsukamoto et al. |
| 5,087,570 A * | 2/1992 | Weissman et al. ........ 424/93.7 |
| 5,130,144 A | 7/1992 | Civin |
| 5,197,985 A * | 3/1993 | Caplan et al. ............ 128/898 |
| 5,486,359 A * | 1/1996 | Caplan et al. ............ 424/93.7 |
| 5,589,376 A | 12/1996 | Anderson et al. |
| 5,602,301 A | 2/1997 | Field |
| 5,635,386 A | 6/1997 | Armstrong et al. |
| 5,648,248 A | 7/1997 | Zenke et al. |
| 5,654,183 A | 8/1997 | Anderson et al. |
| 5,672,499 A | 9/1997 | Anderson et al. |
| 5,733,727 A | 3/1998 | Field |
| 5,736,396 A * | 4/1998 | Bruder et al. ............ 435/366 |
| 5,827,735 A | 10/1998 | Young et al. |
| 5,843,780 A | 12/1998 | Thomson |
| 5,906,934 A | 5/1999 | Grande et al. |
| 5,928,943 A | 7/1999 | Franz et al. |
| 6,015,671 A | 1/2000 | Field |
| 6,090,622 A | 7/2000 | Gearhart et al. |
| 6,090,625 A | 7/2000 | Abuljadayel |
| 6,146,888 A | 11/2000 | Smith et al. |
| 6,200,806 B1 | 3/2001 | Thomson |
| 6,214,369 B1 | 4/2001 | Grande et al. |
| 6,271,436 B1 | 8/2001 | Piedrahita et al. |
| 6,280,718 B1 | 8/2001 | Kaufman et al. |
| 6,306,575 B1 | 10/2001 | Thomas et al. |
| 6,361,997 B1 | 3/2002 | Huss |
| 6,653,134 B2 | 11/2003 | Prockop et al. |
| 6,777,231 B1 | 8/2004 | Katz et al. |
| 7,015,037 B1 | 3/2006 | Furcht et al. |
| 7,056,738 B2 | 6/2006 | Prockop et al. |
| 7,229,827 B2 | 6/2007 | Kim et al. |
| 2001/0005591 A1 | 6/2001 | Qasba et al. |
| 2001/0012513 A1 | 8/2001 | Robl et al. |
| 2001/0024824 A1 | 9/2001 | Moss et al. |
| 2001/0024825 A1 | 9/2001 | Thomson |
| 2001/0033834 A1 | 10/2001 | Wilkison et al. |
| 2001/0046489 A1 | 11/2001 | Habener et al. |
| 2002/0061587 A1 | 5/2002 | Anversa |

(Continued)

FOREIGN PATENT DOCUMENTS

CA    2191655 A    6/1997

(Continued)

OTHER PUBLICATIONS

Eglitis, M. A., et al., "Hematopoietic cells differentiate into both microglia and macroglia in the brains of adult mice", Proceedings of the National Academy of Science, Apr. 15, 1997, vol. 94, Issue 8, pp. 4080-4085.

(Continued)

*Primary Examiner*—L Blaine Lankford
(74) *Attorney, Agent, or Firm*—Tarolli, Sundheim, Covell & Tummino L.L.P

(57) ABSTRACT

The present invention relates generally to mammalian multipotent adult stem cells (MASC), and more specifically to methods for obtaining, maintaining and differentiating MASC to cells of multiple tissue types. Uses of MASC in the therapeutic treatment of disease are also provided.

7 Claims, 11 Drawing Sheets

U.S. PATENT DOCUMENTS

| | | |
|---|---|---|
| 2002/0123141 A1 | 9/2002 | Hariri |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2003/0180269 A1 | 9/2003 | Hariri |
| 2004/0107453 A1 | 6/2004 | Furcht et al. |
| 2004/0235165 A1 | 11/2004 | Prockop et al. |
| 2005/0169896 A1 | 8/2005 | Li et al. |
| 2005/0181502 A1 | 8/2005 | Furcht et al. |
| 2005/0283844 A1 | 12/2005 | Furcht et al. |
| 2006/0008450 A1 | 1/2006 | Verfaillie et al. |
| 2006/0030041 A1 | 2/2006 | Furcht et al. |
| 2006/0177925 A1 | 8/2006 | Rosenberg et al. |
| 2006/0228798 A1 | 10/2006 | Verfaillie et al. |
| 2006/0263337 A1 | 11/2006 | Maziarz et al. |
| 2007/0009500 A1 | 1/2007 | Blazar et al. |
| 2007/0059823 A1 | 3/2007 | Verfaillie et al. |
| 2007/0128171 A1 | 6/2007 | Tranquillo et al. |

FOREIGN PATENT DOCUMENTS

| | | |
|---|---|---|
| EP | 0627487 A | 12/1994 |
| WO | WO 95/03062 | 2/1995 |
| WO | WO 95/10599 | 4/1995 |
| WO | WO 95/14079 | 5/1995 |
| WO | WO 96/16163 | 5/1996 |
| WO | WO 96/28539 | 9/1996 |
| WO | WO 99/11758 A | 3/1999 |
| WO | WO 99/15629 | 4/1999 |
| WO | WO 99//16863 | 4/1999 |
| WO | WO 99/27076 A | 6/1999 |
| WO | WO 99/35243 A | 7/1999 |
| WO | WO 99/53021 | 10/1999 |
| WO | WO 00/12682 | 3/2000 |
| WO | WO 00/32140 | 6/2000 |
| WO | WO 01/04268 | 1/2001 |
| WO | WO 01/05944 | 1/2001 |
| WO | WO 01/08691 | 2/2001 |
| WO | WO 01/21766 | 3/2001 |
| WO | WO 01/21767 | 3/2001 |
| WO | WO 01/23528 | 4/2001 |
| WO | WO 01/29206 | 4/2001 |
| WO | WO 01/34776 | 5/2001 |
| WO | WO 01/39784 | 6/2001 |
| WO | WO 01/51610 | 7/2001 |
| WO | WO 01/53461 | 7/2001 |
| WO | WO 01/62899 | 8/2001 |
| WO | WO 01/62901 | 8/2001 |
| WO | WO 01/66697 | 9/2001 |
| WO | WO 01/68815 | 9/2001 |
| WO | WO 02/08388 | 1/2002 |
| WO | WO 01/11011 A2 | 2/2002 |
| WO | WO 01/11011 A3 | 2/2002 |
| WO | WO 02/34890 | 5/2002 |

OTHER PUBLICATIONS

Kopen, G.C., et al., "Marrow stromal cells migrate throughout forebrain and cerebellum, and they differentiate into astrocytes after injection into neonatal mouse brains", Proceedings of the National Academy of Science, Sep. 14, 1999, vol. 96, Issue 19, pp. 10711-10716.

Lagasse, E., et al., "Purified hematopoietic stem cells can differentiate into hepatocytes in vivo", Nature Medicine, Nov. 2000, vol. 6, Issue 11, pp. 1229-1234.

Wang, X., et al., "Cell fusion is the principal source of bone-marrow-derived hepatocytes", Nature, Apr. 24, 2003, vol. 422, Issue 6934, pp. 897-901.

Aldous et al., "Flawed stem cell data withdrawn" New Scientist; (Feb. 15, 2007).

Aldous et al., "Fresh questions on stem cell findings" New Scientist; (Mar. 24, 2007).

Check "Stem cell paper corrected" Nature; 447:763 (2007) and Jiang et al., "Pluripotency of mesenchymal stem cells derived from adult bone marrow" Erratum in Nature: 447:879-880 (2007).

Chi, "Adult stem cell figure retracted" The Scientist; (Jun. 13, 2007).

Glenn, "Paper on versatility of adult stem cells comes under question" The Chronicle; (Feb. 26, 2007).

Holden, "Stem Cells. Controversial marrow cells coming into their own?" Science; 315:760-761 (2007).

Jiang et al., "Multipotent progenitor cells can be isolated from postnatal murine bone marrow, muscle, and brain" Exp. Hematol.; 30:896-904 (2002).

Jiang et al., "Pluripotency of mesenchymal stem cells derived from adult marrow" Nature; 418:41-49 (2002).

Lerner et al., "Stem cell study was flawed, U panel finds" Star Tribune; (Feb. 27, 2007).

Noonan, "Limitations on the usefulness of adult stem cells" Patent Docs (Feb. 28, 2007).

Pincock, "Adult stem cell report questioned" The Scientist (Feb. 26, 2007).

Reyes et al., "Purification and ex vivo expansion of postnatal human marrow mesodermal progenitor cells" Blood; 98:2615-25 (2001).

Serafini et al., "Hematopoietic reconstitution by multipotent adult progenitor cells: precursors to long-term hematopoietic stem cell" J. Exp. Med.; 204:129-139 (2007).

Jiang et al., "Pluripotency of mesenchymal stem cells derived from adult marrow, Supplemental Information for Verfaillie Corrigendum" Nature; 418:41-49 (2002).

Verfaillie, "Letter to the Editor" Experimental Hematology; (2007).

U.S. Patent and Trademark Office, Office Action dated Apr. 3, 2007, in related U.S. Appl. No. 11/238,234.

Erices, Alejandro et al., "Mesenchymal Progenitor Cells in Human Umbilical Cord Blood", British Journal of Haematology, Oxford, GB, vol. 109, No. 1, Apr. 2000, pp. 235-242.

Abstract No. 3897; Alfonso, Zeni et al., "Osteoblast Precursor Cells are Found in the Low-density Fraction of Umbilical Cord Blood", Blood, W.B. Saunders Compagny, Orlando, Florida; vol. 94, No. 10, Suppl. 1 Part 2, Nov. 15, 1999, p. 161B.

Goodwin, H.S., "Multilineage Differentiation Activity by Cells Isolated from Umbilical Cord Blood: Expression of Bone, Fat and Neural Markers", Biology of Blood and Marrow Transplantation, Kluge Carden Jennings Publishing, Charlottesville, Virginia; vol. 7, No. 11; 2001, pp. 581-588.

Abstract No. 769; Yalin Wang et al., "Enhanced Recovery of Hematopoietic Progenitor and Stem Cells from Cultivated Postpartum Human Placenta", Blood, W.B. Saunders Compagny, Orlando, Florida; vol. 11, Part 1, No. 98; Nov. 16, 2001, p. 183A.

Abstract No. 2300; Peter Wernet et al., "Detection of Unrestricted Multipotential Stem Cells in Human Cord Blood", Blood, W.B. Saunders Compagny, Orlando, Florida; vol. 98, No. 11, Part 1, Nov. 16, 2001, p. 550a.

Verfaillie, Catherine; "Adult Stem Cells: Assessing the Case for Pluripotency", Trends in Cell Biology; vol. 12, No. 11, Nov. 11, 2002, pp. 502-508.

Goodwin, H.S. et al. "Multilineage Differentiation Activity by Cells Isolated from Umbilical Cord Blood: Expression of Bone, Fat and Neural Markers", Biology of Blood and Marrow Transplantation, Kluge Carden Jennings Publishing, Charlottesville, Virginia; vol. 7, No. 11; 2001, pp. 581-588.

Verfaillie, Catherine, "Adult Stem Cells: Assessing the Case for Pluripotency", Trends in Cell Biology; vol. 12, No. 11, Nov. 11, 2002, pp. 502-508.

Huilin, Q. et al., "Identification of Genes Responsible for Bone Differentiation from Human Bone Marrow Derived Multipotent Adult Stem Cells" (MASC), Blood, Nov. 16, 2000, vol. 96, No. 11, Part 1, pp. 70a-71a, Abs. 298.

Reyes, M. et al., "Characterization of Multipotent Adult Progenitor Cells, a Subpopulation of Mesenchymal Stem Cells", Annals of the New York Academy of Sciences, 2001, vol. 938, pp. 231-235.

Kuznetsov, S.A. et al. "Factors Required for Bone Marrow Stromal Fibroblast Colony Formation In Vitro", British Journal of Hematology, Jun. 1997, vol. 97, Issue 3, pp. 561-570.

Keene, C.D. et al., "Phenotypic Expression of Transplanted Human Bone Marrow-Derived Multipotent Adult Stem Cells into the Rat CNS", Experimental Neurology, Aug. 2000, vol. 164, No. 2, p. 465, col. 2.

Marmur, R. et al., "Isolation and Developmental Characterization of Cerebral Cortical Multipotent Progenitors", Developmental Biology, 1998, vol. 204, No. 2, pp. 577-591.

Geiger, H. et al., "Globin Gene Expression is Reprogrammed in Chimeras Generated by Injecting Adult Hematopoietic Stem Cells into Mouse Blastocysts", Cell, Jun. 12, 1998, vol. 93, issue 6, pp. 1055-1065.

Grigoriadou, K. et al., "MHC Class Ia Gene Therapy in Organ Transplantation: Prevention of Antibody-Mediated Hyperacute Heart Allograft Rejection in Highly Sensitized Rat Recipients", Human Gene Therapy, 2000, vol. 11, issue 3, pp. 3683-3690.

Geissler, E.K. et al., "Effective Use of Donor MHC Class I Gene Therapy in Organ Transplantation: Prevention of Antibody-Mediated Hyperacute Heart Allograft Rejection in Highly Sensitized Rat Recipients", Human Gene Therapy, 2000, vol. 11, issue 3, pp. 459-469.

Cargill, M. et al., "Characterization of Single-Nucleotide Polymorphisms in Coding Regions of Genes", Nature Genetics, Jul. 1999, vol. 22, pp. 231-238.

Gulcher, J. et al., "Population Genetics: Laying the Groundwork for Genetic Disease Modeling and Targeting", Clinical Chemicak Laboratory Medicine, 1998, vol. 36, No. 8, pp. 523-527.

U.S. Appl. No. 10/945,528, filed Sep. 20, 2004, Catherine M. Verfaillie et al.

Cambrex specimens, "Poietics™ Human Mesenchymal Stem Cell Systems", Cambrex BioScience Walkersville, Inc. 2005.

Yaffe et al., "Serial passaging and differentiation of myogenic cells isolated from dystrophic mouse muscle," Nature, vol. 270, Dec. 29, 1977, pp. 725-727.

Jiao, Shoushu et al., "Long-term correction of rat model of Parkinson's disease by gene therapy," Nature, vol. 362, Apr. 1, 1993, pp. 450-453.

McLaren, "Ethical and social considerations of stem cell research," Nature, vol. 414, Nov. 1, 2001, pp. 129-131.

Bianco et al., "Stem cells in tissue engineering," Nature, vol. 414, Nov. 1, 2001, pp. 118-121.

Temple, Sally, "The development of neural stem cells," Nature, vol. 414, Nov. 1, 2001, pp. 112-117.

Reya et al., "Stem cells, cancer, and cancer stem cells," Nature, vol. 414, Nov. 1, 2001, pp. 105-111.

Lovell-Badge, Robin, "The future for stem cell research," Nature, vol. 414, Nov. 1, 2001, pp. 88-91.

Donovan et al., "The end of the beginning for pluripotent stem cells," Nature, vol. 414, Nov. 1, 2001, pp. 92-97.

Spradling et al., "Stem cells find their niche," Nature, vol. 414, Nov. 1, 2001, pp. 98-104.

Hamilton, David, P., "the Tissue Bank's Shaky Underpinnings," Science, vol. 257, Aug. 14, 1992, p. 869.

Soonpaa et al., "Formation of Nascent Intercalated Disks Between Grafted Fetal Cardiomyocytes and Host Myocardium," Science, vol. 264, Apr. 1, 1994, pp. 98-101.

Prockop, Darwin, "Marrow Stromal Cells as Stem Cells for Nonhematopoietic Tissues," Science, vol. 276, Apr. 4, 1997, pp. 71-74.

Thomson et al., "Embryonic Stem Cell Lines Derived from Human Blastocysts," Science, vol. 282, Nov. 6, 1998, pp. 1145-1147.

Bjornson et al., "Turning Brain into Blood: A Hematopoietic Fate Adopted by Adult Neural Stem Cells in Vivo," Science, vol. 283, Jan. 22, 1999, pp. 534-537.

Brustle et al., "Embryonic Stem Cell-Derived Glial Precursors: A Source of Myelinating Transplants," Science, vol. 285, Jul. 30, 1999, pp. 754-756.

Terstappen et al., "Sequential Generations of Hematopoietic Colonies Derived from Single Nonlineage-Committed CD34$^+$CD38$^-$ Progenitor Cells," Blood, vol. 77, No. 6, Mar. 15, 1991, pp. 1218-1227.

Yin et al., "AC133, a Novel Marker for Human Hematopoietic Stem and Progenitor Cells," Blood, vol. 90, No. 12, Dec. 15, 1997, pp. 5002-5012.

Reyes et al., "Purification and ex vivo expansion of postnatal human marrow mesodermal progenitor cells," Blood, vol. 98, No. 9, Nov. 1, 2001, pp. 2615-2625.

Handyside et al., "Towards the Isolation of embryonal stem cell lines from the sheep," Roux's Archives of Developmental Biology, (1987) 196:185-190.

Handyside et al., "Use of BRL-conditioned medium in combination with feeder layers to isolate a diploid embryonal stem cell line," Roux's Archives of Developmental Biology, (1989) 198:48-56.

Saito et al., "Bovine embryonic stem cell-like cell lines cultured over several passages," Roux's Archives of Developmental Biology, (1992) 201:134-141.

Iannaccone et al., "Pluripotent Embryonic Stem Cells from the Rat are Capable of producing Chimeras," Developmental Biology 163, 288-292 (1994).

Amit et al., "Clonally Derived Human Embryonic Stem Cell Lines Maintain Pluripotency and Proliferative Potential for Prolonged Periods of Culture," Developmental Biology 227, 271-278 (2000).

Rubin et al., "Satellite Cells in Isolated Adult Muscle Fibers in Tissue Culture," *Muscle Regeneration*, edited by A. Mauro et al., Raven Press, New York, 1979, pp. 281-284.

Bruni, Carlo, "Mitotic Activity of Muscle Satellite Cells During the Early Stages of Rhabdomyosarcomas Induction with Nickel Subsulfide," *Muscle Regeneration*, edited by A. Mauro et al., Raven Press, New York, 1979, pp. 265-273.

Talbot et al., "Alkaline Phosphatase Staining of Pig and Sheep Epiblast Cells in Culture," Molecular Reproduction and Development 36:139-147 (1993).

Graves et al., "Derivation and Characterization of Putative Pluripotential Embryonic Stem Cells from Preimplantation Rabbit Embryos," Molecular Reproduction and Development 36:424-433 (1993).

Van Stekelenburg-Hamers et al., "Isolation and Characterization of Permanent Cell Lines from Inner Cell Mass Cells of Bovine Blastocysts," Molecular Reproduction and Development 40:444-454 (1995).

Kelly et al., "DNA Microarray Analyses of Genes Regulated During the Differentiation of Embryonic Stem Cells," Molecular Reproduction and Development 56:113-123 (2000).

Notarianni et al., "Maintenance and differentiation in culture of pluripotential embryonic cell lines from pig blastocysts," J. Reprod. Fert., Suppl. 41 (1990), pp. 51-56.

Notarianni et al., "Derivation of pluripotent, embryonic cell lines from the pig and sheep," J. Reprod. Fert., Suppl. 43 (1991), pp. 255-260.

Reddy et al., "Fluorescence-activated sorting of totipotent embryonic stem cells expressing developmentally regulated *lacZ* fusion genes," Proc. Natl. Acad. Sci. USA, vol. 89, pp. 6721-6725, Aug. 1992.

Thomson et al., "Isolation of a primate embryonic stem cell line," Proc. Natl. Acad. Sci. USA, vol. 92, pp. 7844-7848, Aug. 1995.

Zhou et al., "CD14$^+$ blood monocytes can differentiate into functionally mature CD83$^+$ dendritic cells," Proc. Natl. Acad. Sci. USA, vol. 93, pp. 2588-2592, Mar. 1996.

Pera et al., "Human embryonic stem cells," Journal of Cell Science 113, 5-10 (2000).

Lowell, Sally, "Stem cells show their potential," Trends in Cell Biology, vol. 10, May 2000, pp. 210-211.

Asahara et al., "Stem cell therapy and gene transfer for regeneration," Gene Therapy (2000) 7, pp. 451-457.

Sesragnoli, et al., "Dendritic cell differentiation from hematopoietic CD34$^+$ progenitor cells," Journal of Biological Regulators and Homeostatic Agents, 2001, vol. 15, No. 1, Jan.-Mar. 2001, pp. 49-52.

Itskovitz-Eldor et al., "Differentiation of Human Embryonic Stem Cells into Embryoid Bodies Comprising the Three Embryonic Germ Layers," Molecular Medicine, 6(2):88-95 (2000).

Thomson et al., "Pluripotent Cell Lines Derived from Common Marmoset (*Callithrix jacchus*) Blastocysts," Biology of Reproduciton 55, (1996), pp. 254-259.

Schuldincr et al., "Effects of eight growth factors on the differentiation of cells derived from human embryonic stem cells," PNAS, Oct. 10, 2000, vol. 97, No. 21, pp. 11307-11312.

Bouwens, Luc, , "Transdifferentiation Versus Stem Cell Hypothesis for the Regeneration of Islet Beta-Cells in the Pancreas," Microscopy Research and Technique 43:332-336 (1998).

Chalmers-Redman et al., "In Vitro Propagation and Inducible Differentiation of Multipotential Progenitor Cells from Human Fetal Brain," Neuroscience, vol. 76, No. 4, 1997, pp. 1121-1128.

Steinhelper et al., "Proliferation in vivo and in culture of differentiated adult atrial cardiomyocytes from transgenic mice," American Physiological Society, 0363-6135/90, pp. H1826-H1834, 1990.

Chen et al., "Therapeutic Benefit of Intravenous Administration of Bone Marrow Stromal Cells After Cerebral Ischemia in Rats," Stroke, 2001; 32:1005-1011.

Koh et al., "Long-term survival of AT-1 cardiomyocyte grafts in syngeneic myocardium," American Physiological Society, 0363-6135/93, pp. H1727-H1733, 1993.

Koh et al., "Differentiation and Long-Term Survival of C2C12 Myoblast Grafts in Heart," J. Clin. Invest., vol. 92, Sep. 1993, pp. 1548-1554.

Evans et al., "Establishment in culture of pluripotential cells from mouse embryos," Nature, vol. 292, Jul. 9, 1981, pp. 154-156.

Koh et al., "Strategies for Myocardial Repair," Journal of Interventional Cardiology, vol. 8, No. 4, 1995, pp. 387-393.

Dewitt, Natalie, "Nature Insight Stem Cells," Macmillan Magazines Ltd. 2001, p. 87.

Toma et al., "Isolation of multipotent adult stem cells from the dermis of mammalian skin," Nature Cell Biology, vol. 3, Sep. 2001, pp. 778-784.

Xu et al., "Feeder-free growth of undifferentiated human embryonic stem cells," Nature Biotechnology, vol. 19, Oct. 2001, pp. 971-974.

Jones et al., "Human Embryonic Stem Cell Technology," Seminars in Reproductive Medicine, vol. 18, No. 2, 2000, pp. 219-223.

Orlic et al., "Bone marrow cells regenerate infarcted myocardium," Nature 2001, Apr. 5; 410(6829):701-5.

Beltrami et al., "Evidence that human cardiac myocytes divide after myocardial infarction," N. Engl. J. Med. Jun. 7, 2001; 344(23):1750-7.

Gmyr et al., "Adult human cytokeratin 19-positive cells reexpress insulin promoter factor 1 in vitro: further evidence for pluripotent pancreatic stem cells in humans," Medline(R) (Dialog File 154, Item 18), p. SL03752, 2000.

Gunsilius et al., "Hematopoietic stem cells," Biomed Pharma, 2001, 55, pp. 186-194.

Kehat et al., "Human embryonic stem cells can differentiate into myocytes with structural and functional properties of cardiomyocytes," The Journal of Clinical Investigation, Aug. 2001, vol. 108, No. 3, pp. 407-414.

Richards et al., "Human feeders support prolonged undifferentiated growth of human inner cell masses and embryonic stem cells," Nature Biotechnology, http://www.nature.com/naturebiotechnology 2002, pp. 1-4.

First et al., "Systems for Production of Calves from Cultured Bovine Embryonic Cells," Reprod. Fertil. Dev., 1994, 6, pp. 553-562.

Sims et al., "Production of Fetuses from Totipotent Cultured Bovine Inner Cell Mass Cells," Theriogenology 39:313, 1993, p. 313.

Bongso et al., "Isolation and culture inner cell mass cells from human blastocysts," Human Reproduction, vol. 9, No. 11, pp. 2110-2117, 1994.

Piedrahita et al., "Influence of Feeder Layer Type on the Efficiency of Isolation of Porcine Embryo-Derived Cell lines," Theriogenology, Nov. 1990, vol. 34, No. 5, pp. 865-877.

Galli et al., "Embryonic stem cells in farm animals," Zygote 2 Nov. 1994, pp. 385-389.

Bongso et al., "The Growth of Inner Cell Mass Cells from Human Blastocysts," Theriogenology 41:167, 1994, p. 167.

Doetschman et al., "Establishment of Hamster Blastocyst-Derived Embryonic Stem (ES) Cells," Developmental Biology 127, 1988, pp. 224-227.

Reyes et al., "Origin of endothelial progenitors in human postnatal bone marrow," The Journal of Clinical Investigation, Feb. 2002, vol. 109, No. 3, pp. 1-10.

Smith, Austin, "Cell therapy: In search of pluripotency," Current Biology, 1998, 8:R802-R804.

Reyes et al., "Characterization of Multilineage Mesodermal Progenitor Cells in Adult Marrow," Abstract No. 124, American Society for Hematology, Dec. 2001.

Reyes et al., "Turning Marrow into Brain: Generation of Glial and Neuronal Cells from Adult Bone Marrow Mesenchymal Stem Cells," Abstract No. 1676, American Society for Hematology, Dec. 2001.

Reyes et al., "Skeletal Smooth and Cardiac Muscle Differentiation from Single Adult Marrow Derived Mesodermal Progenitor Cells," Abstract No. 2610, American Society for Hematology, Dec. 2001.

Gupta et al., "Human Bone Marrow Derived Mesodermal Progenitor Cells (MPC) In Vitro Correct the Biochemical Abnormality in Hurler Syndrome," Abstract No. 1199, American Society for Hematology, Dec. 2001.

Reyes et al., "In Vitro and In Vivo Characterization of Neural Cells Derived from Mesenchymal Stem Cells," Abstract No. 2126, American Society for Hematology, Dec. 2001.

Reyes et al., "Endotheial Cells Generated from Human Marrow Derived Mesenchymal Stem Cells (MSC)," Abstract No. 2276, American Society for Hematology, Dec. 2001.

Thompson, Larry, Fetal Transplants Show Promise, Science, vol. 257, Aug. 14, 1992, pp. 868-8690.

Zhao LR, Duan WM, Reyes M, Verfaillie CM, Low WC, *Immunohistochemical Identification of Multipotent Adult Progenitor Cells From Human Bone Marrow After Transplantation Into the Rat Brain*, Brain Res Brain Res Protoc. Mar. 2003; 11(1):38-45. PMID: 12697261 [PubMed—in process].

Jiang Y, Vaessen B, Lenvik T, Blackstad M, Reyes M, Verfaillie CM, *Multipotent Progenitor Cells Can Be Isolated From Postnatal MurineBone Marrow, Muscle, and Brain*, Exp Hematol. Aug. 2002;30(8):896-904. PMID: 12160841 [PubMed—indexed for MEDLINE].

Jiang Y, Jahagirdar BN, Reinhardt RL, Schwartz RE, Keene CD, Ortiz-Gonzalez XR, Reyes M, Lenvik T, Lund T, Blackstad M, Du J, Aldrich S, Lisberg A, Low WC, Largaespada DA, Verfaillie CM, *Pluripotency of Mesenchymal Stem Cells Derived From Adult Marrow*, Nature. Jul. 4, 2002;418(6893):41-9. PMID: 12077603 [PubMed—indexed for MEDLINE].

Schwartz RE, Reyes M, Koodie L, Jiang Y, Blackstad M, Lund T, Lenvik T, Johnson S, Hu WS, Verfaillie CM, *Multipotent Adult Progenitor Cells From Bone Marrow Differentiate Into Functional Hepatocyte-Like Cells*, J Clin Invest. May 2002;109(10):1291-302. PMID: 12021244 [PubMed—indexed for MEDLINE].

Zhao LR, Duan WM, Reyes M, Keene CD, Verfaillie CM, Low WC, *Human Bone Marrow Stem Cells Exhibit Neural Phenotypes and Ameliorate Neurological Deficits After Grafting Into the Ischemic Brain of Rats*, Exp Neurol. Mar. 2002;174(1): 11-20. PMID: 11869029 [PubMed—indexed for MEDLINE.

Lamming CE, Augustin L, Blackstad M, Lund TC, Hebbel RP, Verfaillie CM, *Spontaneous Circulation of Myeloid-Lymphoid-Initiating Cells and SCID-Repopulating Cells in Sickle Cell Crisis*, J Clin Invest. Mar. 2003;111(6):811-9. PMID: 12639987 [PubMed—indexed for MEDLINE].

Qi H, Aguiar DJ, Williams SM, La Pean A, Pan W, Verfaillie CM, *Identification of Genes Responsible for Osteoblast Differentiation From Human Mesodermal Progenitor Cells*, Proc Natl Acad Sci U S A. Mar. 18, 2003;100(6):3305-10. Epub Mar. 11, 2003. PMID: 12631704 [PubMed—indexed for MEDLINE].

Verfaillie, Catherine M., "Investigator Profile," *Journal of Hematotherapy and Stem Cell Research*, 11, 441-444, 2002.

Verfaillie CM, Pera MF, Lansdorp PM, *Stem Cells: Hype and Reality*, Hematology (Am Soc Hematol Educ Program). 2002;:369-91. PMID: 12446433 [PubMed—in process].

Verfaillie CM, *Optimizing Hematopoietic Stem Cell Engraftment: A Novel Role for Thrombopoietin*, J Clin Invest. Aug. 2002; 110(3):303-4. Review. No abstract available. PMID: 12163447 [PubMed—indexed for MEDLINE].

Liu H, Verfaillie CM, *Myeloid-Lymphoid Initiating Cells (ML-IC) Are Highly Enriched in the Rhodamine-C-Kit(+)CD33(−)CD38(−) Fraction of Umbilical Cord CD34(+) Cells*, Exp Hematol. Jun. 2002;30(6):582-9. PMID: 12063025 [PubMed—indexed for MEDLINE].

Lewis ID, Verfaillie CM, *Multi-Lineage Expansion Potential of Primitive Hematopoietic Progenitors: Superiority of Umbilical Cord*

Blood Compared to Mobilized Peripheral Blood, Exp Hematol. Sep. 2000;28(9):1087-95. PMID: 11008022 [PubMed—indexed for MEDLINE].

Verfaillie CM, *Meeting Report on an NHLBI Workshop on Ex Vivo Expansion of Stem Cells, Jul. 29, 1999, Washington, D.C. National Heart Lung and Blood Institute*, Exp Hematol. Apr. 2000;28(4):361-4. No abstract available. PMID: 10781893 [PubMed—indexed for MEDLINE].

Punzel M, Wissink SD, Miller JS, Moore KA, Lemischka IR, Verfaillie CM, *The Myeloid-Lymphoid Initiating Cell (ML-IC) Assay Assesses the Fate of Multipotent Human Progenitors in Vitro*, Blood. Jun. 1, 1999;93(11):3750-6. PMID: 10339481 [PubMed—indexed for MEDLINE].

Roy V, Verfaillic CM, *Expression and Function of Cell Adhesion Molecules on Fetal Liver, Cord Blood and Bone Marrow Hematopoietic Progenitors: Implications for Anatomical Localization and Developmental Stage Specific Regulation of Hematopoiesis*, Exp Hematol. Feb. 1999;27(2):302-12. PMID: 10029170 [PubMed—indexed for MEDLINE].

Miller JS, McCullar V, Verfaillie CM, *Ex Vivo Culture of CD34+/Lin-/DR- Cells in Stroma-Derived Soluble Factors, Interleukin-3, and Macrophage Inflammatory Protein-1alpha Maintains Not Only Myeloid But Also Lymphoid Progenitors in a Novel Switch Culture Assay*, Blood. Jun. 15, 1998;91(12):4516-22. PMID: 9616147 [PubMed—indexed for MEDLINE].

Verfaillie CM, *Stem Cells in Chronic Myelogenous Leukemia*, Hematol Oncol Clin North Am. Dec. 1997;11(6):1079-114. Review. PMID: 9443047 [PubMed—indexed for MEDLINE].

Prosper F, Stroncek D, Verfaillie CM, *Phenotypic and Functional Characterization of Long-Term Culture-Initiating Cells Present in Peripheral Blood Progenitor Collections of Normal Donors Treated With Granulocyte Colony-Stimulating Factor*, Blood. Sep. 15, 1996;88(6):2033-42. PMID: 8822922 [PubMed—indexed for MEDLINE.

Lodie, Tracey, et al., "Systematic Analysis of Reportedly Distinct Populations of Multipotent Bone Marrow-Derived Stem Cells reveals a Lack of Distinction," *Tissue Engineering*, 8, 5, 739-751, 2002.

Pagen Westphal, Sylvia, "Adult Bone Marrow Eyed as Source of Stem Cells," Boston Globe, Jan. 24, 2002.

Pagen Westphal, Sylvia, "Ultimate Stem Cell Discovered," New Scientist, Jan. 23, 2002.

Wade, Nicholas, Gay Stolberg, Sheryl, "Scientists Herald a Versatile Adult Cell" The New York Times on the Web, Jan. 25, 2002.

Associated Press, "Adult Marrow Cells Show Versatility," The New York Times on the Web, Jan. 25, 2002.

Rosford et al. "The octamer motif present in the Rex-I promoter binds Oct-1 and Oct-3 expressed by EC cells and ES cells" Biochemical and Biophysical Research Communications, vol. 203(3), 1994, pp. 1795-1802.

Hilton D J et al. "Distribution and Comparison of Receptors for Leukemia Inhibitory Factor on Murine Hemopoietic and Hepatic Cells" Journal of Cellular Physiology, vol. 146(2), 1991, pp. 207-215.

Rosner M H et al. "Oct-3 is a maternal factor required for the first mouse embryonic division" Cell, vol. 64(6), 1991, pp. 1103-1110.

Cassiede et al. "Osteochondrogenic potential of marrow mesenchymal progenitor cells exposed to TGF-beta-1 or PDGF-BB as assayed in vivo and in vitro" Journal of Bone and Mineral Research, vol. 11(9), 1996, pp. 1264-1273.

Lennon et al. "A chemically defined medium supports in vitro proliferation and maintains the osteochondral potential of rat marrow-derived mesenchymal stem cells," Experimental Cell Research, vol. 219(1), 1995, pp. 211-222.

Pittenger et al. "Multilineage potential of adult human mesenchymal Stem Cells", Science, US, American Association for the Advancement of Science, vol. 284(5411) (Apr. 2, 1999), pp. 143-147.

Ben-Shushan et al. "Rex1, a gene encoding a trasncription factor expressed in the early embryo, is regulated via Oct-3/4 and Oct-6 binding to and octamer site and a novel protein, Rox-1, binding to an adjacent site." Molecular and Cellular Biology, vol. 18(4), Apr. 1998, pp. 1866-1878.

Raptis A et al. "Polymorphism in CD33 and CD34 genes: A source of minor histocompatibility antigens on haemopoietic progenitor cells?" British Journal of Haematology, vol. 102(5), 1998, pp. 1354-1358.

Grigoriadou, K. et al. MHC Class Ia Molecules Alone Control NK-Mediated Bone Marrow Graft Rejection. European Journal of Immunology. Nov. 1999, vol. 29(11), pp. 3683-3690.

Gulcher, J. et al. Population Genetics:Laying the Groundwork for Genetic Disease Modeling andTargeting. Clinical Chemicak Laboratory Medicine. 1998, vol. 36(8), pp. 523-727.

Brazelton TR, Rossi FM, Keshet GI, Blau HM. From marrow to brain: expression of neuronal phenotypes in adult mice. Science. Dec. 1, 2000;290(5497):1775-9.

Clarke DL, Johansson CB, Wilbertz J, Veress B, Nilsson E, Karlstrom H, Lendahl U, Frisen J. Generalized potential of adult neural stem cells. Science. Jun. 2, 2000;288(5471):1660-3.

Johansson CB, Svensson M, Wallstedt L, Janson AM, Frisen J. Neural stem cells in the adult human brain. Exp Cell Res. Dec. 15, 1999;253(2):733-6.

Mezey E, Chandross KJ, Harta G, Maki RA, McKercher SR. Turning blood into brain: cells bearing neuronal antigens generated in vivo from bone marrow. Science. Dec. 1, 2000;290(5497):1779-82.

Morshead CM, Benveniste P, Iscove NN, van der Kooy D. Hematopoietic competence is a rare property of neural stem cells that may depend on genetic and epigenetic alterations. Nat Med. Mar. 2002;8(3):268-73.

Petersen BE, Bowen WC, Patrene KD, Mars WM, Sullivan AK, Murase N, Boggs SS, Greenberger JS, Goff JP. Bone marrow as a potential source of hepatic oval cells. Science. May 14, 1999;284(5417):1168-70.

Sanchez-Ramos J, Song S, Cardozo-Pelaez F, Hazzi C, Stedeford T, Willing A, Freeman TB, Saporta S, Janssen W, Patel N, Cooper DR, Sanberg PR. Adult bone marrow stromal cells differentiate into neural cells in vitro. Exp Neurol. Aug. 2000;164(2):247-56.

Scintu F, Reali C, Pillai R, Badiali M, Sanna MA, Argiolu F, Ristaldi MS, Sogos V. Differentiation of human bone marrow stem cells into cells with a neural phenotype: diverse effects of two specific treatments. BMC Neurosci. Feb. 16, 2006;7:14.

Giles, J., "The trouble with replication" Nature, 422:344-347 (2006).

Verfaillie, C.M., Multipotent adult progenitor cells: an update: Novartis Found Symp., 254:55-65 (2005).

Aldhous et al., "Fresh questions on stem cell findings" New Scientist, Mar. 21, 2007.

Izadpanah et al., "Biologic Properties of Mesenchymal Stem Cells Derived from Bone Marrow and Adipose Tissue" Journal of Cellular Biochemistry, 99:1285-1297 (2006).

Long et al., Neural Cell Differentiation In Vitro from Adult Human Bone Marrow Mesenchymal Stem Cells Stem Cells and Development, 14:65-69 (2005).

Moriscot et al., "Human Bone Marrow Mesenchymal Stem Cells Can Express Insulin and Key Transcription Factors of the Endocrine Pancreas Developmental Pathway upon Genetic and/or Microenvironmental Manipulation In Vitro" Stem Cells, 23:594-604 (2005).

Sanchez-Ramos at al., "Adult Bone Marrow Stromal Cells Differentiate into Neural Cells in Vitro" Experimental Neurology, 164:247-256 (2000).

Anjos-Afonso and Bonnet, "Nonhematopoietic/endothelial SSEA-1+ cells define the most primitive progenitors in the adult murine bone marrow mesenchymal compartment" Blood, 109:1298-1306 (2007).

Bertani et al., "Neurogenic potential of human mesenchymal stem cells revisited: analysis by immunostaining, time-lapse video and microarray" Journal of Cell Science, 118:3925-3936 (2005).

Bodnar et al., "Extension of life-span by introduction of telomerase into normal human cells" Science, 279:349-352 (1998).

Horwitz et al., "Clarification of the nomenclature for MSC: the international society for cellular therapy position paper" Cytotherapy, 7:393-395 (2005).

Lazarus et al., "Ex vivo expansion and subsequence infusion of human bone marrow-derived stromal progenitor cells (mesenchymal progenitor cells): implications for therapeutic use" Bone Marrow Transplantation, 16:557-564 (1995).

Lu at al., "Induction of bone marrow stromal cells to neurons: differentiation, transdifferentiation, or artifact?" Journal of Neuroscience Research, 77:174-101 (2004).

Neuhuber et al., "Reevaluation of in vitro differentiation protocols for bone marrow stromal cells: disruption of actin cytoskeleton induces rapid morphological changes and mimcs neuronal phenotype" Journal of Neuroscience Research, 77:192-204 (2004).

Simonsen et al., "Telomerase expression extends the proliferative life-span and maintains the osteogenic potential of human bone marrow stromal cells" Nature Biotechnology, 20:592-596 (2002).

Zimmerman et al., "Lack of telomerase activity in human mesenchymal stem cells" Leukemia, 17:1146-1149 (2003).

* cited by examiner

ASSAY UTILIZING MULTIPOTENT ADULT STEM CELLS

RELATED CASES

This application claims the benefit of U.S. Provisional Application No. 60/343,386, filed Oct. 25, 2001, U.S. Provisional Application No. 60/310,625, filed Aug. 7, 2001, U.S. Provisional Application No. 60/269,062, filed Feb. 15, 2001, U.S. Provisional Application No. 60/268,786, filed Feb. 14, 2001, which are hereby incorporated by reference for all purposes. Applicants also claim priority of WO 01/11011, 60/147,324 and 60/164,650 and these applications are hereby incorporated by reference into this text; any teachings therein may be used in the practice of this invention. The present application is a continuation-in-part of WO 01/11011, which is attached herein at Appendix 1 and is part of the present application. Documents incorporated by reference into this text are not admitted to be prior art.

FIELD OF THE INVENTION

The present invention relates generally to mammalian multipotent adult stem cells (MASC), and more specifically to methods for obtaining, maintaining and differentiating MASC. Uses of MASC in the therapeutic treatment of disease are also provided.

BACKGROUND OF THE INVENTION

Organ and tissue generation from stem cells, and their subsequent transplantation provide promising treatments for a number of pathologies, making stem cells a central focus of research in many fields. Stem cell technology provides a promising alternative therapy for diabetes, Parkinson's disease, liver disease, heart disease, and autoimmune disorders, to name a few. However, there are at least two major problems associated with organ and tissue transplantation.

First, there is a shortage of donor organs and tissues. As few as 5 percent of the organs needed for transplant in the United States alone ever become available to a recipient (Evans, et al. 1992). According to the American Heart Association, only 2,300 of the 40,000 Americans who needed a new heart in 1997 received one. The American Liver Foundation reports that there are fewer than 3,000 donors for the nearly 30,000 patients who die each year from liver failure.

The second major problem is the potential incompatibility of the transplanted tissue with the immune system of the recipient. Because the donated organ or tissue is recognized by the host immune system as foreign, immunosuppressive medications must be provided to the patient at a significant cost-both financially and physically.

Xenotransplantation, or transplantation of tissue or organs from another species, could provide an alternative means to overcome the shortage of human organs and tissues. Xenotransplantation would offer the advantage of advanced planning. The organ could be harvested while still healthy and the patient could undergo any beneficial pretreatment prior to transplant surgery. Unfortunately, xenotransplantation does not overcome the problem of tissue incompatibility, but instead exacerbates it. Furthermore, according to the Centers for Disease Control, there is evidence that damaging viruses cross species barriers. Pigs have become likely candidates as organ and tissue donors, yet cross-species transmission of more than one virus from pigs to humans has been documented. For example, over a million pigs were recently slaughtered in Malaysia in an effort to contain an outbreak of Hendra virus, a disease that was transmitted to more than 70 humans with deadly results (Butler, D. 1999).

Stem Cells: Definition and Use

The most promising source of organs and tissues for transplantation, therefore, lies in the development of stem cell technology. Theoretically, stem cells can undergo self-renewing cell division to give rise to phenotypically and genotypically identical daughters for an indefinite time and ultimately can differentiate into at least one final cell type. By generating tissues or organs from a patient's own stem cells, or by genetically altering heterologous cells so that the recipient immune system does not recognize them as foreign, transplant tissues can be generated to provide the advantages associated with xenotransplantation without the associated risk of infection or tissue rejection.

Stem cells also provide promise for improving the results of gene therapy. A patient's own stem cells could be genetically altered in vitro, then reintroduced in vivo to produce a desired gene product. These genetically altered stem cells would have the potential to be induced to differentiate to form a multitude of cell types for implantation at specific sites in the body, or for systemic application. Alternately, heterologous stem cells could be genetically altered to express the recipient's major histocompatibility complex (MHC) antigen, or no MHC antigen, allowing transplantion of cells from donor to recipient without the associated risk of rejection.

Stem cells are defined as cells that have extensive proliferation potential, differentiate into several cell lineages, and repopulate tissues upon transplantation. The quintessential stem cell is the embryonic stem (ES) cell, as it has unlimited self-renewal and multipotent differentiation potential (Thomson, J. et al. 1995; Thomson, J. A. et al. 1998; Shamblott, M. et al. 1998; Williams, R. L. et al. 1988; Orkin, S. 1998; Reubinoff, B. E., et al. 2000). These cells are derived from the inner cell mass of the blastocyst (Thomson, J. et al. 1995; Thomson, J. A. et al. 1998; Martin, G. R. 1981), or can be derived from the primordial germ cells from a post-implantation embryo (embryonal germ cells or EG cells). ES and EG cells have been derived from mouse, and more recently also from non-human primates and humans. When introduced into mouse blastocysts, ES cells can contribute to all tissues of the mouse (animal) (Orkin, S. 1998). Murine ES cells are therefore pluripotent. When transplanted in post-natal animals, ES and EG cells generate teratomas, which again demonstrates their multipotency. ES (and EG) cells can be identified by positive staining with the antibodies to stage-specific embryonic antigens (SSEA) 1 and 4.

At the molecular level, ES and EG cells express a number of transcription factors highly specific for these undifferentiated cells. These include oct-4 and Rex-1, leukemia inhibitory factor receptor (LIF-R). The transcription factors sox-2 and Rox-1 are expressed in both ES and non-ES cells. Oct-4 is expressed in the pregastrulation embryo, early cleavage stage embryo, cells of the inner cell mass of the blastocyst, and embryonic carcinoma (EC) cells. In the adult animal, oct-4 is only found in germ cells.

Oct-4, in combination with Rox-1, causes transcriptional activation of the Zn-finger protein Rex-1, and is also required for maintaining ES in an undifferentiated state. The oct-4 gene is down-regulated when cells are induced to differentiate in vitro. Several studies have shown that oct-4 is required for maintaining the undifferentiated phenotype of ES cells, and that it plays a major role in determining early steps in embryogenesis and differentiation. Sox-2, is required with oct-4 to retain the undifferentiated state of ES/EC and to maintain murine, but not human, ES cells. Human or murine primordial germ cells require presence of LIF. Another hallmark of ES cells is presence of high levels of telomerase, which provides these cells with an unlimited self-renewal potential in vitro.

Stem cells have been identified in most organs or tissues. The best characterized is the hematopoietic stem cell (HSC). This mesoderm-derived cell has been purified based on cell surface markers and functional characteristics. The HSC, isolated from bone marrow (BM), blood, cord blood, fetal liver and yolk sac, is the progenitor cell that generates blood cells or following translation reinitiates multiple hematopoietic lineages and can reinitiate hematopoiesis for the life of a recipient. (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 759,793; DiGuisto, et al, U.S. Pat. No. 5,681,599; Tsukamoto, et al., U.S. Pat. No. 5,716,827; Hill, B., et al. 1996.) When transplanted into lethally irradiated animals or humans, HSCs can repopulate the erythroid, neutrophil-macrophage, megakaryocyte and lymphoid hemopoietic cell pool. In vitro, hemopoietic stem cells can be induced to undergo at least some self-renewing cell divisions and can be induced to differentiate to the same lineages as is seen in vivo. Therefore, this cell fulfills the criteria of a stem cell. Stem cells which differentiate only to form cells of hematopoietic lineage, however, are unable to provide a source of cells for repair of other damaged tissues, for example, heart or lung tissue damaged by high-dose chemotherapeutic agents.

A second stem cell that has been studied extensively is the neural stem cell (NSC) (Gage F. H. 2000; Svendsen C. N. et al, 1999; Okabe S. et al. 1996). NSCs were initially identified in the subventricular zone and the olfactory bulb of fetal brain. Until recently, it was believed that the adult brain no longer contained cells with stem cell potential. However, several studies in rodents, and more recently also non-human primates and humans, have shown that stem cells continue to be present in adult brain. These stem cells can proliferate in vivo and continuously regenerate at least some neuronal cells in vivo. When cultured ex vivo, NSCs can be induced to proliferate, as well as to differentiate into different types of neurons and glial cells. When transplanted into the brain, NSCs can engraft and generate neural cells and glial cells. Therefore, this cell too fulfills the definition of a stem cell, albeit a hematopoetic stem cell.

Clarke et al. reported that NSCs from Lac-Z transgenic mice injected into murine blastocysts or in chick embryos contribute to a number of tissues of the chimeric mouse or chicken embryo (Clarke, D. L. et al. 2000). LacZ-expressing cells were found with varying degree of mosaicism, not only in the central nervous system, but also in mesodermal derivatives as well as in epithelial cells of the liver and intestine but not in other tissues, including the hematopoietic system. These studies therefore suggested that adult NSCs may have significantly greater differentiation potential than previously realized but still do not have the pluripotent capability of ES or of the adult derived multipotent adult stem cells (MASC) described in Furcht et al. (International Application No. PCT/US00/21387) and herein The terms MASC, MAPC and MPC can also be used interchagably to describe adult derived multipotent adult stem cells.

Therapies for degenerative and traumatic brain disorders would be significantly furthered with cellular replacement therapies. NSC have been identified in the sub-ventricular zone (SVZ) and the hippocampus of the adult mammalian brain (Ciccolini et al., 1998; Morrison et al., 1999; Palmer et al., 1997; Reynolds and Weiss, 1992; Vescovi et al., 1999) and may also be present in the ependyma and other presumed non-neurogenic areas of the brain (Doetsch et al., 1999; Johansson et al., 1999; Palmer et al., 1999). Fetal or adult brain-derived NSC can be expanded ex vivo and induced to differentiate into astrocytes, oligodendrocytes and functional neurons (Ciccolini et al., 1998; Johansson et al., 1999; Palmer et al., 1999; Reynolds et al., 1996; Ryder et al., 1990; Studer et al., 1996; Vescovi et al., 1993). In vivo, undifferentiated NSC cultured for variable amounts of time differentiate into glial cells, GABAergic and dopaminergic neurons (Flax et al., 1998; Gage et al., 1995; Suhonen et al., 1996). The most commonly used source of NSC is allogeneic fetal brain, which poses both immunological and ethical problems. Alternatively, NSC could be harvested from the autologous brain. As it is not known whether pre-existing neural pathology will affect the ability of NSC to be cultured and induced to differentiate into neuronal and glial cells ex vivo, and because additional surgery in an already diseased brain may aggravate the underlying disease, this approach is less attractive.

The ideal source of neurons and glia for replacement strategies would be cells harvestable from adult, autologous tissue different than the brain that was readily accessible and that can be expanded in vitro and differentiated ex vivo or in vivo to the cell type that is deficient in the patient. Recent reports have suggested that BM derived cells acquire phenotypic characteristics of neuroectodermal cells when cultured in vitro under NSC conditions, or when they enter the central nervous system (Sanchez-Ramos et al., 2000; Woodbury et al., 2000). The phenotype of the BM cells with this capability is not known. The capacity for differentiation of cells that acquire neuroectodermal features to other cell types is also unknown.

A third tissue specific cell with stem cell properties is the mesenchymal stem cell (MSC), initially described by Fridenshtein (1982). MSC, originally derived from the embryonal mesoderm and isolated from adult BM, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or MSCs, therefore, could provide a source for a number of cell and tissue types. A number of MSCs have been isolated. (See, for example, Caplan, A., et al., U.S. Pat. No. 5,486,359; Young, H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., 1997; Cassiede P., et al., 1996; Johnstone, B., et al., 1998; Yoo, et al., 1998; Gronthos, S., 1994).

Of the many MSC that have been described, all have demonstrated limited differentiation to form cells generally considered to be of mesenchymal origin. To date, the most multipotent MSC reported is the cell isolated by Pittenger, et al., which expresses the $SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD45^-$ phenotype. This cell is capable of differentiating to form a number of cell types of mesenchymal origin, but is apparently limited in differentiation potential to cells of the mesenchymal lineage, as the team who isolated it noted that hematopoietic cells were never identified in the expanded cultures (Pittenger, et al., 1999).

Other tissue-specific stem cells have been identified, including gastrointestinal stem cells (Potten, C. 1998), epidermal stem cells (Watt, F. 1997), and hepatic stem cells, also termed oval cells (Alison, M. et al. 1998). Most of these are less well characterized.

Compared with ES cells, tissue specific stem cells have less self-renewal ability and, although they differentiate into multiple lineages, they are not pluripotent. No studies have addressed whether tissue specific cells express the markers described above as seen in ES cells. In addition, the degree of telomerase activity in tissue specific or lineage comitted stem cells has not been fully explored, in part because large numbers of highly enriched populations of these cells are difficult to obtain.

Until recently, it was thought that tissue specific stem cells could only differentiate into cells of the same tissue. A number of recent publications have suggested that adult organ specific stem cells may be capable of differentiation into cells of different tissues. However, the true nature of these types of cells has not been fully discerned. A number of studies have shown that cells transplanted at the time of a BM transplant can differentiate into skeletal muscle (Ferrari 1998; Gussoni 1999). This could be considered within the realm of possible differentiation potential of mesenchymal cells that are present in marrow. Jackson published that muscle satellite cells can differentiate into hemopoietic cells, again a switch in phenotype within the splanchnic mesoderm of the embryo (Jackson 1999). Other studies have shown that stem cells from one embryonic layer (for instance splanchnic mesoderm) can differentiate into tissues thought to be derived during embryogenesis from a different embryonic layer. For instance, endothelial cells or their precursors detected in humans or animals that underwent marrow transplantation are at least in part derived from the marrow donor (Takahashi, 1999; Lin, 2000). Thus, visceral mesoderm and not splanchnic mesoderm, capabilities such as MSC, derived progeny are transferred with the infused marrow. Even more surprising are the reports demonstrating both in rodents and humans that hepatic epithelial cells and biliary duct epithelial cells can be seen in recipients that are derived from the donor marrow (Petersen, 1999; Theise, 2000; Theise, 2000). Likewise, three groups have shown that NSCs can differentiate into hemopoietic cells. Finally, Clarke et al. reported that cells be termed NSCs when injected into blastocysts can contribute to all tissues of the chimeric mouse (Clarke et al., 2000).

It is necessary to point out that most of these studies have not conclusively demonstrated that a single cell can differentiate into tissues of different organs. Also, stem cells isolated from a given organ may not necessarily be a lineage committed cell. Indeed most investigators did not identify the phenotype of the initiating cell. An exception is the study by Weissman and Grompe, who showed that cells that repopulated the liver were present in $Lin^-Thy_1LowSca_1^+$ marrow cells, which are highly enriched in HSCs. Likewise, the Mulligan group showed that marrow Sp cells, highly enriched for HSC, can differentiate into muscle and endothelium, and Jackson et al. showed that muscle Sp cells are responsible for hemopoietic reconstitution (Gussoni et al., 1999).

Transplantation of tissues and organs generated from heterologous ES cells requires either that the cells be further genetically modified to inhibit expression of certain cell surface markers, or that the use of chemotherapeutic immune suppressors continue in order to protect against transplant rejection. Thus, although ES cell research provides a promising alternative solution to the problem of a limited supply of organs for transplantation, the problems and risks associated with the need for immunosuppression to sustain transplantation of heterologous cells or tissue would remain. An estimated 20 immunologically different lines of ES cells would need to be established in order to provide immunocompatible cells for therapies directed to the majority of the population.

Using cells from the developed individual, rather than an embryo, as a source of autologous or from tissue typing matched allogeneic stem cells would mitigate or overcome the problem of tissue incompatibility associated with the use of transplanted ES cells, as well as solve the ethical dilemma associated with ES cell research. The greatest disadvantage associated with the use of autologous stem cells for tissue transplant thus far lies in their relatively limited differentiation potential. A number of stem cells have been isolated from fully-developed organisms, particularly humans, but these cells, although reported to be multipotent, have demonstrated limited potential to differentiate to multiple cell types.

Thus, even though stem cells with multiple differentiation potential have been isolated previously by others and by the present inventors, a progenitor cell with the potential to differentiate into a wide variety of cell types of different lineages, including fibroblasts, hepatic, osteoblasts, chondrocytes, adipocytes, skeletal muscle, endothelium, stroma, smooth muscle, cardiac muscle and hemopoietic cells, has not been described. If cell and tissue transplant and gene therapy are to provide the therapeutic advances expected, a stem cell or progenitor cell with the greatest or most extensive differentiation potential is needed. What is needed is the adult equivalent of an ES cell.

BM, muscle and brain are the three tissues in which cells with apparent greater plasticity than previously thought have been identified. BM contains cells that can contribute to a number of mesodermal (Ferrari G. et al., 1998; Gussoni E. et al., 1999; Rafii S. et al., 1994; Asahara T. et al., 1997; Lin Y. et al., 2000; Orlic D. et al., 2001; Jackson K. et al., 2001) endodermal (Petersen B. E. et al., 1999; Theise, N. D. et al., 2000; Lagasse E. et al., 2000; Krause D. et al., 2001) and neuroectodermal (Mezey D. S. et al., 2000; Brazelton T. R., et al., 2000, Sanchez-Ramos J. et al., 2000; Kopen G. et al., 1999) and skin (Krause, D. et al., 2001) structures. Cells from muscle may contribute to the hematopoietic system (Jackson K. et al., 1999; Seale P. et al., 2000). There is also evidence that NSC may differentiate into hematopoietic cells (Bjornson C. et al., 1999; Shih C. et al., 2001), smooth muscle myoblasts (Tsai R. Y. et al., 2000) and that NSC give rise to several cell types when injected in a mouse blastocyst (Clarke, D. L. et al., 2000).

The present study demonstrates that cells with multipotent adult progenitor characteristics can be culture-isolated from multiple different organs, namely BM, muscle and the brain. The cells have the same morphology, phenotype, in vitro differentiation ability and have a highly similar expressed gene profile.

SUMMARY OF THE INVENTION

The present invention is a multipotent adult stem cell (MASC) isolated from a mammal, preferably mouse, rat or human. The cell is derived from a non-embryonic organ or tissue and has the capacity to be induced to differentiate to form at least one differentiated cell type of mesodermal, ectodermal and endodermal origin. In a preferred embodiment, the organ or tissue from which the MASC are isolated is bone marrow, muscle, brain, umbilical cord blood or placenta.

Examples of differentiated cells that can be derived from MASC are osteoblasts, chondrocytes, adipocytes, fibroblasts, marrow stroma, skeletal muscle, smooth muscle, cardiac muscle, occular, endothelial, epithelial, hepatic, pancreatic, hematopoietic, glial, neuronal or oligodendrocytes. Differentiation can be induced in vivo or ex vivo.

The MASC of the present invention is also summarized as a cell that constitutively expresses oct4 and high levels of telomerase and is negative for CD44, MHC class I and MHC class II expression. As a method of treatment, this cell administered to a patient in a therapeutically effective amount. A surprising benefit of this treatment is that no teratomas are formed in vivo.

An object of the invention is to produce a normal, non-human animal comprising MASC. Preferably, the animal is chimeric.

Another embodiment of the invention is a composition comprising a population of MASC and a culture medium that expands the MASC population. It is advantageous in some cases for the medium to contain epidermal growth factor (EGF), platelet derived growth factor (PDGF) and leukemia inhibitory factor (LIF).

The present invention also provides a composition comprising a population of fully or partially purified MASC progeny. The progeny can have the capacity to be further differentiated, or can be terminally differentiated.

In a preferable embodiment, the progeny are of the osteoblast, chondrocyte, adipocyte, fibroblast, marrow stroma, skeletal muscle, smooth muscle, cardiac muscle, occular, endothelial, epithelial, hepatic, pancreatic, hematopoietic, glial, neuronal or oligodendrocyte cell type.

The present invention also provides a method for isolating and propagating MASC by obtaining tissue from a mammal, establishing a population of adherent cells, depleting the population of $CD45^+$ cells, recovering $CD45^-$ cells and culturing them under expansion conditions to produce an expanded cell population. An object of the present invention, therefore, is to produce an expanded cell population obtained by this method.

An aspect of the invention is a method for differentiating MASC ex vivo by isolating and propagating them, and then culturing the propagated cells in the presence of desired differentiation factors. The preferred differentiation factors are basic fibroblast growth factor (bFGF), vascular endothelial growth factor (VEGF), dimethylsulfoxide (DMSO) and isoproterenol; or fibroblast growth factor4 (FGF4) and hepatocyte growth factor (HGF). Another aspect of the invention is the differentiated cell itself.

The invention includes a method for differentiating MASC in vivo, by isolating and expanding them, and then administering the expanded cell population to a mammalian host, wherein said cell population is engrafted and differentiated in vivo in tissue specific cells, such that the function of a cell or organ, defective due to injury, genetic disease, acquired disease or iatrogenic treatments, is augmented, reconstituted or provided for the first time. Using this method, the MASC can undergo self-renewal in vivo.

A further aspect of the invention is a differentiated cell obtained by ex vivo or in vivo differentiation. In a preferred embodiment, the differentiated cell is ectoderm, mesoderm or endoderm. In another preferred embodiment, the differentiated cell is of the osteoblast, chondrocyte, adipocyte, fibroblast, marrow stroma, skeletal muscle, smooth muscle, cardiac muscle, occular, endothelial, epithelial, hepatic, pancreatic, hematopoietic, glial, neuronal or oligodendrocyte cell type.

An important application of this technology is the method of treating a patient by administering a therapeutically effective amount of MASC or their progeny. The progeny can either have the capacity to be further differentiated, or can be terminally differentiated. An unexpected benefit of this approach is that the need for pretreatment and/or post treatment of the patient with irradiation, chemotherapy, immunosuppressive agents or other drugs or treatments is reduced or eliminated. The induction of tolerance before or during treatment is also not required.

Such treatment can treat a variety of diseases and conditions, including cancer, cardiovascular disease, metabolic disease, liver disease, diabetes, hepatitis, hemophilia, degenerative or traumatic neurological conditions, autoimmune disease, genetic deficiency, connective tissue disorders, anemia, infectious disease and transplant rejection.

MASC or their progeny are administered via localized injection, including catheter administration, systemic injection, parenteral administration, oral administration, or intrauterine injection into an embryo. Administration can be in conjunction with a pharmaceutically acceptable matrix, which may be biodegradable.

MASC or their progeny, administered to a patient, alter the immune system to resist viral, bacterial or fungal infection.

Surprisingly, teratomas are not formed when MASC or their progeny are administered to a patient.

When administered to a patient, MASC or their progeny also are able to augment, reconstitute or provide for the first time the function of a cell or organ defective due to injury, genetic disease, acquired disease or iatrogenic treatments. The organ is any of bone marrow, blood, spleen, liver, lung, intestinal tract, brain, immune system, circulatory system, bone, connective tissue, muscle, heart, blood vessels, pancreas, central nervous system, peripheral nervous system, kidney, bladder, skin, epithelial appendages, breast-mammary glands, fat tissue, and mucosal surfaces including oral esophageal, vaginal and anal. Examples of diseases treatable by this method are cancer, cardiovascular disease, metabolic disease, liver disease, diabetes, hepatitis, hemophilia, degenerative or traumatic neurological conditions, autoimmune disease, genetic deficiency, connective tissue disorders, anemia, infectious disease and transplant rejection.

The MASC or their progeny home to one or more organs in the patient and are engrafted therein such that the function of a cell or organ, defective due to injury, genetic disease, acquired disease or iatrogenic treatments, is augmented, reconstituted or provided for the first time, which is surprising and unexpected. In a preferred embodiment, the injury is ischemia or inflammation.

In another preferred embodiment, the MASC or their progeny enhance angiogenesis.

In an additional aspect of the invnetion, MASC or their progeny are genetically transformed to deliver a therapeutic agent, preferably an antiangiogenic agent.

The invention provides a therapeutic composition comprising MASC and a pharmaceutically acceptable carrier, wherein the MASC are present in an amount effective to produce tissue selected from the group consisting of bone marrow, blood, spleen, liver, lung, intestinal tract, brain, immune system, bone, connective tissue, muscle, heart, blood vessels, pancreas, central nervous system, kidney, bladder, skin, epithelial appendages, breast-mammary glands, fat tissue, and mucosal surfaces including oral esophageal, vaginal and anal.

The invention further provides a therapeutic method for restoring organ, tissue or cellular function to a patient comprising the steps of removing MASC from a mammalian donor, expanding MASC to form an expanded population of undifferentiatied cells, and administering the expanded cells to the patient, wherein organ, tissue or cellular function is restored. The restored function may be enzymatic or genetic. In a preferred embodiment, the mammalian donor is the patient.

The invention provides a method of inhibiting the rejection of a heterologous MASC transplanted into a patient comprising the steps of introducing into the MASC, ex vivo, a nucleic acid sequence encoding the recipient's MHC antigen operably linked to a promotor, wherein the MHC antigen is expressed by the MASC and transplanting the MASC into the patient, wherein MHC antigen is expressed at a level sufficient to inhibit the rejection of the transplanted MASC. The patient is of the same species or another mammalian species as the donor of the MASC.

An alternative method of inhibiting the rejection of a heterologous MASC transplanted into a patient comprises transgenically knocking out expression of MHC antigen in the MASC and transplanting the transgenic MASC into the patient MHC antigen is not expressed by the MASC and rejection of the transplanted cells is inhibited.

An object of the invention is a method of generating blood or individual blood components ex vivo by the process of isolating MASC and differentiating the MASC to form blood or blood components. Preferably, the individual blood components are red blood cells, white blood cells or platelets.

Another aspect of the invention is a method of drug discovery comprising the steps of analyzing the genomic or proteomic makeup of MASC or their progeny, employing analysis thereof via bioinformatics and/or computer analysis using algorithms, and assembling and comparing new data with known databases to compare and contrast these.

A further aspect is a method of identifying the components of a differentiation pathway comprising the steps of analyzing the genomic or proteomic makeup of MASC, inducing differentiation of MASC in vitro or in vivo, analyzing the genomic or proteomic makeup of intermediary cells in the differentiation pathway, analyzing the genomic or proteomic makeup of terminally differentiated cells in the differentiation pathway, using bioinformatics and/or algorithms to characterize the genomic or proteomic makeup of MASC and their progeny, and comparing the data obtained in (e) to identify the components of the pathway. Using this method, differentiation that occurs in vitro can be compared with differentiation that occurs in vivo such that fundamental differences between the two systems can be characterized.

The invention provides a method of generating products in vitro that have therapeutic, diagnostic or research utility by identifying the products in MASC and isolating the products from MASC. In a preferred embodiment, the products are proteins, lipids, complex carbohydrates, DNA or RNA.

Included in the invention is a method of inducing, in a mammal, tolerance to an antigen administered to said mammal, the method comprising the step of administering to said mammal, after or simultaneously with the administration of said antigen, an effective amount of MASC or their progeny so that said mammal's humoral immune response to a subsequent challenge with said antigen is suppressed.

Also included is a method for removing toxins from the blood of a patient comprising contacting blood ex vivo with MASC derived cells, wherein said cells line a hollow, fiber based device. In a preferred embodiment, the cells are kidney or liver cells.

An object of the invention is a method for delivering therapeutic products to a patient comprising contacting the blood of said patient ex vivo with MASC or their progeny, wherein said MASC or their progeny are genetically transformed to deliver a therapeutic agent.

A further object is a method for testing the toxicity of a drug comprising contacting MASC or their progeny ex vivo with said drug and monitoring cell survival. In a preferred embodiment, the progeny are selected from the group consisting of hepatic, endothelial, epithelial and kidney.

BRIEF DESCRIPTION OF DRAWINGS

The following Detailed Description, given by way of example, but not intended to limit the invention to specific embodiments described, may be understood in conjunction with the accompanying drawings, incorporated herein by reference, in which.

DETAILED DESCRIPTION OF THE INVENTION

Definitions

Figure 1:
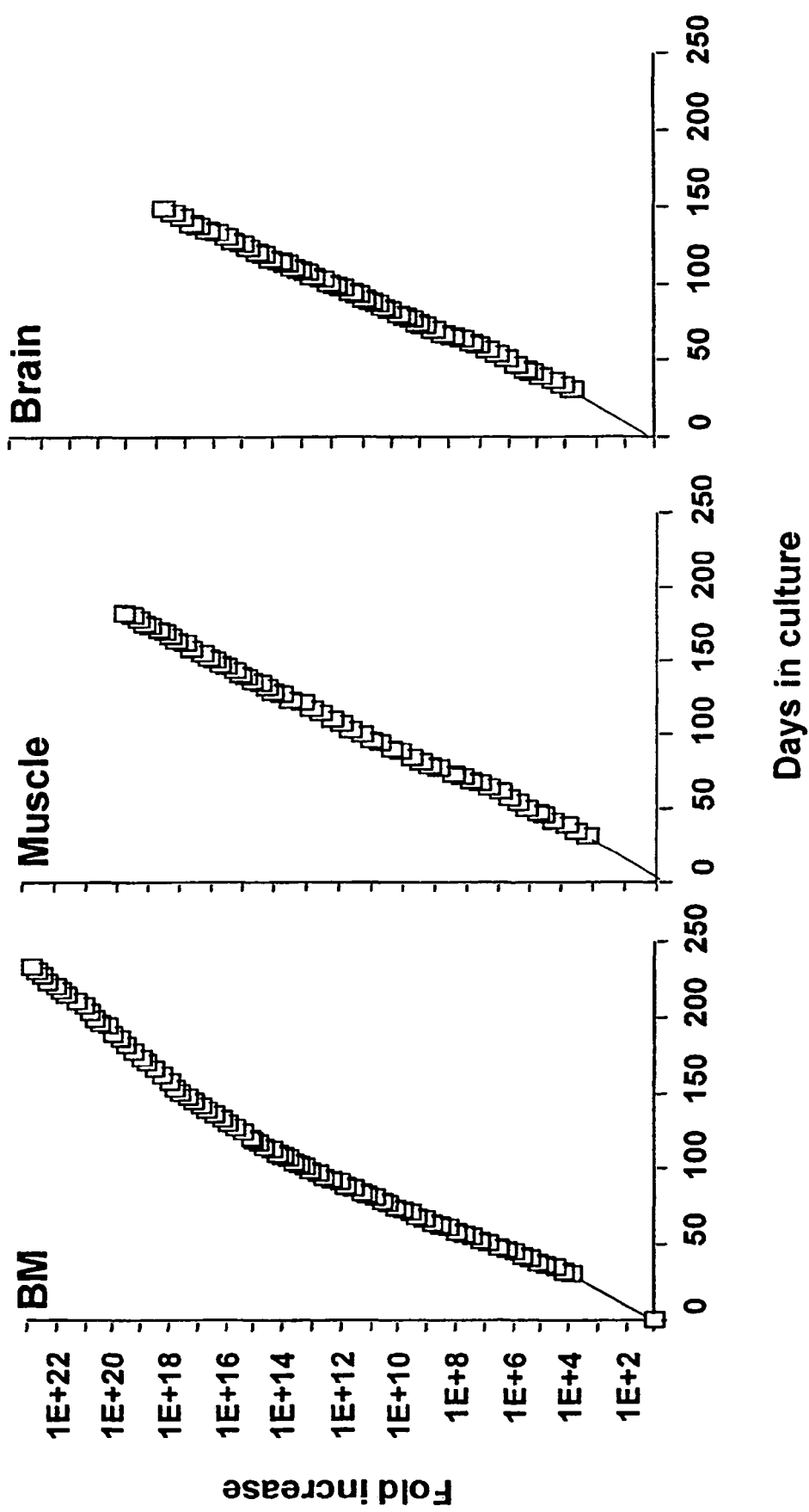
FIG. 1 shows a graphical illustration of the expansion potential of of bone marrow (BM), muscle and brain derived MASC.

As used herein, the following terms shall have the following meanings:

"Expansion" shall mean the propogation of a cell without differentiation.

"Intermediary cells" are cells produced during differentiation of a MASC that have some, but not all, of the characteristics of MASC or their terminally differentiated progeny. Intermediary cells may be progenitor cells which are committed to a specific pathway, but not to a specific cell type.

"Normal" shall mean an animal that is not diseased, mutated or malformed, i.e., healthy animals.

"Self-renewal" shall mean the ability of cells to propagate without the addition of external stimulation. The presence of cytokines or other growth factors produced locally in the tissue or organ shall not constitute external stimulation.

"Home" shall mean the ability of certain MASC or their progeny to migrate specifically to sites where additional cells may be needed.

"Knocking out expression" shall mean the elimination of the function of a particular gene.

As used herein, "genomic or proteomic makeup" shall mean the gene or protein components of a given cell.

"High levels of telomerase activity" can be correlated to the two-fold level observed in the immortal human cell line MCF7. Soule et al. (1973) J. Cancer Inst. 51:1409-1416.

Application of This Technology

MASC technology could be used to replace damaged, diseased, dysfunctional or dead cells in the body of a mammal. Furthermore these cells could be injected into the host using autologous or allogeneic cells with or without nature or artificial supports, matrices or polymers to correct for loss of cells, abnormal function or cells or organs e.g. genetic such as mutations of genes-affecting a protein function such as sickle cell disease, hemophilia or "storage diseases" where products accumulate in the body because of faulty processing, e.g. Guacher's, Neiman Pick's, mucopolysaccharidosis etc.

Examples of restitution of dying or dead cells would be the use of MASC or their differentiated progeny in the treatment of macular degeneration and other neurodegenerative diseases.

Given the ability to have these MASC to "home" to and incorporate into organs/tissues of a host animal proliferate and differentiation they could potentially be used to provide new endothelial cells to an ischemic heart and also myocardial cells themselves, numerous other examples exist.

There may be medical circumstances where transient benefits to a tissue or organs function could have desirable effects. For example, there are now cases with liver failure patients hooked up to a bioartificial liver, which was sufficient to allow for the recovery of normal liver function, obviating the need for a liver transplant. This is a serious unmet medical need, for example in one liver disease alone—hepatitis C. There are 4-5 million Americans currently infected with hepatitis C and there are estimates that 50% of these people will get cirrhosis and need a liver transplant. This is a huge public health problem that is begging for a remedy. Hepatocytes, derived from autologous or allogeneic MASC, can be transplanted in this or other liver diseases. Such transplants may either transiently provide liver function to allow recovery of the recipient's own liver cells or permanently repopulate a damaged liver to allow recovery of normal liver function via the donor cells.

In addition to many cell therapies where the undifferentiated MASC are administered to a human or other mammal to then differentiate into specific cells in the donor, the progeny of the MASC could be differentiated ex vivo and then be administered as purified or even mixtures of cells to provide a therapeutic benefit. These MASC in the undifferentiated state could also be used as carriers or vehicles to deliver drugs or molecules of therapeutic benefit. This could be to treat any one of a number of diseases including but not limited to cancer, cardiovascular, inflammatory, immunologic, infections, etc. So by example, a cell perhaps an endothelial cell expressing a novel or high levels of an angiogenic molecule could be administered to a patient which would be incorporated into existing blood vessels to promote angiogenesis, for example in the heart; correspondingly one could have endothelial cells producing molecules that might suppress angiogenesis that would be incorporated into blood cells and inhibit their further formation for example in diabetic retinopathy or in cancer where new blood vessel formation is key to the pathogenesis, spread and extent of the disease.

The ability to populate the BM and to form blood ex vivo has an untold use for important medical applications. For example regarding ex vivo production of blood, the transfusion of blood and blood products around the world is still performed with variable safety because of transmission of infectious agents. Blood transfusions have lead to HIV, hepatitis C and B, and now the impending threat of Mad Cow or CJD, Creuzfeldt-Jakob disease. The ability to produce blood in vitro, especially red blood cells, could provide a safe and reliable alternative to collection of blood from people. It might never fully replace blood collection from donors. hMASC or their hematopoietic progeny could be placed in animals in utero such as sheep which could form human hematopoietic cells and serve as a source for human blood components or proteins of therapeutic utility. The same could be true for hepatocytes, islets or many other cell types but would provide an alternative to producing human cells in vitro and use the animals as factories for the cells. It could also assist in blood shortages that are predicted to occur. hMASC could also conceivably be transplanted into a human embryo to correct any one of a number of defects.

Because these MASC can give rise to clonal populations of specifically differentiated cells they are a rich platform for drug discovery. This would involve doing gene expression, analyzing gene expression, discovery of new genes activated patterns of activation, proteomics and patterns of protein expression and modification surrounding this. This would be analyzed with bioinformatics, using data bases and algorithms for analyzing these data compared to publicly available or proprietary data bases. The information of how known drugs or agents might act could be compared to information derived from MASC, their differentiated progeny and from a population of people which could be available. Pathways, targets, and receptors could be identified. New drugs, antibodies or other compounds could be found to produce a biologically desirable responses. Correspondingly, the MASC and their differentiated progeny could be used as monitors for undesirable responses, coupled with databases, bioinformatics and algorithms.

These MASC derived from human, mouse, rat or other mammals appear to be the only normal, non-malignant, somatic cell (non germ cell) known to date to express very high levels of telomerase even in late passage cells. The telomeres are extended in MASC and they are karyotypically normal. Because MASC injected into a mammal, home to multiple organs, there is the likelihood that newly arrived MASC in a particular organ could be self renewing. As such, they have the potential to repopulate an organ not only with themselves but also with self renewing differentiated cell types that could have been damaged, died, or otherwise might have an abnormal function because of genetic or acquired disease.

For example in type I diabetes there is a progressive loss of insulin producing beta cells in the pancreatic islets. In various renal diseases there is progressive loss of function and in some cases obliteration of glomerulus. If in the case of diabetes, MASC or differentiated progeny might home to the pancreas and themselves or via interaction with endogenous cells within the pancreas, induce islets to be formed. This would have an ameliorating impact on diabetes. Ultimately conditions, agents or drugs might be found to in vivo control, i.e. promote or inhibit their self renewing capability of the MASC and control, or enhance or inhibit the movement to differentiated progeny, e.g., islet precursors, hepatocyte precursors, blood precursors, neural and/or cardiac precursors using MASC one will likely find pathways, methods of activation and control that might induce endogenous precursor cells within an organ to proliferate and differentiation.

This same ability to repopulate a cellular tissue or organ compartment and self renew and also differentiate could have numerous uses and be of unprecedented usefulness to meet profound unmet medical needs. So for example certain genetic diseases where there are enzyme deficiencies have been treated by BM transplantation. Often times this may help but not cure the complications of the disease where residual effects of the disease might persist in the brain or bones or elsewhere, MASC and genetically engineered MASC offer the hope to ameliorate numerous genetic and acquired diseases. They will also be useful for diagnostic and research purposes and drug discovery.

The present invention also provides methods for drug discovery, genomics, proteomics, and pathway identification; comprising analyzing the genomic or proteomic makeup of a MASC, coupled with analysis thereof via bioinformatics, computer analysis via algorithms, to assemble and compare new with known databases and compare and contract these. This will identify key components, pathways, new genes and/or new patterns of gene and protein expression and protein modification (proteomics) that could lead to the definition of targets for new compounds, antibodies, proteins, small molecule organic compounds, or other biologically active molecules that would have therapeutic benefit.

EXAMPLES

The following examples are provided to illustrate but not limit the invention.

Example 1

Selection, Culture and Characterization of Mouse Multipotent Adult Stem Cells (mMASC)

Cell Isolation and Expansion

All tissues were obtained according to guidelines from the University of Minnesota IACUC. BM mononuclear cells (BMMNC) were obtained by ficoll-hypaque separation of BM was obtained from 5-6 week old ROSA26 mice or C57/BL6 mice. Alternatively, muscle and brain tissue was obtained from 3-day old 129 mice. Muscles from the proximal parts of fore and hind limbs were excised from and thoroughly minced. The tissue was treated with 0.2% collagenase (Sigma Chemical Co, St Louis, Mo.) for 1 hour at 37° C., followed by 0.1% trypsin (Invitrogen, Grand Island, N.Y.) for 45 minutes. Cells were then triturated vigorously and passed through a 70-um filter. Cell suspensions were collected and centrifuged for 10 minutes at 1600 rpm. Brain tissues was dissected and minced thoroughly. Cells were dissociated by incubation with 0.1% trypsin and 0.1% DNAse (Sigma) for 30 minutes at 37° C. Cells were then triturated vigorously and passed through a 70-um filter. Cell suspension was collected and centrifuged for 10 minutes at 1600 rpm.

BMMNC or muscle or brain suspensions were plated at $1 \times 10^5/cm^2$ in expansion medium [2% FCS in low glucose Dulbecco's minimal essential medium (LG-DMEM), 10 ng/mL each platelet derived growth factor (PDGF), epidermal growth factor (EGF) and leukemia inhibitory factor (LIF)] and maintained at $5 \times 10^3/cm^2$. After 3-4 weeks, cells recovered by trypsin/EDTA were depleted of $CD45^+$/glycophorin (Gly)-$A^+$ cells with micromagnetic beads. Resulting $CD45^-$/Gly-$A^-$ cells were replated at 10 cells/well in 96-well plates coated with FN and were expanded at cell densities between 0.5 and $1.5 \times 10^3/cm^2$. The expansion potential of MASC was similar regardless of the tissue from which they were derived (FIG. 1).

Characterization of MASC

Phenotypically, mMASC derived from BM, muscle and brain and cultured on FN were $CD13^+$, $CD44^-$, $CD45^-$, class-I and class-II histocompatibility antigen$^-$, $Flk1^{low}$ and cKit$^-$, identical to the characteristics of hMASC, as described in Internation Application No. PCT/US00/21387. Although cell expansion during the initial 2-3 months was greater when cells were cultured on collagen type IV, laminin or Matrigel™, cells had phenotypic characteristics of MSC, i.e., expressed CD44 and did not express CD13. As with human cells, mMASC cultured on FN expressed transcripts for oct-4, and the LIF-R.

Approximately 1% of wells seeded with 10 $CD45^-$/Gly$A^-$ cells yielded continuous growing cultures. This suggests that the cells capable of initiating MASC cultures are rare and likely less that 1/1,000 of $CD45^-$/Gly$A^-$ cells. mMASC cultured on FN were 8-10 μm in diameter with a large nucleus and scant cytoplasm. Several populations have been cultured for >100 PDs. The morphology and phenotype of cells remained unchanged throughout culture.

mMASC that had undergone 40 and 102 PDs were harvested and telomere lengths evaluated. Telomere length was measured using the Telomere Length Assay Kit from Pharmingen (New Jersey, USA) according to the manufacturer's recommendations. Average telomere length (ATL) of mMASC cultured for 40 PDs was 27 Kb. When re-tested after 102 PDs, ATL remained unchanged. For karyotyping of mMASC, cells were subcultured at a 1:2 dilution 12 h before harvesting, collected with trypsin-EDTA, and subjected to a 1.5 h colcemid incubation followed by lysis with hypotonic KCl and fixation in acid/alcohol as previously described (Verfaillie et al., 1992). Cytogenic analysis was conducted on a monthly basis and showed a normal karyotype, except for a single population that became hyperdiploid after 45 PDs, which was no longer used for studies.

Murine MASC obtained after 46 to >80 PDs were tested by Quantitative (Q) RT-PCR for expression levels of Oct4 and Rex1, two transcription factors important in maintaining an undifferentiated status of ES cells. RNA was extracted from mouse MASC, neuroectodermal differentiated progeny (day 1-7 after addition of bFGF) and mouse ES cells. RNA was reverse transcribed and the resulting cDNA underwent 40 rounds of amplification (ABI PRISM 7700, Perkin Elmer/Applied Biosystems) with the following reaction conditions: 40 cycles of a two step PCR (95° C. for 15 seconds, 60° C. for 60 seconds) after initial denaturation (95° C. for 10 minutes) with 2 μl of DNA solution, 1× TaqMan SYBR Green Universal Mix PCR reaction buffer. Primers are listed in Table 1.

TABLE 1

| Primers used | |
|---|---|
| NEO | 5'-TGGATTGCACGCAGGTTCT-3'<br>5'-TTCGCTTGGTGGTCGAATG-3' |
| Oct4 | 5'-GAAGCGTTTCTCCCTGGATT-3'<br>5'-GTGTAGGATTGGGTGCGTT-3' |
| Rex 1 | 5'-GAAGCGTTCTCCCTGGAATTTC-3'<br>5'-GTGTAGGATTGGGTGCGTTT-3' |
| otx 1 | 5'-GCTGTTCGCAAAGACTCGCTAC-3'<br>5'-ATGGCTCTGGCACTGATACGGATG-3' |
| otx2 | 5'-CCATGACCTATACTCAGGCTTCAGG-3'<br>5'-GAAGCTCCATATCCCTGGGTGGAAAG-3' |
| Nestin 5' | 5'-GGAGTGTCGCTfAGAGGTGC-3'<br>5'-TCCAGAAAGCCAAGAGAAGC-3' | mRNA levels were normalized using GAPDH as housekeeping gene, and compared with levels in mouse ES cells. Oct4 and Rex 1 mRNA were present at similar levels in BM, muscle and brain derived MASC. Rex1 mRNA levels were similar in mMASC and mES cells, while Oct4 mRNA levels were about 1,000 fold lower in MASC than in ES cells.

Figure 2:
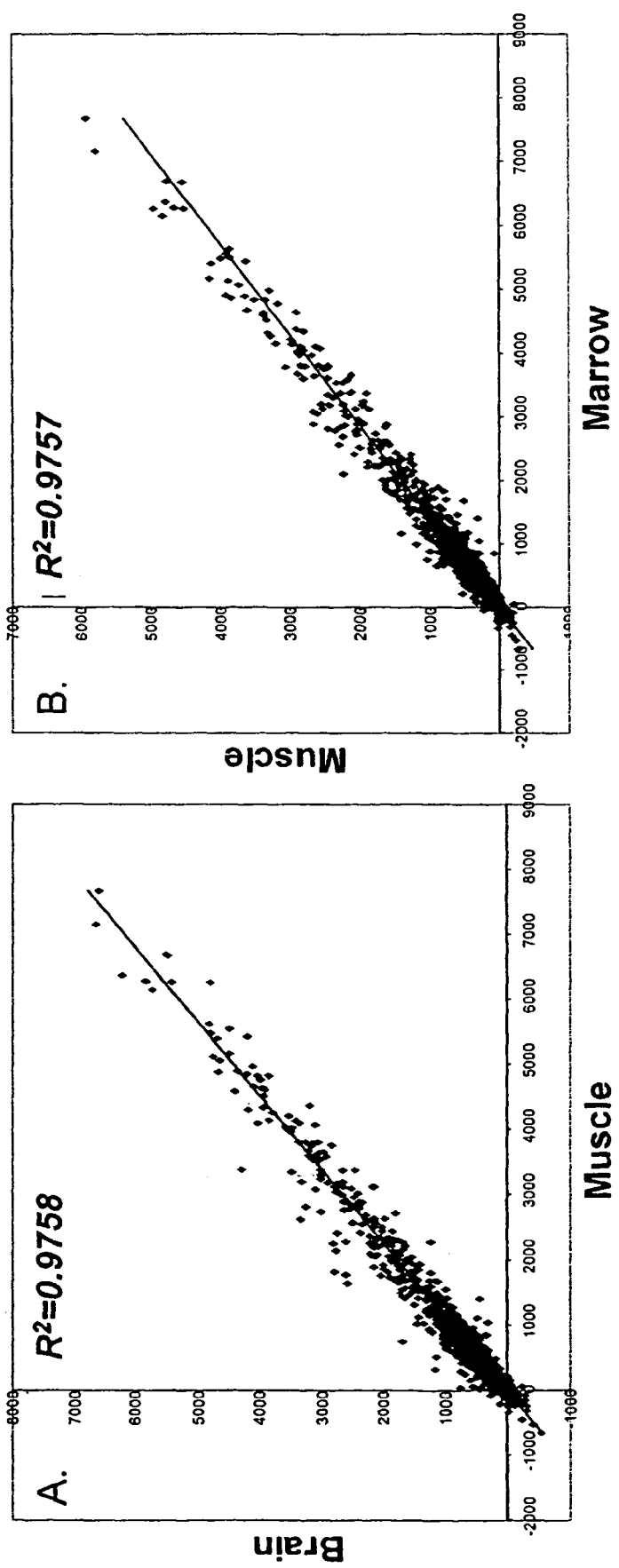
FIG. 2 shows a scatter plot representing gene expression in (A) muscle and brain MASC and (B) bone marrow and muscle MASC.

Expressed Gene Profile of Mouse BM, Muscle and Brain Derived MASC is Highly Similar To further evaluate whether MASC derived from different tissues were similar, the expressed gene profile of BM, muscle and brain derived MASC was examined using U74A Affimetrix gene array. Briefly, mRNA was extracted from $2\text{-}3 \times 10^6$ BM, muscle or brain derived-MASC, cultured for 45 population doublings. Preparation of cDNA, hybridization to the U74A array containing 6,000 murine genes and 6,000 EST clusters, and data acquisition were done per manufacturer's recommendations (all from Affimetrix, Santa Clara, Calif.). Data analysis was done using GeneChip® software (Affimetrix). Increased or decreased expression by a factor of 2.2 fold (Iyer V. R. et al., 1999; Scherf U. et al., 2000; Alizadeh A. A. et al., 2000) was considered significant. $r^2$ value was determined using linear regression analysis (FIG. 2).

Comparison between the expressed gene profile in MASC from the three tissues showed that <1% of genes were expressed at >2.2-fold different levels in MASC from BM than muscle. Likewise, only <1% of genes were expressed >2.2-fold different level in BM than brain derived MASC. As the correlation coefficient between the different MASC populations was >0.975, it was concluded that MASC derived from the different tissues are highly homologous, in line with the phenotypic described above and the differentiation characteristics described in Example 5.

Using the mouse-specific culture conditions, mMASC cultures have been maintained for more than 100 cell doublings. mMASC cultures have been initiated with marrow from C57B1/6 mice, ROSA26 mice and C57BL/6 mice transgenic for the -HMG-LacZ.

Example 2

Selection and Culture of Rat Multipotent Adult Stem Cells (rMASC)

BM and MNC from Sprague Dawley or Wistar rats were obtained and plated under conditions similar for mMASC. After 21-28 days, cells were depleted of $CD45^+$ cells, and the resulting $CD45^-$ cells were subcultured at 10 cells/well.

Similar to mMASC, rMASC have been culture expanded for >100 PDs. Expansion conditions of rat MASC culture required the addition of EGF, PDGF-BB and LIF and culture on FN, but not collagen type 1, laminin or Matrigel™. rMASC were CD44, CD45 and MHC class I and II negative, and expressed high levels of telomerase. The ability of a normal cell to grow over 100 cell doublings is unprecedented, unexpected and goes against conventional dogma of more than two decades.

Rat MASC that had undergone 42 PDs, 72 PDs, 80 PDs, and 100 PDs, were harvested and telomere lengths evaluated. Telomeres did not shorten in culture, as was determined by Southern blot analysis after 42 PDs, 72 PDs, 80 PDs, and 100 PDs. Monthly cytogenetic analysis of rat MASC revealed normal karyotype.

Example 3

Selection and Culture of Human Multipotent Adult Stem Cells (hMASC)

BM was obtained from healthy volunteer donors (age 2-50 years) after informed consent using guidelines from the University of Minnesota Committee on the use of Human Subject in Research. BMMNC were obtained by Ficoll-Paque density gradient centrifugation and depleted of $CD45^+$ and glycophorin-$A^+$ cells using micromagnetic beads (Miltenyii Biotec, Sunnyvale, Calif.).

Expansion conditions: $5 \times 10^3$ $CD45^-$/$GlyA^-$ cells were diluted in 200 μL expansion medium [58% DMEM-LG, 40% MCDB-201 (Sigma Chemical Co, St Louis, Mo.), supplemented with 1× insulin-transferrin-selenium (ITS), 1× linoleic-acid bovine serum albumin (LA-BSA), $10^{-8}$ M Dexamethasone, $10^{-4}$ M ascorbic acid 2-phosphate (all from Sigma), 100 U penicillin and 1,000 U streptomycin (Gibco)] and 0-10% fetal calf serum (FCS) (Hyclone Laboratories, Logan, Utah) with 10 ng/ml of EGF (Sigma) and 10 ng/ml of PDGF-BB (R&D Systems, Minneapolis, Minn.)] and plated in wells of 96 well plates that had been coated with 5 ng/ml of FN (Sigma). Medium was exchanged every 4-6 days. Once wells were >40-50% confluent, adherent cells were detached with 0.25% trypsin-EDTA (Sigma) and replated at 1:4 dilution in MASC expansion medium and bigger culture vessels coated with 5 ng/ml FN to maintain cell densities between 2 and $8 \times 10^3$ cells/$cm^2$.

Figure 3:
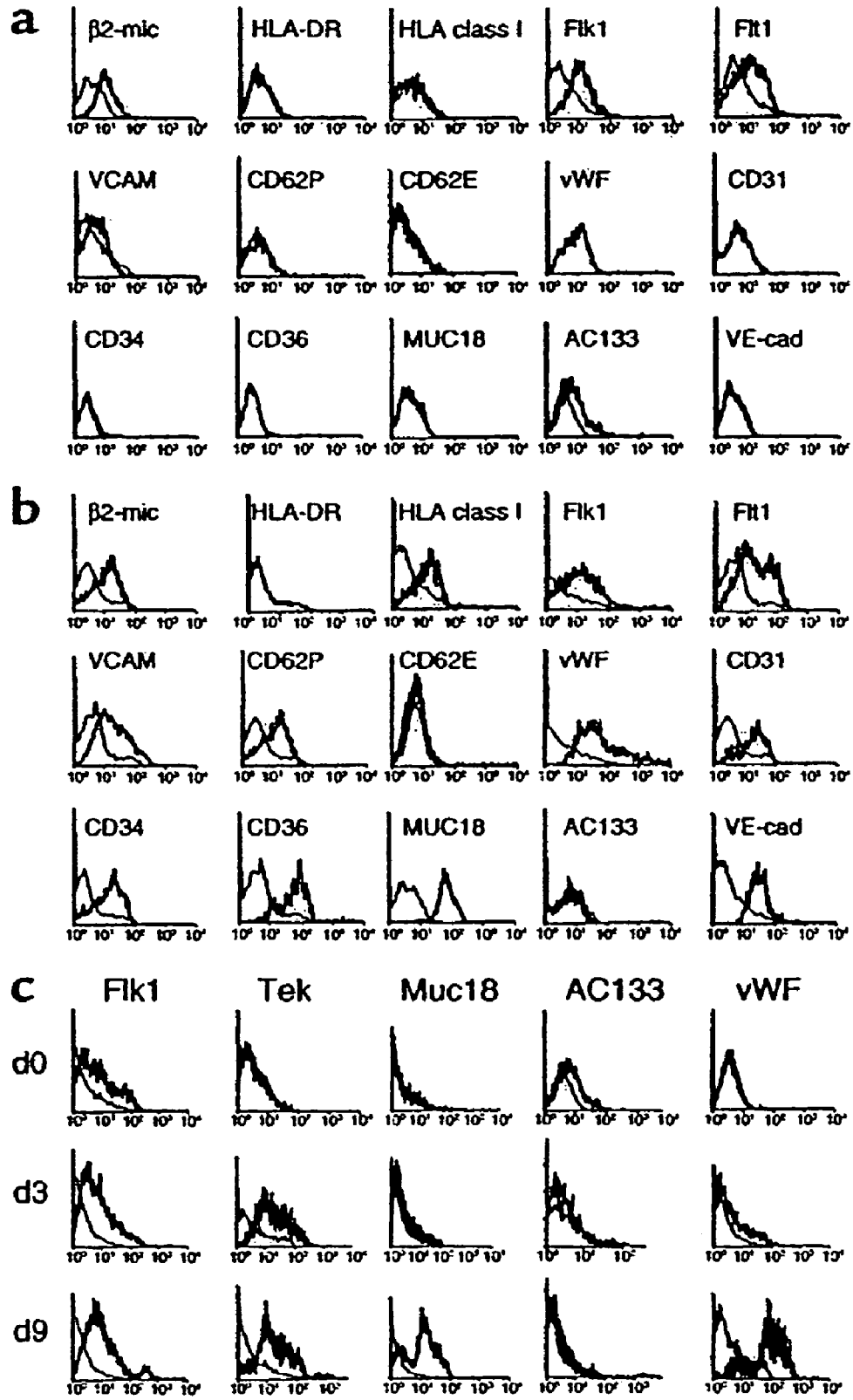
FIG. 3 shows a graphical illustration of FACS analysis of undifferentiated MASC and MASC cultured with VEGF. The plots show isotype control IgG staining profile (thin line) vs. specific antibody staining profile (thick line). Panel A shows the phenotype of undifferentiated MASC. MASC express low levels of $\beta$2-microglobulin, Flk1, Fit1 and AC 133, but do not stain with any of the other anti-endothelial markers; panel B shows the phenotype of MASC cultured for 14 days with 10 ng/mL VEGF. MASC express low levels most markers associated with endothelial cells, but lost expression of AC 133; and panel C shows phenotype of MASC cultured or 3-9 days with 10 ng/mL VEGF. MASC lose expression of AC 133 by day 3 of culture with VEGF, acquire expression of Tek and VE-cadherin by day 3, Tie, vWF, CD34 and HIP12 by day 9.

Undifferentiated MASC did not express CD31, CD34, CD36, CD44, CD45, CD62-E, CD62-L, CD62-P, HLA-class I and II, cKit, Tie, Tek, $\alpha_v\beta_3$, VE-cadherin, vascular cell adhesion molecule (VCAM), intracellular adhesion molecule (ICAM)-1. MASC expressed low/very low levels of β2-microglobulin, $\alpha_v\beta_5$, CDw90, AC133, Flk1 and Fit1, and high levels of CD13 and CD49b (FIG. 3).

Example 4

Immunophenotypic Analysis

Immunofluorescence

1. Cultured cells were fixed with 4% paraformaldehyde and methanol at room temperature, and incubated sequentially for 30 min each with primary antibody, and with or without secondary antibody. Between steps, slides were washed with PBS/BSA. Cells were examined by fluorescence microscopy (Zeiss Axiovert; Carl Zeiss, Inc., Thornwood, N.Y.) and confocal fluorescence microscopy (Confocal 1024 microscope; Olympus AX70, Olympus Optical Co. LTD, Japan). To assess the frequency of different cell types in a given culture, the number of cells were counted that stained positive with a given antibody in four visual fields (50-200 cells per field).

2. Harvested tissues: Cytospin specimens of blood and BM were fixed with acetone (Fisher Chemicals) for 10 min at room temperature. For solid organs, 5 μm thick fresh frozen sections of tissues were mounted on glass slides and immediately fixed in acetone for 10 min at room temperature. Following incubation with isotype sera for 20 min, cytospin preparations or tissue sections were serially stained for tissue specific antigens, β-gal and a nuclear counter stain (DAPI or TO-PRO-3). Cover slips were mounted using Slowfade-antifade kit (Molecular Probes Inc., Eugene, Oreg., USA). Slides were examined by fluorescence microscopy and confocal fluorescence microscopy.

3. Antibodies: Cells were fixed with 4% paraformaldehyde at room temperature or methanol at −20° C., and incubated sequentially for 30 min each with primary Ab, and FITC or Cy3 coupled anti-mouse- or anti-rabbit-IgG Ab. Between each step slides were washed with PBS+1% BSA. PE or FITC-coupled anti-CD45, anti-CD31, anti-CD62E, anti-Mac1, anti-Gr1, anti-CD19, anti-CD3, and anti-Ter119 antibodies were obtained from BD Pharmingen. Abs against GFAP (clone G-A-5, 1:400), galactocerebroside (GalC) (polyclonal, 1:50), MBP (polyclonal, 1:50), GABA (clone GB-69, 1:100), parvalbumin (clone PARV-19, 1:2000), TuJI (clone SDL.3D 10, 1:400), NF-68 (clone NR4, 1:400), NF-160 (clone NN 18, 1:40), and NF-200 (clone N52, 1:400), NSE (polyclonal, 1:50), MAP2-AB (clone AP20, 1:400), Tau (polyclonal, 1:400), TH (clone TH-2, 1:1000), DDC (clone DDC-109, 1:100), TrH (clone WH-3, 1:1000), serotonin (polyclonal, 1:2000), glutamate (clone GLU-4, 1:400), fast twitch myosin (clone MY-32; 1:400 dilution) were from Sigma. DAPI and TOPRO-3 were from Molecular Probes. Abs against vWF (polyclonal; 1:50) Neuro-D (polyclonal, 1:50), c-ret (polyclonal, 1:50) and Nurrl (polyclonal, 1:50)

were from Santa Cruz Biotechnology Inc., Santa Cruz, Calif. Abs against PSA-NCAM (polyclonal, 1:500) from Phanmingen, San Diego, Calif. and against serotonin transporter (clone MAB 1564, 1:400), DTP (polyclonal, 1:200), Na-gated voltage channel (polyclonal, 1:100), glutamate-receptors-5, -6 and -7 (clone 3711:500) and NMDA (polyclonal 1:400) receptor from Chemicon International, Temecula, Calif. Anti-nestin (1:400) Abs were a kind gift from Dr. U. Lendahl, University of Lund, Sweden. Antibodies against NSE (1:50) pan-cytokeratin (catalog number C-2562; 1:100), CK-18 (C-8541; 1:300), albumin (A-6684; 1:100) were all obtained from Sigma. Polyclonal antibodies against Flk1, Flt1, Tek, HNF-1β were obtained from Santa Cruz Biotechnology Inc., Santa Cruz, Calif. Anti-nestin (1:400) antibodies were a kind gift from Dr. U. Lendahl, University of Lund, Sweden. Control-mouse, -rabbit or, -rat IgGs and FITC/PE/Cy3- and Cy5-labeled secondary antibodies were obtained from Sigma. Rabbit anti-β-gal-FITC antibody was obtained from Rockland Immunochemicals, USA. TO-PRO-3 was obtained from Molecular Probes Inc. and DAPI was obtained from Sigma.

B. X-GAL staining: Tissue sections were stained by for β-galactosidase enzyme activity using β-gal staining kit from Invitrogen, pH 7.4. Manufacturer's instructions were followed except for the fixation step, during which the tissue sections were incubated for 5 min instead of 10 min.

C. FACS: For FACS, undifferentiated MASC were detached and stained sequentially with anti-CD44, CD45, CD13, cKit, MHC-class I and II, or b2-microglobulin (BD Pharmingen) and secondary FITC or PE coupled antibodies, fixed with 2% paraformaldehyde until analysis using a FACS-Calibur (Becton-Dickinson).

Example 5

Single Cell Origin of Differentiated Lineages from MASC

The differentiation ability of mMASC or rMASC was tested by adding differentiation factors (cytokines) chosen based on what has been described for differentiation of hMASC or ES cells to mesoderm, neuroectoderm, and endodern. Differentiation required that cells were replated at $1$-$2\times10^4$ cells/cm$^2$ in serum free medium, without EGF, PDGF-BB and LIF, but with lineage specific cytokines. Differentiation was determined by immunohistology for tissue specific markers [slow twitch myosin and MyoD (muscle), von-Willebrand factor (vWF) and Tek (endothelium), NF200 and MAP2 (neuroectodermal), and cytokeratin-18 and albumin (endodermal)], RT-PCR, and functional studies.

MASC Differentiation into Neuroectodermal Cells

Palmer et al. showed that neuroprogenitors can be culture expanded with PDGF-BB and induced to differentiate by removal of PDGF and addition of bFGF as a differentiation factor. Based on those studies and studies conducted using hMASC, mMASC and rMASC were plated in FN coated wells without PDGF-BB and EGF but with 100 ng/mL bFGF. Progressive maturation of neuron-like cells was seen throughout culture. After 7 days, the majority of cells expressed nestin. After 14 days, 15-20% of MASC acquired morphologic and phenotypic characteristics of astrocytes (GFAP$^+$), 15-20% of oligodendrocytes (galactocerebroside (GalC)$^+$) and 50-60% of neurons (neurofilament-200 (NF-200)$^+$). NF200, GFAP or GalC were never found in the same cell, suggesting that it is unlikely that neuron-like cells were hMASC or glial cells that inappropriately expressed neuronal markers. Neuron-like cells also expressed Tau, MAP2 and NSE. Approximately 50% of neurons expressed gamma-amino-butyric-acid (GABA) and parvalbumin, 30% tyrosine hydroxylase and dopa-decarboxylase (DDC), and 20% serotonin and tryptophan hydroxylase. Differentiation was similar when MASC had been expanded for 40 or >90 PDs. Q-RT-PCR, performed as described in Example 1, confirmed expression of neuroectodermal markers: on day 2 MASC expressed otx1 and otx2 mRNA, and after 7 days nestin mRNA was detected.

The effect of fibroblast growth factor (FGF)-8b as a differentiation factor was tested next. This is important in vivo for midbrain development and used in vitro to induce dopaminergic and serotoninergic neurons from murine ES cells on hMASC. When confluent hMASC (n=8) were cultured with 10 ng/mL FGF-8b+EGF, differentiation into cells staining positive for neuronal markers but not oligodendrocytes and astrocytes was seen. Neurons had characteristics of GABAergic (GABA$^+$; 40±4%), dopaminergic (DOPA, TH, DCC and DTP$^+$, 26±5%) and serotoninergic (TrH, serotonin and serotonin-transporter$^+$, 34±6%) neurons. DOPA$^+$ neurons stained with Abs against NurrI suggesting differentiation to midbrain DA neurons. FGF-8b induced neurons did not have electro-physiological characteristics of mature neurons. Therefore, cocultured cells from 3-week old FGF-8b supported cultures with the glioblastoma cell line, U-87, and FGF-8b for an additional 2-3 weeks.

Neurons acquired a more mature morphology with increased cell size and number, length and complexity of the neurites, and acquired electrophysiological characteristics of mature neurons (a transient inward current, blocked reversibly by 1 μM tetrodotoxin (TTX) together with the transient time course and the voltage-dependent activation of the inward current is typical for voltage-activated sodium currents, found only in mature neurons).

When hMASC (n=13) were cultured with 10 ng/m brain-derived neurotrophic factor (BDNF)+EGF, differentiation was to exclusively DOPA, TH, DCC, DTP and Nurrl positive neurons. Although BDNF supports neural differentiation from ES cells and NSC (Peault, 1996; Choi et al. 1998), no studies have shown exclusive differentiation to DA-like neurons.

Similar results were seen for mMASC induced with bFGF and rMASC with bFGF and BDNF. Further studies on MASC-derived neuronal cells are presented in Example 10.

MASC Differentiation into Endothelial Cells

As an example of mesoderm, differentiation was induced to endothelium. Undifferentiated mMASC or rMASC did not express the endothelial markers CD31, CD62E, Tek or vWF, but expressed low levels of Flk1. mMASC or rMASC were cultured in FN-coated wells with 10 ng/mL of the endothelial differentiation factor VEGF-B. Following treatment with VEGF for 14 days, >90% of MASC, irrespective of the number of PDs they had undergone, expressed Flt1, CD31, vWF or CD62, consistent with endothelial differentiation. Like primary endothelial cells, MASC-derived endothelial cells formed vascular tubes within 6 hours after replating in Matrigel™.

Similarly, hMASC express Flk1 and Flt1 but not CD34, Muc18 (P1H12), PECAM, E- and P-selectin, CD36, or Tie/Tek. When hMASC $2\times10^4$ cells/cm$^2$ were cultured in serum free medium with 20 ng/mL vascular endothelial growth factor (VEGF), cells expressed CD34, VE-cadherin, VCAM and Muc-18 from day 7 on. On day 14, they also expressed Tie, Tek, Flk1 and Flt1, PECAM, P-selectin and E-selectin, CD36, vWF, and connexin-40. Furthermore, cells could uptake low-density lipoproteins (LDL). Results from the histochemical staining were confirmed by Western blot. To induce vascular tube formation, MASC cultured for 14 days with VEGF were replated on Matrigel™ with 10 ng/mL VEGF-B for 6 h. Endothelial differentiation was not seen when hMASC cultured in >2% FCS were used. In addition, when FCS was left in the media during differentiation, no endothelial cells were generated.

At least 1000-fold expansion was obtained when hMASC were sub-cultured, suggesting that endothelial precursors generated from hMASC continue to have significant proliferative potential. Cell expansion was even greater when FCS was added to the cultures after day 7.

When hMASC derived endothelial cells were administered intravenously (I.V.) in NOD-SCI mice who have a human colon-carcinoma implanted under the skin, contribution of the human endothelial cells could be seen to the neovascularization in the tumors. It may therefore be possible to incorporate genetically modified endothelial cells to derive a therapeutic benefit, i.e., to inhibit angiogenesis in for example cancer or to promote it to enhance vascularization in limbs or other organs such as the heart. Further studies on MASC-derived endothelial cells are presented in Example 9.

MASC Differentiation into Endoderm

Whether mMASC or rMASC could differentiate to endodermal cells was tested. A number of different culture conditions were tested including culture with the diffentiation factors keratinocyte growth factor (KGF), hepatocyte growth factor (HGF) and FGF-4, either on laminin, collagen, FN or Matrigel™ coated wells. When re-plated on Matrigel™ with 10 ng/mL FGF4+10 ng/mL HGF, approximately 70% of MASC acquired morphologic and phenotypic characteristics of hepatocyte-like cells. Cells became epithelioid, approximately 10% of cells became binucleated, and about 70% of cells stained positive for albumin, cytokeratin (CK)-18, and HNF-1P.

Endodermal-like cells generated in FGF4 and HGF containing cultures also had functional characteristics of hepatocytes, determined by measuring urea levels in supernatants of undifferentiated MASC and FGF4 and HGF-induced MASC using the Sigma Urea Nitrogen Kit 640 according to the manufacturer's recommendations. No urea was detected in undifferentiated MASC cultures. Urea production was 10 μg/cell/hr 14 days after adding FGF4 and HGF and remained detectable at similar levels until day 25. This is comparable to primary rat hepatocytes grown in monolayer. Presence of albumin together with urea production supports the notion of hepatic differentiation from MASC in vitro. Further studies on MASC-derived hepatocytes are presented in Example 11.

Given the likely existence of an endodermal lineage precursor cell, MASC likely give rise to a cell that forms various cells in the liver in the pancreas both exocrine and endocrine components and other endodermal derived cell tissue lineages.

MASC derived from muscle or brain were induced to differentiate to mesoderm (endothelial cells), neuroectoderm (astrocytes and neurons) and endoderm (hepatocyte-like cells) using the methods described above for BM-derived MASC.

Transduction

To demonstrate that differentiated cells were single cell derived and MASC are indeed "clonal" multipotent cells, cultures were made in which MASC had been transduced with a retroviral vector and undifferentiated cells and their progeny were found to have the retrovirus inserted in the same site in the genome.

Studies were done using two independently derived ROSA26 MASC, two C57BL/6 MASC and one rMASC population expanded for 40 to >90PDs, as well as with the eGFP transduced "clonal" mouse and "clonal" rMASC. No differences were seen between eGFP transduced and untransduced cells. Of note, eGFP expression persisted in differentiated MASC.

Specifically, murine and rat BMMNC cultured on FN with EGF, PDGF-BB and LIF for three weeks were transduced on two sequential days with an eGFP oncoretroviral vector. Afterwards, CD45$^+$ and GlyA$^+$ cells were depleted and cells sub-cultured at 10 cells/well. eGFP-transduced rat BMMNC were expanded for 85 PDs. Alternatively, mouse MASC expanded for 80 PDS were used. Subcultures of undifferentiated MASC were generated by plating 100 MASC from cultures maintained for 75 PDs and re-expanding them to >5×10$^6$ cells. Expanded MASC were induced to differentiate in vitro to endothelium, neuroectoderm and endoderm. Lineage differentiation was shown by staining with antibodies specific for these cell types, as described in Example 4.

Single Cell Origin of Mesodermal and Neuroectodermal Progeny

To prove single cell origin of mesodermal and neuroectodermal differentiated progeny retroviral marking was used (Jordan et al., 1990; Nolta et al., 1996). A fraction of hMASC obtained after 20 PDs was transduced with an MFG-eGFP retrovirus. eGFP$^+$ hMASC were diluted in non-transduced MASC from the same donors to obtain a final concentration of 5% transduced cells. These mixtures were plated at 100 cells/well and culture expanded until >2×10$^7$ cells were obtained. 5×10$^6$ MASC each were induced to differentiate to skeletal myoblasts, endothelium and neuroectodermal lineages. After 14 days under differentiation conditions, cells were harvested and used to identify the retroviral integration site and co-expression of eGFP and neuroectodermal, muscle and endothelial markers.

For myoblast differentiation, hMASC were plated at 2×10$^4$ cells/cm$^2$ in 2% FCS, EGF and PDGF containing expansion medium and treated with 3 μM 5-azacytidine in the same medium for 24 h. Afterwards, cells were maintained in expansion medium with 2% FCS, EGF and PDGF-BB. For endothelial differentiation, hMASC were replated at 2×1 04 cells/cm$^2$ in serum-free expansion medium without EGF and PDGF but with 10 ng/ml VEGF-B for 14 days.

Immunofluorescence evaluation showed that 5-10% of cells in cultures induced to differentiate with 5-azacytidine stained positive for eGFP and skeletal actin, 5-10% of cells induced to differentiate to endothelium costained for eGFP and vWF, and 5-10% of cells induced to differentiate to neuroectoderm costained for eGFP and either NF-200, GFAP or MBP. To define the retroviral insertion site, the host genomic flanking region in MASC and differentiated progeny was sequenced. The number of retroviral inserts in the different populations was between one and seven. As shown in Table 2, a single, identical sequence flanking the retroviral insert in muscle, endothelium and neuroectodermal cells in population A16 that mapped to chromosome 7 was identified.

TABLE 2

Single cell origin of endothelium, muscle and neuroectodermal cells

Sequence: 3'-LTR-*ccaaatt*

| Clone | Sequence |
|---|---|
| Clone A16 (Chrom. 7) | TAG CGGCCGCTTG AATTCGAACG CGAGACTACT GTGACTCACA CT |
| 5-Azacytidine | TAG CGGCCGCTTG AATTCGAACG CGAGACTACT GTGACTCACA CT |
| VEGF | TAG CGGCCGCTTG AATTCGAACG CGAGACTACT GTGACTCACA CT |
| bFGF | TAG CGGCCGCTTG AATTCGAACG CGAGACTACT GTGACTCACA CT |
| Clone A12-A (Chrom. 9) | ATTTATA TTCTAGTTTAT TTGTGTTTGGG GCAGACGAGG |
| 5-Azacytidine | ATTTATA TTCTAGTTTAT TTGTGTTTGGG GCAGACGAGG |
| VEGF | ATTTATA TTCTAGTTTAT TTGTGTTTGGG GCAGACGAGG |
| bFGF | ATTTATA TTCTAGTTTAT TTGTGTTTGGG GCAGACGAGG |
| Clone A12-A (Chrom. 12) | TCCTGTCTCA TTCAAGCCAC ATCAGTTACA TCTGCATTTT |
| 5-Azacytidine | TCCTGTCTCA TTCAAGCCAC ATCAGTTACA TCTGCATTTT |
| VEGF | TCCTGTCTCA TTCAAGCCAC ATCAGTTACA TCTGCATTTT |
| bFGF | TCCTGTCTCA TTCAAGCCAC ATCAGTTACA TCTGCATTTT |

Primers specific for the 3' LTR were designed and for the flanking genomic sequence are shown in Table 3 and using Real-time PCR, it was confirmed that the retroviral insert site was identical in undifferentiated and differentiated cells. These results proved that the flanking sequence and the eGFP DNA sequence was present in similar quantities. Clone A12 contained two retroviral inserts, located on chromosome 1 and 7 respectively, and both flanking sequences could be detected not only in hMASC but also muscle, endothelium and neuroectodermal lineages. To determine whether this represented progeny of a single cell with two retroviral integrants or progeny of two cells, Real-Time PCR was used to compare the relative amount of the chromosome 1 and 7 flanking sequence to eGFP. It was found that similar amounts of both flanking regions were present in hMASC, muscle, endothelium and neuroectodermal cells, suggesting that a single cell with two retroviral inserts was likely responsible for the eGFP positive hMASC and differentiated progeny. In the other populations containing 3 or more retroviral inserts we were not able to determine whether the inserts were due to multiple insertion sites in a single cells or multiple cells contributing to the eGFP positive fraction. Nevertheless, our finding that in 2 populations, progeny differentiated into muscle, endothelium and neuroectoderm are derived from a single BM derived progenitor cell definitively proves for the first time that primitive cells can be cultured from BM that differentiate at the single cell level in cells of mesodermal lineage as well as the three different lineages of the neuroectoderm.

TABLE 3

Flanking regions and primers

| Clone | Genomic sequence |
|---|---|
| Rat flanking sequence | GATCCTTGGGAGGGTCTCCTCAGATTGATTGACTGCCCACCT CGGGGGTCTTTCAAAGTAACTCCAAAAGAAGAATGGGTTGTTAGTTAT TAAACGGTTCTTAGTAAAGTTTTGGTTTTGGGAATCACAGTAACAACT CACATCAC*AACTCCAATCGTTCCGTGAAA* |
| Mouse flanking sequence | CATCCTTGGGAGGGTCTCCTCAGATTGATTGACTGCCCATAAGTTA TAAGCTGGCATGACTGTGT*TGCTAAGGACACTGGTGAAAGC* |

Bold: MSCV LTR;
Bold and underlined: MSCV LTR primer used for Q-PCR
*Italics and underlined*: Flanking sequence primers used for Q-PCR.

Example 6

Homing and Engraftment of Mammalian MASC into Numerous Organs in the Body mMASC were tested to determine whether they had the ability to engraft and differentiate in vivo into tissue specific cells. mMASC were grown as described in Example 1 from a LacZ transgenic C57 Black 6, ROSA 26 mouse. $10^6$ mMASC from the LacZ mouse were I.V. injected into NOD-SCID mice tail veins with or without 250 Rads of total body radiation 4-6 hrs prior to the injection. The animals were sacrificed by cervical dislocation at 4-24 weeks after the injections.

Tissue Harvest

Blood and bone marrow: 0.5-1 ml of blood was obtained at the time animals were sacrificed. BM was collected by flushing femurs and tibias. For phenotyping, red cells in blood and BM were depleted using ice cold ammonium chloride (Stem Cell Technologies Inc., Vancouver, Canada) and $10^5$ cells used for cytospin centrifugation. For serial transplantation, $5 \times 10^7$ cells from 2 femurs and 2 tibias were transplanted into individual secondary recipients via tail vein injection. Secondary recipients were sacrificed after 7-10 weeks.

Solid organs: Lungs were inflated with 1 ml 1:4 dilution of OCT compound (Sakura-Finetek Inc, USA) in PBS. Specimens of spleen, liver, lung, intestine, skeletal muscle, myocardium, kidney and brain of the recipient animals were harvested and cryopreserved in OCT at −80° C. and in RNA Later (Ambion Inc., Austin, Tex., USA) at −20° C. for quantitative PCR.

mMASC Engraft and Differentiate in Tissue Specific Cells In Vivo

Engraftment of the β-gal/neomycin (NEO) transgene-containing cells (Zambrowicz et al., 1997) was tested by immunohistochemistry for β-gal and by Q-PCR for NEO. Immunohistochemistry and Q-PCR were performed as described in Examples 5 and 1 respectively. Primers are listed in Table 1.

Figure 4:
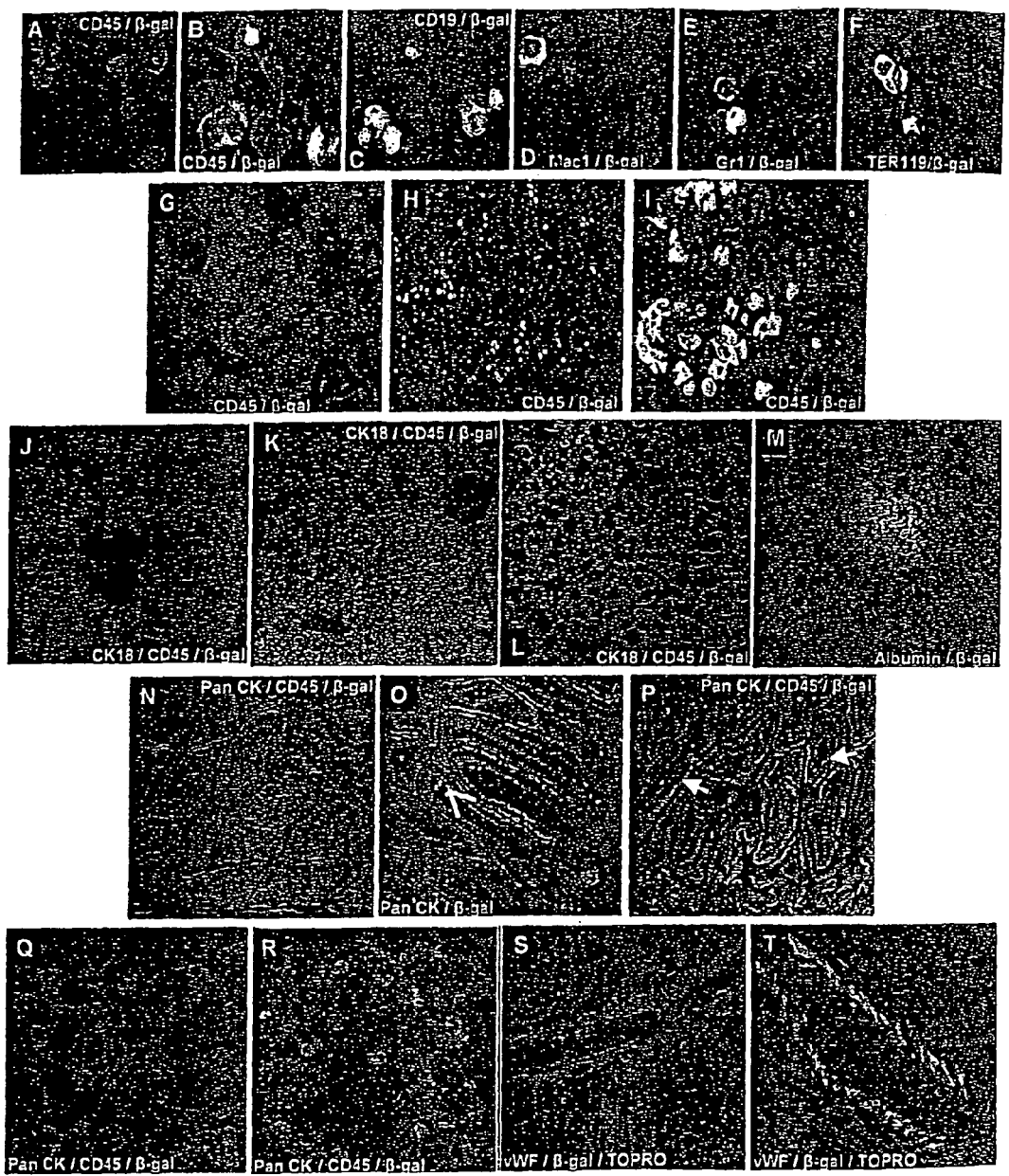
FIG. 4 shows a photomicrograph of engraftment and in vivo differentiation of mMASC. Slides were examined by fluorescence or confocal microscopy. Panels A, G, J, N, Q and S represent identically stained tissues of control NOD-SCID animals that were not injected with mMASC. Panels A-F show a photomicrograph of bone marrow (BM) cytospin from a control (A) and study (B-F) animal stained with anti$\beta$-gal-FITC antibody and PE-conjugated antibodies to various hematopoietic antigens. A-B: CD45, C: CD19, D: MAC1, E: GR1, F: TER119 and DAPI; panels G-I shows a photomicrograph of a spleen section from a control (G) and study animal (H, I) stained with anti-$\beta$-gal-FITC antibody and anti-CD45-PE antibody. Donor derived anti-$\beta$-gal$^+$ cells are seen in clusters. H is 10× and I are 60× magnifications; panels J-M shows a photomicrograph of a liver section from a control mouse (J) and study animal (K-M) stained with anti-$\beta$-gal-FITC. J-L are co-stained with mouse-anti-CK-18/anti-mouse-Cy5 plus CD45-PE and M with mouse anti-albumin/anti-mouse Cy3 antibodies. J-K, L and M are 20×, 60× and 10× magnifications respectively; panels N-P show a photomicrograph of an intestine section from a control mouse and study animal (O-P), stained with anti-$\beta$-gal-FITC plus mouse-anti-pan-CK/anti-mouse-Cy5 antibodies (N-P). N and P are costained with CD45-PE antibodies. $\beta$-gal$^+$ Pan-CK$^+$CD45$^-$ epithelial cells covered 50% (solid arrow, panel P) of the circumference of villi. Pan-CK$^-$/$\beta$-gal$^+$ cells in the core of the villi (open arrow-panel O) co-stained for CD45 (P); panels Q-R show a photomicrograph of a lung section from a control mouse (O) and study animal (R) stained with anti-$\beta$-gal-FITC plus mouse-anti-pan-CK/anti-mouse-Cy5 plus CD45-PE antibodies. Several $\beta$-gal$^+$ pan-CK$^+$ donor cells are seen lining the alveoli of the recipient animal (R). CD45$^+$/pan-CK$^-$ cells of hematopoietic origin are seen distinctly from the epithelial cells; and panels S-t show a photomicrograph of a blood vessel section from a control mouse (S) and thymic lymphoma that developed in a study animal 16 weeks after transplantation (T) stained with anti-β-gal-FITC, anti-vWF-PE and TO-PRO3. β-gal+donor cells differentiated into vWF+endothelial cells in the thymic lymphoma which is of recipient origin, as the tumor cells did not stain with anti-β-Gal antibodies.

Engraftment, defined as detection of >1% anti-β-gal cells, was seen in hematopoietic tissues (blood, BM and spleen) as well as epithelium of lung, liver, and intestine of all recipient animals as shown in Table 4 and FIG. 4.

β-gal$^+$ cells in BM (FIGS. 4B-F) and spleen (FIG. 4H-I) co-labeled with anti-CD45, anti-CD19, anti-Mac1, anti-Gr1 and anti-TER119 Abs. Similar results were seen for peripheral blood. Of note, no β-gal$^+$CD3$^+$ T cells were seen in either blood, BM or spleen even though β-gal$^+$CD3$^+$ T-cells were seen in chimeric mice. The reason for this is currently not known.

Engraftment in the spleen occurred mostly as clusters of donor cells, consistent with the hypothesis that when MASC home to the spleen, they proliferate locally and differentiate to form a colony of donor cells, similar to CFU-S. It is not believed that differentiation of mMASC into hematopoietic cells in vivo can by attributed to contamination of the mMASC with HSC. First, BMMNC are depleted of CD45 cells by column selection before mMASC cultures are initiated. Second, early mesodermal or hematopoietic transcription factors, including brachyury (Robertson et al., 2000), GATA-2 and GATA-1 (Weiss et al., 1995), are not expressed in undifferentiated mMASC, as shown by cDNA array analysis. Third, the culture conditions used for mMASC are not supportive for HCS. Fourth all attempts at inducing hematopoietic differentiation from hMASC in vitro, by co-culturing hMASC with hematopoietic supportive feeders and cytokines, have been unsuccessful (Reyes et al., 2001).

Significant levels of mMASC engraftment were also seen in liver, intestine and lung. Triple-color immunohistochemistry was used to identify epithelial (CK$^+$) and hematopoietic (CD45$^+$) cells in the same tissue sections of the liver, intestine and lung. In the liver, β-gal$^+$ donor-derived cells formed cords of hepatocytes (CK18$^+$CD45$^+$ or albumin$^+$), occupying about 5-10% of a given 5 μm section (FIGS. 4K-M). Several CK18$^+$ CD45$^+$β-gal hematopoietic cells of recipient origin were distinctly identified from the epithelial cells. Albumin$^+$β-gal$^+$ and CK18$^+$β-gal$^+$ cells engrafted in cords of hepatocytes surrounding portal tracts, a pattern seen in hepatic regeneration from hepatic stem cells and oval cells (Alison et al., 1998; Petersen et al., 1999). This and the fact that only 5/20 sections contained donor cells, is consistent with the notion that stem cells engraft in some but not all areas of the liver, where they proliferate and differentiate into hepatocytes.

Engraftment in the intestine was also consistent with what is known about intestinal epithelial stem cells. In the gut, each crypt contains a population of 4-5 long-lived stem cells (Pot-

TABLE 4

Engraftment levels in NOD-SCID mice transplanted with ROSA26 MASC.

| Animal | Time (Weeks) | Radiation | Engraftment levels (%) determined by immunofluorescence or (Q-PCR) | | | | | |
|---|---|---|---|---|---|---|---|---|
| | | | Marrow | Blood | Spleen | Liver | Lung | Intestine |
| 1 | 4 | No | 2 (1) | 2 | 5 | 7 | 4 | 2 |
| 2 | 5 | No | 3 (4) | 4 | 5 | 9 | 5 | 3 |
| 3 | 10 | No | 1 | 3 | 3 | 6 | 3 | 2 |
| 4 | 16 | No | 4 | 2 | 3 | 4 | 3 | 4 (4.9) |
| 5 | 24 | No | 3 | 2 | 3 | 6 | 4 | 1 |
| 6 | 8 | Yes | 8 (8) | 6 | 4 | 5 | 2 (1.1) | 7 |
| 7 | 8 | yes | 10 | 8 | 7 (7.3) | 4 | 6 | 8 |
| 8 | 8 | Yes | 5 | 8 | 3 | 5 | 5 | 6 |
| 9 | 8 | Yes | 7 | 5 | 5 | 6 | 4 | 6 |
| 10 | 10 | Yes | 5 (6) | 7 | 9 (12.5) | 5 | 2 | 8 |
| 11 | 11 | Yes | 8 | 8 | 6 | 5 | 3 | 10 (11.9) |
| 12 | 11 | Yes | 6 | 5 | 4 | 8 (6.2) | 10 (12.3) | 8 |
| SR-1 | 7 | Yes | 6 | 7 | 5 | 1 (1.7) | 5 | 8 |
| SR-2 | 10 | Yes | 5 | 4 | 8 | 3 | 4 | 6 | ten, 1998). Progeny of these stem cells undergo several rounds of division in the middle and upper portions of cypts and give rise to epithelial cells that migrate upwards, out of the crypt, onto adjacent villi. Donor derived, β-gal+panCK+ CD45− epithelial cells entirely covered several villi (FIG. 4O-P). In some villi, β-gal+panCK+CD45− cells constituted only 50% of the circumference (solid arrows, FIG. 4P) suggesting engraftment in one but not both crypts. Several β-gal+ panCK− cells were distinctly seen in the core of intestinal villi (open arrow, FIG. 4O). These cells co-stained for CD45 (FIG. 4P), indicating that they were donor-derived hematopoietic cells. In the lung, the majority of donor cells gave rise to β-gal+panCK+CD45− alveolar epithelial cells whereas, most hematopoietic cells were of recipient-origin (panCK−CD45+ β-gal−) (FIG. 4R).

Levels of engraftment detected by immunohistochemistry were concordant with levels determined by Q-PCR for NEO (Table 4). Engraftment levels were similar in animals analyzed after 4 to 24 weeks following I.V. injection of MASC (Table 4).

No contribution was seen to skeletal or cardiac muscle. In contrast to epithelial tissues and the hematopoietic system, little to no cell turnover is seen in skeletal or cardiac muscle in the absence of tissue injury. Therefore, one may not expect significant contribution of stem cells to these tissues. However, engraftment was not found in skin and kidney, two organs in which epithelial cells undergo rapid turnover. It is shown in the blastocyst injection experiments (Example 8) that mMASC can differentiate into these cell types; one possible explanation for the lack of engraftment in these organs in post-natal recipients is that mMASC do not home to these organs, a hypothesis that is currently being evaluated. Although mMASC differentiated into neuroectoderm-like cells ex vivo, no significant engraftment of mMASC was seen in the brain, and rare donor cells found in the brain did not co-label with neuroectodermal markers. Two recent publications demonstrated that donor derived cells with neuroectodermal characteristics can be detected in the brain of animals that underwent BM transplantation. However, a fully ablative preparative regimen prior to transplantation or transplantation in newborn animals was used, conditions associated with break-down of the blood-brain barrier. Cells were infused in non-irradiated adult animals, or animals treated with low dose radiation, where the blood-brain barrier is intact or only minimally damaged. This may explain the lack of mMASC engraftment in the CNS.

Confluent MASCdo Not Differentiate In Vivo

As control, ROSA26-MASC were infused and grown to confluence prior injection. MASC allowed to become confluent lose their ability to differentiate ex vivo in cells outside of the mesoderm, and behave like classical MSC (Reyes, M. et al. 2001). Infusion of $10^6$ confluent mMASC did not yield significant levels of donor cell engraftment. Although few β-gal+ cells were seen in BM, these cells did not co-label with anti-CD45 Abs, indicating that MSC may engraft in tissues, but are no longer able to differentiate into tissue specific cells in response to local cues.

MASC Derived Cells in Bone Marrow of Mice can be Serially Transferred

BM from mouse engrafted with ROSA26 MASC was tested to determine whether they contained cells that would engraft in secondary recipients. $1.5 \times 10^7$ BM cells, recovered from primary recipients 11 weeks after I.V. infusion of mMASC, were transferred to secondary irradiated NOD-SCID recipients (Table 4: animal SR-1 and SR-2). After 7 and 10 weeks, secondary recipients were sacrificed, and blood, BM, spleen, liver, lung and intestines of the recipient animal were analyzed for engraftment of ROSA26 donor cells by immunohistochemistry and Q-PCR for the NEO gene. A similar pattern of engraftment was seen in secondary recipients as in the primary recipients. Four-8% of BM, spleen and PB cells were gal+CD45+; six and 8% of intestinal epithelial cells were β-gal+pan-CK+, and 4 and 5% of lung epithelial cells were β-gal+pan-CK+. Levels of engraftment in the liver of secondary recipients were lower than in the primary recipients (1 and 3% vs. 5 and 8% β-gal+CK18+). This suggests that mMASC may persist in the BM of the primary recipient and differentiate into hematopoietic cells as well as epithelial cells when transferred to a second recipient.

MASC derived cells can produce insulin in vivo. MASC from ROSA26 mice were injected into irradiated NOD-SCID mice as described herein. The resulting MASC derived cells co-stain for LacZ and insulin in a model of streptozotocin-induced diabetes.

SUMMARY

One of the critical questions in "stem cell plasticity" is whether the engrafted and differentiated donor mMASC are functional. The results described herein show that one animal developed a lymphoma in thymus and spleen after 16 weeks, as is commonly see in aging NOD-SCID mice (Prochazka et al., 1992). Phenotypic analysis showed that this B-cell lymphoma was host-derived: CD19+ cells were β-gal−. Approximately 40% of CD45−vWF+ cells in the vasculasture of the tumor stained with anti-β-gal Abs, indicating that neoangiogenesis in the tumor was in part derived from donor mMASC (FIG. 4T). This suggests that MASC give rise to functioning progeny in vivo. Likewise, higher levels of mMASC engraftment and differentiation in radiosensitive organs, such as the hematopoietic system and intestinal epithelium (Table 4, $p<0.001$), following low dose irradiation suggests that mMASC may contribute functionally to host tissues.

These results showed that mammalian MASC can be purified, expanded ex vivo, and infused I.V., homed to various sites in the body, engraft into numerous organs, and that the cells are alive in these various organs one month or longer. Such donor cells, undifferentiated, and differentiated progeny are found, by virtue of the fluorescent marker, in organs including, but not limited to, the BM, spleen, liver and lung. These cells can be used to repopulate one or more compartment(s) to augment or restore cell or organ function.

Example 7

Demonstration of In Vitro Hematopoiesis and Erythropoiesis

MASC from, human BM differentiate at the single cell level into neuroectodermal, endodermal and many mesodermal lineages, including endothelial cells. Because endothelium and blood are very closely related in ontogeny, it can be hypothesized that MASC can differentiate into hematopoietic cells. eGFP transduced human MASC, that are GlyA, CD45 and CD34 negative (n=20), were cocultured with the mouse yolk sac mesodermal cell line, YSM5, as suspension cell aggregates for 6 days in serum free medium supplemented with 10 ng/mL bFGF and VEGF. After six days, only eGFP+ cells (i.e., MASC progeny) remained and YSM5 cells had died.

Remaining cells were transferred to methylcellulose cultures containing 10% fetal calf serum supplemented with 10 ng/mL bone morphogenic protein (BMP)4, VEGF, bFGF, stem cell factor (SCF), Flt3L, hyper IL6, thrombopoietin (TPO), and erythropoietin (EPO) for 2 weeks. In these cultures, both adherent eGFP⁺ cells and small, round non-adherent cells, which formed many colonies attached to the adherent cells were detected. The non-adherent and adherent fractions were collected separately and cultured in 10% FCS containing medium with 10 ng/mL VEGF and bFGF for 7 days. Adherent cells stained positive for vWF, formed vascular tubes when plated on ECM, and were able to uptake a-LDL, indicating their endothelial nature. 5-50% of the non-adherent cells stained positive for human specific GlyA and HLA-class I by flow cytometry. Gly-A⁺/HLA-class-I⁺ cells were selected by FACS. On Wright-Giemsa, these cells exhibited the characteristic morphology and staining pattern of primitive erythroblasts. Cells were benzidine⁺ and human Hb⁺ by immunoperoxidase. By RT-PCR these cells expressed human specific Hb-e, but not Hb-a.

When replated in methylcellulose assay with 20% FCS and EPO, small erythroid colonies were seen after 10 days, and 100% of these colonies stained positive for human specific GlyA and Hb. As selection of MASC depends on the depletion of CD45⁺ and Gly A⁺ cells from BM, and cultured MASC are CD45⁻ and GlyA⁻ at all times examined using both FACS and cDNA array analysis, contamination of MASC with hematopoietic cells is very unlikely.

Example 8

In Vivo Proof of the Multipotent Nature of MASC as Shown by Multiple Organ Chimerism Following Blastocyst Injections of the Cells Important for therapeutic applications of these cells is the ability of MASC to proliferate and differentiate into the appropriate cell types in vivo. Up until this point the only cells that should be capable of contributing to the full constellation of tissues and organs in the body are ES cells. In order to analyze whether MASC could show the full capability of ES cells, they were assayed to determine their contribution to the formation of various tissues by introducing them into the early blastocyst and observing the fate of their progeny.

MASC were generated from marrow of ROSA26 mice that are transgenic for the β-galactosidase (β-gal) gene (Rafii, S., et al. 1994, Blood 84:10-13) and expanded as described in Example 1. One or 10-12 ROSA26 MASC obtained after 55-65 PDs were microinjected into 88 and 40 3.5-day C57BL/6 blastocysts, respectively. Blastocysts (8/mother) were transferred to 16 foster mothers and mice allowed to develop and be born as shown in Table 5.

TABLE 5

Degree of chimerism following MASC injection in blastocyst

| MASC/ blastocyst | Litters born | Total # pups born | NEO positive by Q-PCR | | | | |
| --- | --- | --- | --- | --- | --- | --- | --- |
| | | | 0% | 1-10% | 10-20% | 20-40% | >40% |
| 10-12 | 4/11 | 22 | 5/22 (23%) | 13/22 (59%) | 2/22 (9%) | 1/22 (4.5%) | 1/22 (4.5%) |
| 1 | 3/5 | 15 | 8/15 (53%) | 5/15 (33%) | 0/15 (0%) | 0/15 (0%) | 2/15 (13%) |

Seven litters were born, in line with the birth rate seen in other studies during this period. The number of mice per litter varied between 1 and 8, for a total of 37 mice. Animals born from microinjected blastocysts were of similar size as normal animals and did not display any overt abnormalities.

After four weeks, animals were evaluated for chimerism by clipping their tails and assessing the contribution of β-gal/NEO transgene containing cells to the tails by Q-PCR for NEO. Percent chimerism was determined by comparing the number of NEO copies in test samples with that in tissue from ROSA26 mice according to manufacturer's recommendations (7700 ABI PRISM Detector Software 1.6). Chimerism could be detected in 70% of mice derived from blastocysts in which 10 to 12 MASC had been injected and 50% of mice derived from blastocysts microinjected with 1 MASC (Table 5). The degree of chimerism ranged between 0.1% to >45%. After 6 to 20 weeks, animals were sacrificed. Some mice were frozen in liquid nitrogen and thin sections were cut as described. Whole-mouse sections were stained with X-Gal. One thousand sets of digital images covering completely each section were then assembled to create a composite image of each whole-mouse section. In a representative non-chimeric animal (by Q-PCR for NEO) derived from a blastocyst in which a single MASC was injected, no X-Gal staining was seen. In contrast, the animal was 45% chimeric by R-PCR for NEO by tail clip analysis and had contribution of a single ROSA26-derived MASC to all somatic tissues.

For other animals, multiple organs were harvested and analyzed for the presence of MASC derived cells by X-GAL staining, staining with an anti-β-gal-FITC antibody, and Q-PCR for NEO. Animals that had NEO⁺ cells in tail-clippings had contribution of the ROSA26-derived MASC in all tissues, including the brain, retina, lung, cardiac and skeletal muscle, liver, intestine, kidney, spleen, BM, blood, and skin as shown by X-GAL staining and staining with an anti-β-gal-FITC antibody.

Chimerism was detected by X-Gal staining and anti-β-gal staining in the animals generated from blastocysts microinjected with ROSA26 MASC. β-gal⁺ cells expressed markers typical for the tissue in which they had incorporated. β-gal⁺ cells co-stained with anti-β-gal⁺ FITC and anti-NF200 or GFAP and TOPRO3 (observed at 20× magnification) for NF200 and GFAP in the central nervous system and for dystrophin in the skeletal muscle. Lung tissue was stained for anti-β-gal-FITC and pan-CK in alveoli and bronchi (also TOPRO3) (observed at 20× magnification). Skeletal muscle was stained with anti-β-gal-FITC, dystrophin-PE, and TOPRO3 was observed at 20× magnification. Heart was stained with anti-β-gal-FITC and cardiac troponin-1-Cy3, TOPRO3 was observed at 20× magnification. Liver was stained with anti-β-gal-FITC and pan-CK-PE and TOPRO3 (was observed with 40× magnification and 10× magnification). Intestine was stained with anti-β-gal-FITC, pan-CK-PE, and TOPRO3 was observed at 20× magnification. Kidney was stained with anti-β-gal-FITC (glomerulus, tubulus) was observed at 20× magnification. Marrow staining was observed with anti-β-gal-FITC and CD45-PE, GR1-PE and MAC1-PE. Spleen staining was observed with anti-β-gal-FITC and CD45-PE, CD3-PE and CD 19-PE. Levels of engraftment estimated by Q-PCR for NEO were concordant with those estimated by X-GAL and anti-β-gal-FITC staining.

Summary

These data demonstrate for the first time that BM derived single MASC integrate into the developing mouse, giving rise to cells of various fates, and contributing to the generation of all tissues and organs of the three germ layers of the mouse. As all live animals, irrespective of the degree of chimerism, had normal functioning organs, these studies also suggest that MASC can differentiate in vivo in functional cells of the three germ layers. Whether MASC contribute to germ cells, when injected in a blastocyst or when injected postnatally, has not yet been tested.

Example 9

Origin of Endothelial Progenitors

Vasculogenesis, the in situ differentiation of primitive endothelial progenitors, termed angioblasts, into endothelial cells that aggregate into a primary capillary plexus is responsible for the development of the vascular system during embryogenesis (Hirashima et al., 1999). In contrast, angiogenesis, defined as the formation of new blood vessels by a process of sprouting from preexisting vessels, occurs both during development and in postnatal life (Holash et al., 1999; Yang et al., 2001). Until recently, it was thought that blood vessel formation in post-natal life was mediated by sprouting of endothelial cells from existing vessels. However, recent studies have suggested that endothelial "stem cells" may persist into adult life, where they contribute to the formation of new blood vessels (Peichev et al., 2000; Lin et al., 2000; Gehling et al., 2000; Asahara et al., 1997; Shi et al., 1998), suggesting that like during development neoangiogenesis in the adult may at least in part depend on a process of vasculogenesis. Precursors for endothelial cells have been isolated from BM and peripheral blood (Peichev et al., 2000; Watt et al., 1995). The ontogeny of these endothelial progenitors is unknown.

During development, endothelial cells are derived from mesoderm. The VEGF receptor 2, Flk1, characterizes the hemangioblasts, a bipotent stem cell found in the aorto-gonad-mesonephros region (Medvinsky et al., 1996; Fong et al., 1999; Peault, 1996) and in fetal liver (Fong et al., 1999), and commitment of embryoid bodies to hemangioblasts is accompanied with expression of Flk1 (Choi et al., 1998; Choi, 1998). Whether hemangioblasts persist in adult life is not known, and only HSC and endothelial progenitors have been documented. Like hemangioblasts, endothelial progenitors express Flk1 (Peichev et al., 2000) and one report suggested that HSC in post-natal life express Flk1 (Ziegler et al., 1999). During embryology, commitment of the hemangioblast to the endothelial lineage is characterized by the sequential expression of VE-cadherin, CD31, and shortly afterwards CD34 (Nishikawa et al., 1998; Yamashita et al., 2000). In post-natal life, endothelial progenitors have been selected from BM and blood using Abs against AC 133, Flk1, CD34, and the H1P12 Ab (Peichev et al., 2000; Lin et al., 2000; Gehling et al., 2000). AC133 has also been found on other cells, including NSCs (Uchida et al., 2000) and gastrointestinal epithelial cells (Corbeil et al., 2000). Upon differentiation to mature endothelium, the AC133 receptor is quickly lost (Peichev et al., 2000; Gehling et al., 2000). Another receptor found on circulating endothelial cells is a mucin, MUC18, recognized by the H1P12 Ab (Lin et al., 2000). MUC18 is lost upon differentiation of endothelial progenitors to endothelium. CD34 is expressed on endothelial progenitors, as well as on hematopoietic progenitors (Peichev et al., 2000; Baumhueter et al., 1994) and hepatic oval cells (Crosby et al., 2001). This antigen is also lost upon differentiation of endothelial progenitors to endothelium. Most mature endothelial cells, but microvascular endothelial cells, no longer express CD34.

It is described here for the first time, the in vitro generation of vast numbers of endothelial cells that engraft in vivo and contribute to neoangiogenesis from a MASC. MASC can be culture expanded for >80 PDs and endothelial cells generated from MASC can be expanded for at least and additional 20 PDs. MASC may therefore be an ideal source of endothelial cells for clinical therapies. In addition, as MASC are ontogenically less mature than the "angioblast", this model should be useful to characterize endothelial commitment and differentiation.

hMASC Differentiate into Cells with Phenotypic Characteristics of Endothelium

MASC were obtained and cultured as described in Example 3. To induce endothelial differentiation, MASC were replated at $2\times10^4$ cells/cm$^2$ in FN-coated wells in serum-free expansion medium without EGF and PDGF-BB but with 10 ng/mL VEGF. In some instances, FCS was added. Cultures were maintained by media exchange every 4-5 days. In some instances, cells were subcultured after day 9 at a 1:4 dilution under the same culture conditions for 20+ PDs.

In order to define endothelial differentiation from MASC more extensively, FACS and immunohistochemical analysis of cells after 3-18 days was performed. Expression of Flk1 and Flt1 on undifferentiated MASC was low, was maximal at day 9, and persisted until day 18. VE-cadherin, present on BM or blood endothelial progenitors (Peichev et al., 2000; Nishikawa et al., 1998), was not expressed on undifferentiated MASC, but was expressed after 3 days of culture with VEGF and persisted until day 18. MASC expressed low levels of AC133, found on endothelial as well as hematopoietic progenitors (Peichev et al., 2000; Gehling et al., 2000) but was no longer detectable after day 3. CD34, present on endothelial and hematopoietic progenitors (Peichev et al., 2000; Asahara et al., 1997; Rafii et al., 1994), was not present on undifferentiated MASC (FIG. 4A) but was expressed from day 9 until day 18. The mucin, MUC18, recognized by the Ab H1P12 has been used to purify endothelial progenitors from blood (Lin et al., 2000). Although MASC did not stain with H1P12 MASC treated with VEGF for 9 days stained positive, but expression was lost by day 18.

Figure 5:
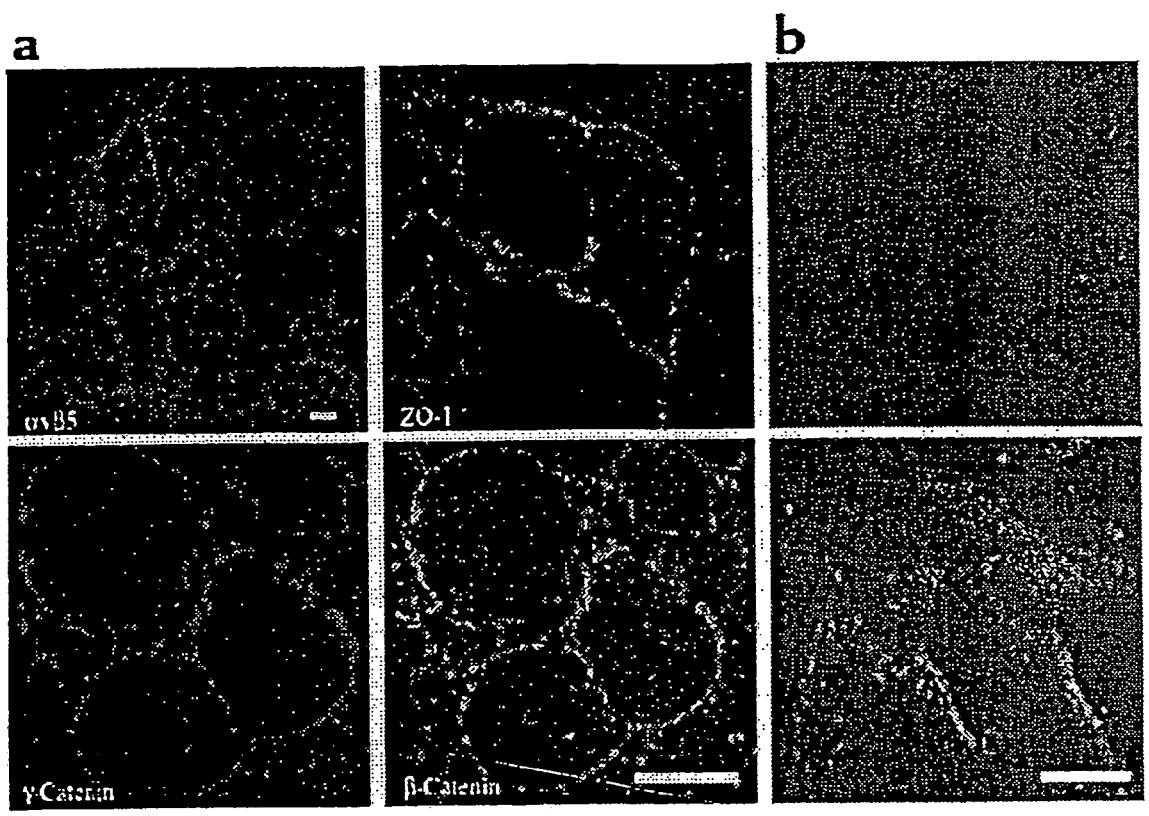
FIG. 5 shows immunohistochemical evaluation of MASC-derived endothelial cells using confocal fluorescence microscopy. (a) MASC grown for 14 days in VEGF. Typical membrane staining is seen for the adhesion receptor, avρ5, and for the adherens junction proteins, ZO-1, β- and γ-catenin. Scale bar=50 μm. (b) Morphology in bright field of MASC at day 0 (upper panel) and day 21 (lower panel) after VEGF treatment. Bar=25 μm.
Figure 6:
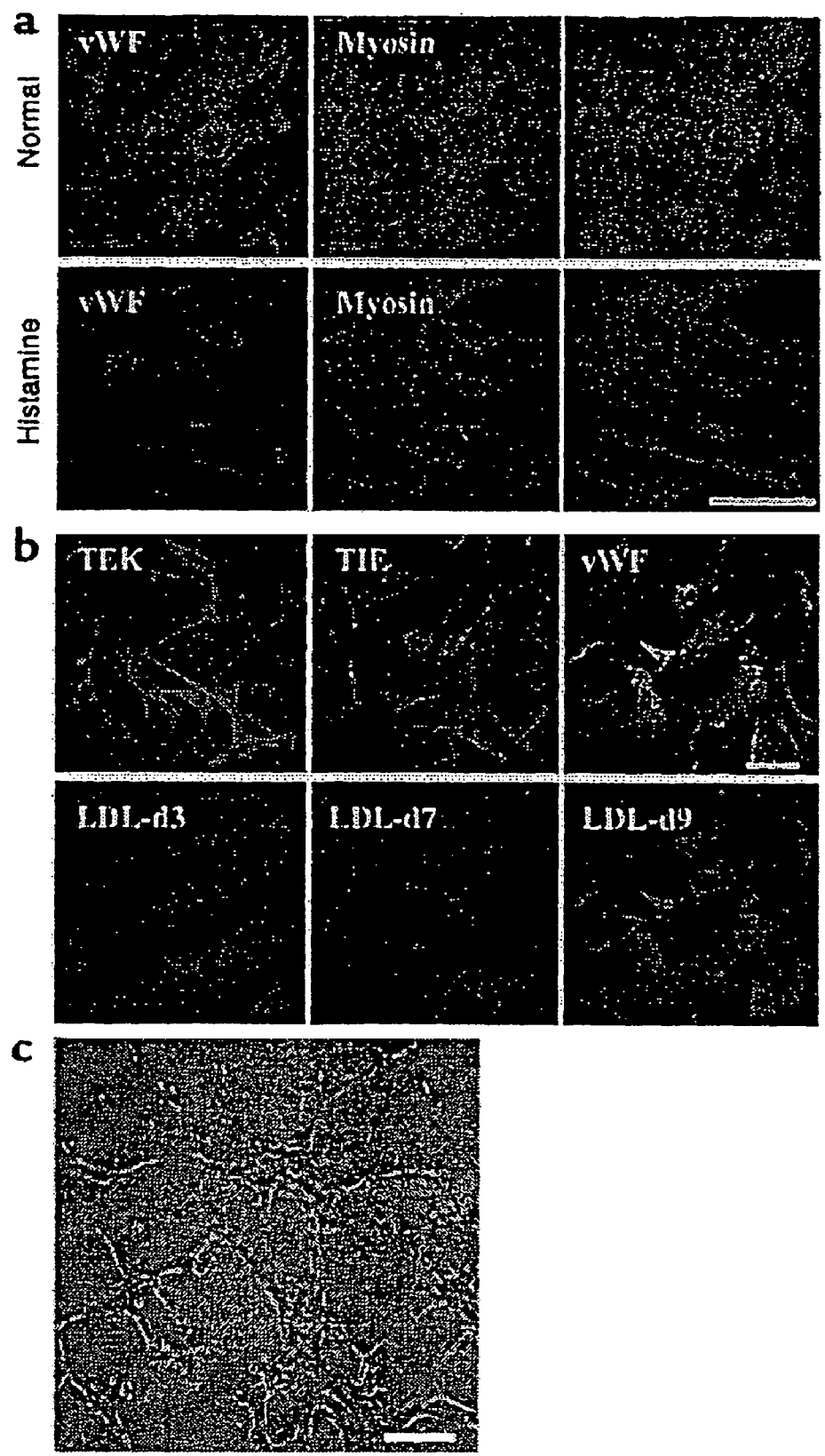
FIG. 6 shows a photomicrograph of MASC derived endothelial cells. Panel A shows histamine-mediated release of vWF from MASC-derived endothelium. Staining with antibodies against myosin shows cytoskeletal changes with increased numbers of myosin stress fibers, and widening of gap junctions (Arrows) (Representative example of 3 experiments). Scale bar=60 μm; panel B shows MASC-derived endothelium takes up a-LDL. After 7 days, cells expressed Tie-1, but again did not take up a-LDL. However, acquisition of expression of vVWF on day 9 was associated with uptake of aLDL (representative example of 10 experiments). Scale bar=100 μm; and panel C shows vascular tube formation by MASC-derived endothelium. After 6 h, typical vascular tubes could be seen. (Representative example of 6 experiments). Scale bar=200 μm
Figure 7:
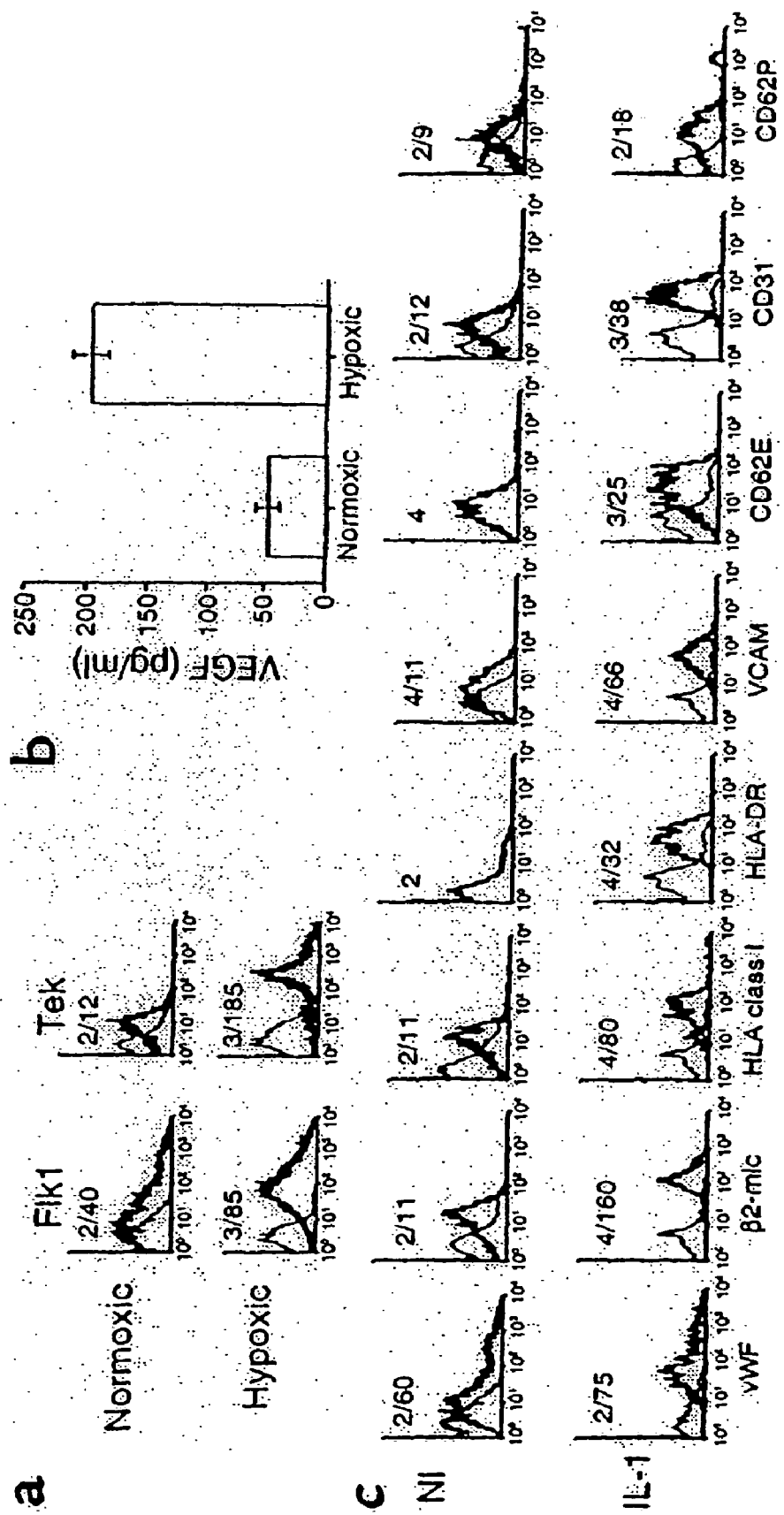
FIG. 7 shows a graphical illustration of FACS analysis of MASC derived endothelial cells. The Plots show isotype control IgG staining profile (thin line) vs. specific antibody staining profile (thick line) (Representative example of >3 experiments). Number above plots is the Mean Fluorescence Intensity (MFI) for the control IgG staining and the specific antibody staining. Panel A shows hypoxia upregulates Flk1 and Tek expression on MASC-derived endothelial cells analyzed by flow cytometry; panel B shows that hypoxia upregulates VEGF production by MASC-derived endothelial cells. VEGF levels were measured by ELISA and the results are shown as Mean±SEM of 6 experiments; and panel C shows that IL-1a induces expression of class II HLA antigens and increases expression of adhesion receptors. Plots show isotype control IgG staining profile (thin line) vs. specific antibody staining profile (thick line) (Representative example of 3 experiments). Number above plots shows MFI for the control IgG staining and the specific antibody staining.
Figure 8:
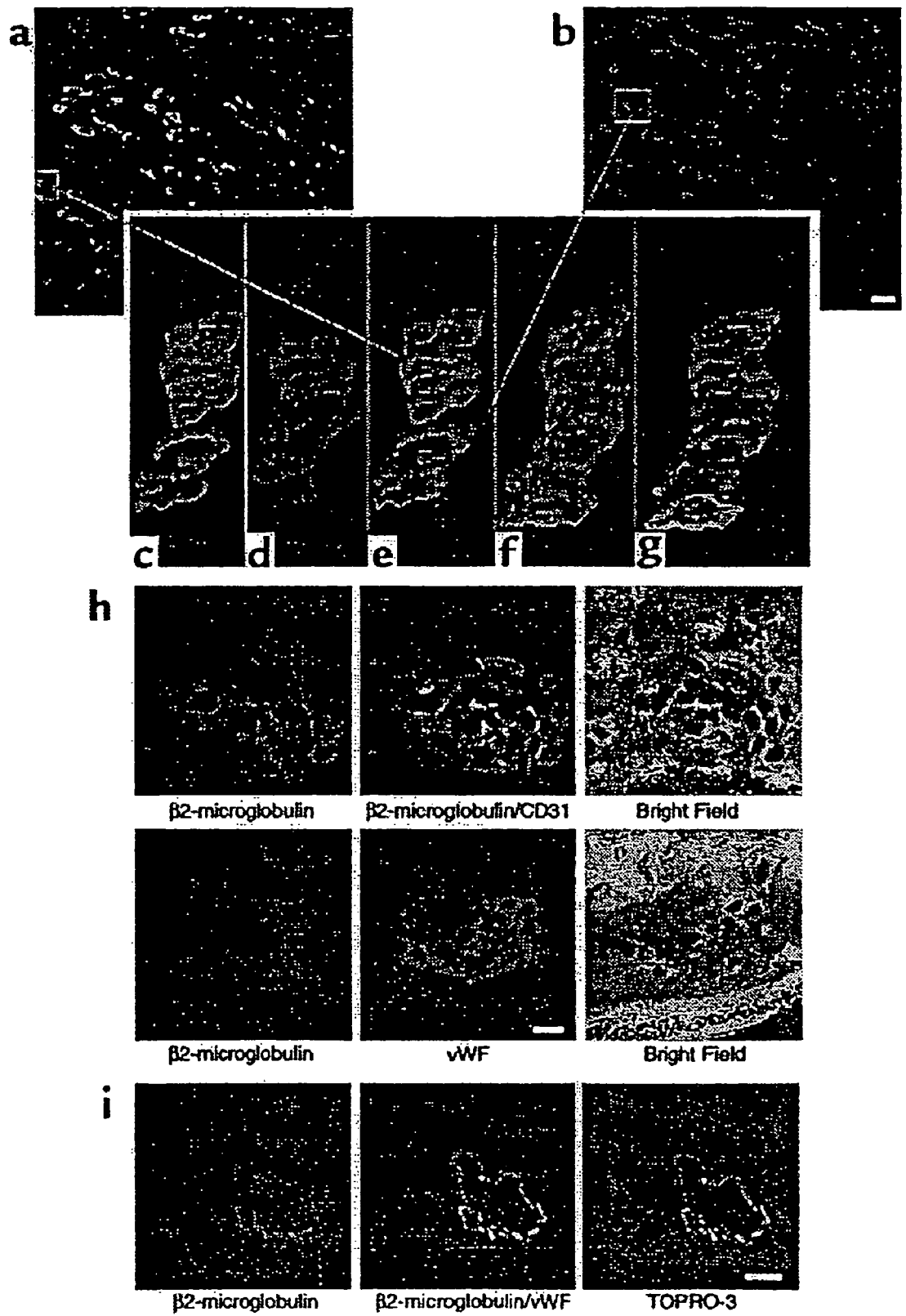
FIG. 8 shows a photomicrograph of human MASC derived endothelial cells. Panels C-F show the 3-D reconstructed figures for either anti-human β2-microglobulin-FITC (panel C) or anti-mouse-CD31-FITC (panel D) and merging of the two (Panel E), anti-vWF-Cy3 (Panel F), and merging of the three staining patterns (Panel G). Panels A and B show the confocal image of a single slice stained with either anti-human β2-microglobulin-FITC and anti-vWF-Cy3, or anti-mouse-CD31-Cy5 and anti-vWF-Cy3. Scale bar=100 μm. Panel H shows wound healing resulting in a highly vascularized area in the punched ear stained with anti-β2-microglobulin-FITC and anti-vWF in mice injected with human MASC-derived endothelial cells (Top panel) or human foreskin fibroblasts (Bottom panel). Scale bar=20 μm. C=Cartilage. D=dermis. Panel I shows that tumor angiogenesis is derived from endothelial cells generated in vivo from MASC resulting in a highly vascularized area in the tumor stained with anti-X32-microglobulin-FITC, anti-vWF and TOPRO-3. Scale bar=20 μm.

The endothelium specific integrin, $\alpha v\beta 3$, (Eliceiri et al., 2000) was not present on undifferentiated MASC, whereas $\alpha v\beta 5$ was expressed at very low levels. Expression of integrins increased progressively during differentiation and was maximal by day 14 (FIG. 5). The tyrosine kinase receptors, Tie and Tek, important for angiogenesis but not endothelial cell differentiation (Partanen et al., 1999), were not expressed on MASC. Expression of Tek could be seen after day 3 and Tie after day 7 (FIG. 6). MASC also do not express vWF, but vWF was expressed from day 9 on (Rosenberg et al., 1998; Wagner et al., 1982). More mature endothelial markers, including CD31, CD36, CD62-P (Tedder et al., 1995) (FIG. 7), and the adhesion junction proteins ZO-1, β-catenin, and γ-catenin (FIG. 5) were detected after day 14 (Li et al., 1990; Van Rijen et al., 1997; Petzelbauer et al., 2000). VCAM or CD62-E were not expressed at high level at any time point during differentiation, unless endothelium was activated with IL-1α, as described below. Differentiation to endothelium was associated with acquisition of β2-microglobulin and low levels of HLA-class I antigens, but not HLA-class II.

It has been reported previously, that endothelial differentiation can only be obtained from MASC expanded with 2% FCS or less, but not when expanded with 10% FCS (Reyes et al., 2001) as higher concentrations of FCS supports growth of classical MSC that differentiate only into osteoblasts, chondroblasts and adipocytes (Reyes et al., 2001; Pittenger et al., 1999). When FCS was present during the initial 7 days of differentiation, endothelial differentiation could not be induced. When non-confluent MASC ($<1\times10^4$ cells/cm$^2$) were induced to differentiate, endothelial was not seen. When MASC were subcultured 9-days after exposure to VEGF using serum free medium with 10 ng/mL VEGF, cells could undergo at least an additional 12 PDs. When 10% FCS and 10 ng/mL VEGF was added to the medium for subculturing, MASC-derived endothelial cells could undergo an additional 20+ PDs, irrespective of the number of PDs that MASC had undergone. Compared with undifferentiated MASC, endothelial cells were larger, and had a lower nuclear/cytoplasm ratio. Results were similar when MASC were used from cultures that had undergone 20 (n=30) or 50+ (n=25) PDs.

Functional Characteristics of MASC-Derived Endothelium

It was tested whether VEGF-induced differentiated progeny of hMASC had functional characteristics of endothelial cells. Endothelial cells respond to hypoxia by upregulating expression of VEGF as well as the VEGF receptors Flk1 and the angiogenesis receptors, Tie-1 and Tek (Kourembanas et al., 1998). hMASC and hMASC-derived endothelial cells were incubated at 37° C. in 20% or 10% $O_2$ for 24 h. Cells were stained with Abs against Flk1, Flt1, Tek and IgG control, fixed in 2% paraformaldehyde and analyzed by flow cytometry. In addition, VEGF concentrations in the culture supernatants was measured using an ELISA kit (AP biotech, Piscataway, N.J.). MASC-derived endothelial cells and undifferentiated MASC were exposed to hypoxic conditions for 24 h.

Expression of Flk1 and Tek was significantly increased on MASC-derived endothelial cells exposed to hypoxia (FIG. 7), while the levels of these receptors remained unchanged on undifferentiated MASC. In addition, levels of VEGF in culture supernatants of hypoxic endothelial cultures was increased by 4 fold (FIG. 7B) whereas VEGF levels in MASC cultures exposed to hypoxia remained unchanged.

It was next tested whether MASC-derived endothelial cells would upregulate expression of HLA-antigens and cell adhesion ligands in response to inflammatory cytokines, such as IL-1α (Meager, 1999; Steeber et al., 2001). $10^6$ MASC and MASC-derived endothelial cells were incubated with 75 ng/ml IL-1α (R&D Systems) in serum-free medium for 24 h. Cells were fixed in 2% paraformaldehyde and stained with Abs against HLA-class I, class II, β2-microglobulin, vWF, CD31, VCAM, CD62E and CD62P, or control Abs, and analyzed using a FACS-calibur (Becton Dickinson).

Significantly increased levels of HLA-Class I and II, P2-microglobulin, VCAM, ECAM, CD62E, CD62P were seen by FACS analysis (FIG. 7C) on endothelial cells. In contrast, on undifferentiated MASC only upregulation of Flk was seen.

Another characteristic of endothelial cells is that they take up LDL (Steinberg et al., 1985). This was tested by incubating MASC induced to differentiate with VEGF for 2, 3, 5, 7, 9, 12 and 15 and 21 with LDL-dil-acil. The dil-Ac-LDL staining kit was purchased from Biomedical Technologies (Stoughton, Mass.). The assay was performed as per manufacture's recommendations. Cells were co-labeled either with anti-Tek, -Tie-1 or -vWF Abs. After 3 days, expression of Tek was detected but no uptake of a-LDL. After 7 days, cells expressed Tie-1, but did not take up significant amounts of a-LDL. However, acquisition of expression of vWF on day 9 was associated with uptake of aLDL (FIG. 6B).

Endothelial cells contain vWF stored in Weibel Pallade bodies that is released in vivo when endothelium is activated (Wagner et al., 1982). This can be induced in vitro by stimulating cells with histamine (Rosenberg et al., 1998), which also results in activation of the cell cytoskeleton (Vischer et al., 2000). MASC-derived endothelial cells were plated at high confluency ($10^4$ cells/cm$^2$) in FN-coated chamber slides. After 24 h, cells were treated with 10 μM histamine (Sigma) in serum free medium for 25 min. and stained with Abs against vWF and myosin. Untreated and treated cells were fixed with methanol at −20° C. for 2 min, stained with Abs against vWF and myosin, and analyzed using fluorescence and/or confocal microscopy. vWF was present throughout the cytoplasm of untreated endothelial cells. Cytoplasm of endothelial cells treated with histamine contained significantly less vWF and vWF was only detectable in the perinuclear region, likely representing vWF present in the endoplasmic reticulum (FIG. 6A). Histamine treatment caused widening of gap junctions and cytoskeletal changes with increased numbers of myosin stress fibers (FIG. 6A).

Finally, endothelial cells were tested to determine if they could form "vascular tubes" when plated on Matrigel™ or extracellular matrix (ECM) (Haralabopoulos et al., 1997). 0.5 ml extracellular matrix (Sigma) was added per well of a 24 well plate, incubated for 3 h at 37° C. $10^4$ MASC and MASC-derived endothelial cells were added per well in 0.5 ml of serum free plus VEGF medium and incubated at 37° C. As shown in FIG. 6C, culture of MASC derived endothelial cells on ECM resulted in vascular tube formation within 6 hours.

hmASC-Derived Endothelial Cells Contribute to Tumor-Angiogenesis In Vivo

A breeding colony of NOD-SCID mice was established from mice obtained from the Jackson Laboratories (Bar Harbor, Me.). Mice were kept in specific pathogen free conditions and maintained on acidified water and autoclaved food. Trimethoprim 60 mg and sulphamethoxazole 300 mg (Hoffmann-La Roche Inc., Nutley, N.J.) per 100 ml water was given twice weekly.

Three Lewis lung carcinoma spheroids were implanted subcutaneously in the shoulder. 3 and 5 days after implantation of the tumor, mice were injected with 0.25×$10^6$ human MASC-derived endothelial cells or human foreskin fibroblasts via tail vein injection. After 14 days, animals were sacrificed, tumors removed and cryopreserved using OTC compound (Santura Finetek USA Inc, Torrance, Calif.) at −80° C. In addition, the ears that were clipped to tag the mouse were also removed and cryopreserved using OTC compound at −80° C. Five μm thick sections of the tissues were mounted on glass slides and were fixed and stained as described below.

Computer-aided analysis of length and number of branches counted on five sections of each tumor showed that tumors in mice that received human MASC-derived endothelial cells had a 1.45±0.04 fold greater vascular mass than tumors in control mice that did with anti-human-β2-microglobulin or HLA-Class I Abs, combined with anti-mouse-anti-CD31 Abs and anti-vWF, anti-Tek- or anti-Tie-I Abs, which recognize both human and mouse endothelial cells. These initial studies showed that some blood vessels in the tumor contained anti-human-β2-microglobulin or HLA-Class I positive cells that co-labeled for either vWF, Tie or Tek, but not with mouse-CD31, indicating that human MASC-derived endothelial cells contributed to tumor neoangiogenesis in vivo.

To better address the degree of contribution, 35 sequential 5 μm slides were obtained and were stained in an alternate fashion with either anti-human P2-microglobulin-FITC or anti-mouse-CD31-Cy5 and anti-vWF-Cy3. All slides were examined by confocal microscopy. The different figures were then assembled in 3-D to determine the relative contribution of human and murine endothelial cells to the tumor vessels. When tumors obtained from animals injected with human-MASC derived endothelial cells were analyzed approximately 35% of the tumor vessels were positive for anti-human β2-microglobulin as well as vWF whereas approximately 40% of endothelial cells stained positive with anti-mouse CD31 Abs (FIGS. 8A-G). Tumors in animals that did not receive endothelial cells or received human fibroblasts did not contain endothelial cells that stained positive with the anti-β2-microglobulin or anti-HLA-class-I Abs Abs.

Figure 9:
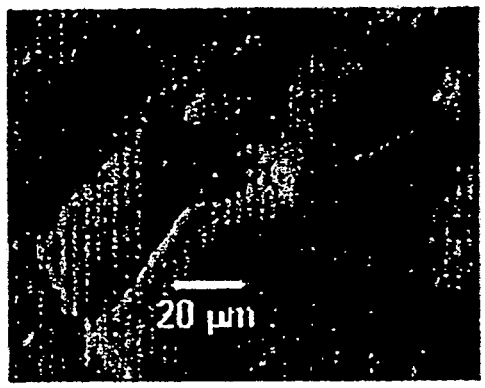
FIG. 9 shows spiking behavior and expressed voltage-gated sodium currents in hMSC derived neuron-like cells. Panel A shows a photomicrograph of cultured hMSC-derived neurons that showed spiking behavior and expressed voltage-gated sodium currents (the shadow of the pipette points to the cell). Panel B shows graphical illustrations of current-clamp recordings from a hMSC derived neuron. Panel C shows graphical illustrations of leak-subtracted current traces from the same hMSC derived neuron.
Figure 9:
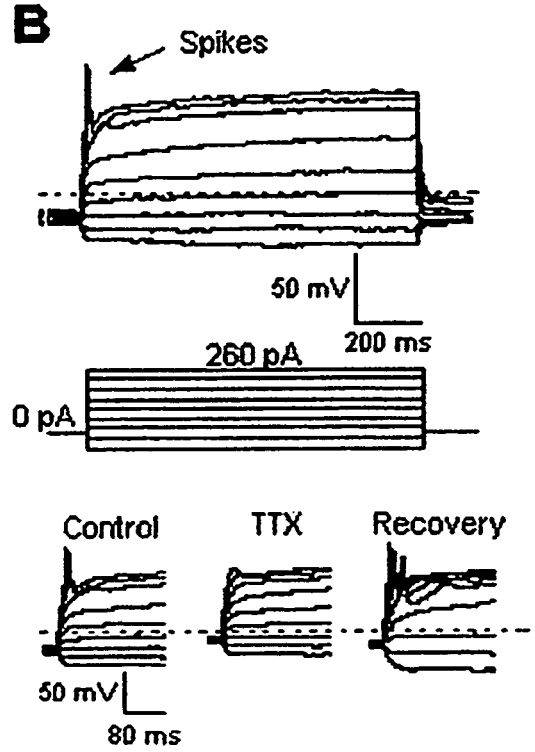
Figure 9:
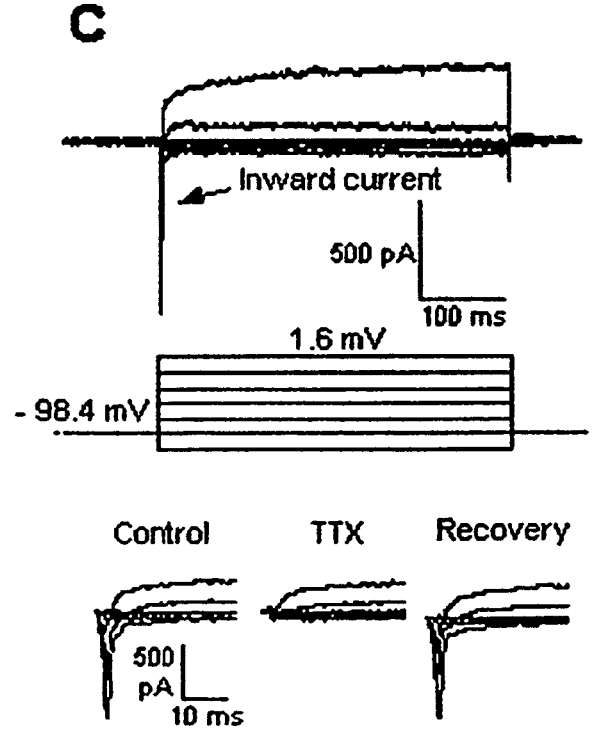

MASC-derived endothelial cells were also analyzed whether they contribute to wound healing angiogenesis. The area of the ear that had been clipped to tag the mouse was then examined. Neoangiogenesis in the ear wounds was in part derived from the MASC derived endothelial cells. Similar to blood vessels in the tumor the percent human endothelial cells present in the healed skin wound was 30-45% (FIG. 9H).

Undifferentiated hMASC Differentiate in Endothelial Cells In Vivo $10^6$ undifferentiated MASC were injected I.V. in 6-week old NOD-SCID mice. Animals were maintained for 12 weeks and then sacrificed. In one animal, a thymic tumor was detected, which is commonly seen in aging NOD-SCID mice (Prochazka et al., 1992). The thymus was removed and cryopreserved in OTC compound at −80° C. Ten μm thick sections of the tissues were mounted on glass slides and were fixed and stained as described below.

All hematopoietic cells stained positive for mouse CD45 but not human CD45, indicating that they were murine in origin. The tumor was then stained with an anti-human P2-microglobulin-FITC Ab and an anti-vWF-Cy3 Ab that recognizes both human and mouse endothelial cells. Approximately 12% of the vasculature was derived from hMASC (FIG. 9I). These studies further confirmed that the hematopoietic elements were not of human origin, as no human P2-microglobulin was detected outside of the vascular structures.

Immunohistochemistry and Data Analysis

In vitro cultures: Undifferentiated MASC or MASC induced to differentiate to endothelium for 2-18 days, plated in FN coated chamber slides were fixed with 2% paraformaldehyde (Sigma) for 4 min at room temperature. For cytoskeleton staining chamber slides were fixed with methanol for 2 min at −20° C. For intracellular ligands, cells were permeabilized with 0.1 Triton-X (Sigma) for 10 min and incubated sequentially for 30 h in each with primary antibody (Ab), and FITC, PE or Cy5 coupled anti-mouse-, goat- or rabbit-IgG Ab. Between each step, slides were washed with PBS+1% BSA. Primary Abs against CD31, CD34, CD36, CD44, HLA-class I and -II, β2-microglobulin were used at a 1:50 dilution. Primary Abs against VCAM, ICAM, VE-cadherin, selectins, HIP12, ZO-1, connexin-40, connexin-43, MUC 18, $\alpha_v\beta_3$, $\alpha_v\beta_5$, B-catenin and γ-catenin (Chemicon) and Tek, Tie, vWF (Santa Cruz) were used at a 1:50 dilution. Stress fibers were stained with Abs against myosin (light chain 20 kD, clone no. MY-21; 1:200). Secondary Abs were purchased from Sigma and used at the following dilutions: anti-goat IgG-Cy-3 (1:40), anti-goat IgG-FITC (1:160), anti-mouse IgG-Cy-3 (1:150) and anti-mouse IgG-FITC (1:320), anti-rabbit-FITC (1:160) and anti-rabbit-Cy-3 (1:30). TOPRO-3 was purchased from Sigma. Cells were examined by fluorescence microscopy using a Zeiss Axiovert scope (Carl Zeiss, Inc., Thomwood, N.Y.) as well as by confocal fluorescence microscopy using a Confocal 1024 microscope (Olympus AX70, Olympus Optical Co. LTD, Japan).

Tumors or normal tissue: The tissue was sliced using a cryostat in 5-10 μm thick slices. Slices were fixed with acetone for 10 min at room temperature and permeabilized with 0.1 Triton X for 5 min. Slides were incubated overnight for vWF, Tie or Tek, followed by secondary incubation with FITC, PE or Cy5 coupled anti-mouse-, goat- or rabbit-IgG Abs and sequential incubation with Abs against mouse CD45-PE or human CD45-FITC, human P2-microglobulin-FITC, mouse CD31-FITC or TOPRO-3 for 60 min. Between each step, slides were washed with PBS+1% BSA. Slides were examined by fluorescence microscopy using a Zeiss Axiovert scope as well as by confocal fluorescence microscopy using a Confocal 1024 microscope. 3D-reconstruction consisted of the collection of sequential 0.5 μm confocal photos from 35 slides of 5 μm thick to a total of 350 photos. Slides were stained with vWF-Cy3 and alternately double stained with humanβ2-microglobulin-FITC or mouse CD31-FITC. The photos from each slide were aligned with the next slide in Metamorph software (Universal Imaging Corp) and the 3D reconstruction was made in 3D Doctor Software (Able software Corp).

Volume of relative contribution of human (green) and murine endothelial cells (false colored as blue) to the 3D vessel was calculated as cubic pixels of each color. The area of each color was also calculated as square pixels in 4 vessels through the 35 slides to obtain an accurate percentage of contribution. The area of each color was also calculated in alternate slides of four different tumors.

Summary

The central finding of this study is that cells that co-purify with MSC from BM have the ability to differentiate to endothelial cells that have in vitro functional characteristics indistinguishable from mature endothelial cells. It is also shown that such endothelial cells contribute to neoangiogenesis in vivo in the setting of wound healing and tumorigenesis, and that undifferentiated MASC can respond to local cues in vivo to differentiate into endothelial cells contributing to tumor angiogenesis. As the same cell that differentiates to endothelium also differentiates to other mesodermal cell types, as well as cells of non-mesodermal origin, the cell defined here precedes the angioblast, and even the hemangioblast in ontogeny.

It has also been shown that MASC differentiate into cells that express markers of endothelial cells, but proved that VEGF induced MASC function like endothelial cells. Endothelial cells modify lipoproteins during transport in the artery wall (Adams et al., 2000). Endothelial cells maintain a permeability barrier through intercellular junctions that widen when exposed to hemodynamic forces or vasoactive agents, such as histamine (Rosenberg et al., 1998; Li et al., 1990; Van Rijen et al., 1997; Vischer et al., 2000). Endothelial cells release prothrombotic molecules such as vWF, tissue factor, and plasminogen activator inhibitor to prevent bleeding (Vischer et al., 2000), and regulate egress of leukocytes by changing expression levels of adhesion molecules in response to inflammation (Meager, 1999; Steeber et al., 2001). Endothelium also reacts to hypoxia by producing VEGF and expressing VEGF receptor aimed at increasing vascular density (Kourembanas et al., 1998). Therefore it has been demonstrated that endothelial cells generated from MASC can perform all of these tasks when tested in vitro.

Finally it has been proved that in vitro generated MASC-derived endothelial cells respond to angiogenic stimuli by migrating to the tumor site and contributing to tumor vascularization as well as wound healing in vivo. This finding confirms that endothelial cells generated from MASC have all the functional characteristics of mature endothelium. The degree of contribution of endothelial cells to tumor angiogenesis and neo-angiogenesis was 3545%, levels similar to what has been described for other sources of endothelial cells (Conway et al., 2001; Ribatti et al., 2001). In addition, it has been found that angiogenic stimuli in vivo provided in a tumor microenvironment are sufficient to recruit MASC to the tumor bed and induce their differentiation into endothelial cells that contribute to the tumor vasculature. These studies therefore extend studies reported by other groups demonstrating that cells present in marrow can contribute to new blood vessel formation (Peichev et al., 2000; Lin et al., 2000; Gehling et al., 2000; Asahara et al., 1997), in a process similar to vasculogenesis, precursor responsible for this process has been identified the. This is to our knowledge the first report that identifies a cell present in post-natal BM as a very early progenitor for endothelial cells.

Example 10

Derivation of Neurons

Single adult BM-derived hMASC or mMASC were tested to determine whether they can differentiate ex vivo to functional neurons, as well astrocytes and oligodendrocytes aside from mesodermal cell types. mMASC and hMASC were selected and culture expanded as previously described in Examples 1 and 3, respectively. Human neural progenitor cells (hNPC) were purchased from Clonetics (San Diego, Calif.). hNPC were cultured and differentiated per manufactures' recommendations.

Electrophysiology: Standard whole-cell patch-clamp recording was used to examine the physiological properties of MASC-derived neurons. Voltage-clamp and current-clamp recordings were obtained using a Dagan 3900A patch-clamp amplifier (Dagan Corporation, Minneapolis) which was retrofitted with a Dagan 3911 expander unit. Patch pipettes, made from borosilicate glass, were pulled on a Narishige pipette puller (model PP-83), and polished using a Narishige microforge (model MF-83). Patch pipettes were filled with an intracellular saline consisting of (in mM) 142.0 KF, 7.0 $Na_2SO_4$, 3.0 $MgSO_4$, 1.0 $CaCl_2$, 5.0 HEPES, 11.0 EGTA, 1.0 glutathione, 2.0 glucose, 1.0 ATP (magnesium salt), 0.5 GTP (sodium salt). For most recordings, the fluorescent dye 5,6-carboxyfluorescein (0.5 mm; Eastman Kodak Chemicals) was also added to the pipette solution to confirm visually, using fluorescence microscopy, that the whole-cell patch recording configuration had been achieved. Pipette resistances ranged from 11 to 24 Mohm. The standard extracellular recording saline was comprised of the following (in mM): 155 NaCl, 5.0 KCl, $CaCl_2$, 1.0 $MgCl_2$, 10 HEPES, 5 glucose. For some experiments 1 µM TTX was added to the standard control solution. The pH of the intracellular and extracellular recording solutions was adjusted to 7.4 and 7.8, respectively, using NaOH. All chemicals were from Sigma. PClamp 8.0 (Axon Instruments, Foster City) was used to run experiments, and to collect and store data. The data presented were corrected for a 8.4 mV liquid junctional potential, which was calculated using the JPCALC software package. Off-line analyses and graphical representations of the data were constructed using Clampfit 8.0 (Axon Instruments, Foster. City) and Prism (Graphpad, San Diego).

Transduction: Retroviral supernatant was produced by incubating MFG-eGFP-containing PG13 cells, provided by Dr. G. Wagemaker, U. of Rotterdam, Netherlands (Bierhuizen et al., 1997), with MASC expansion medium for 48 h, filtered and frozen at −80° C. MASC were incubated with retroviral supernatants and 8 µg/ml protamine (Sigma) for 6 h. This was repeated 24 h later. Transduction efficiency was analyzed by FACS.

Gene microarray analysis: RNA was isolated from hMASC, bFGF or FGF-8b+EGF induced cells using the RNeasy mini kit (Qiagene), digested with DNase I (Promega) at 37° C. for 1 h and re-purified using the RNeasy. The [$^{32}$P] dATP labeled cDNA probe, generated according to the manufacturers recommendations, was hybridzed to the Human Neurobiology Atlas Array (Clonetech # 7736-1, Clonetech Laboratories, Palo Alto, Calif., USA) at 68° C. for 18-20 h, followed by 4 washes in 2×SSC, 1% SDS at 68° C. for 30 min each time, 0.1×SSC, 0.5% SDS at 68° C. for 30 min, and once in 2×SSC at room temperature for 5 min. The arrays were read by a phosphorimager screen scanner (Molecular Dynamics, Storm 860) and analyzed using Atlas Image 1.0 (Clontech). Differences between undifferentiated and differentiated cells greater than 2-fold were considered significant.

PCR analysis for retroviral insert: PCR was used o amplify the flanking sequence 3' from the 3' LTR of the MFG vector in the human genomic DNA. DNA from 10$^6$ MASC or endothelial, myoblast or neuroectodermal differentiated progeny was prepared from cells by standard methods. 300 ng of genomic DNA was digested with AscI and a splinkerette linker was ligated to the 5' end (Devon R. S. et al., 1995). The two oligonucleotides used for the splinkerette linker were as follows: aattTAGCGGCCGCTTGAATTttttttgcaaaaa, (the hairpin loop forming sequence is in lower case and the upper case is the reverse complement of the second splinkerette oligo), and agtgtgagtcacagtagtctcgcgttc GAATTAAGCG-GCCGCTA, (the underlined sequence is also the sequence of the linker-specific primer (LS Primer) used for the PCR and RT steps). A 5'-biotin-T7 coupled primer was used that recognizes a sequence in the eGFP gene [Biotin-ggc-cag-tga-att-gta-ata-cpa-ctc-act-ata-ggc-tgg-CAC-ATG-GTC-CTG-CTG-GAG-TTC-GTG-AC; underlined portion shows the minimum promoter sequence needed for efficient in vitro transcription and the upper case is the eGFP specific sequence] and LS primer to amplify the flanking regions for 10 rounds using Advantage 2 polymerase (Clontech). The biotin labeled amplified product was captured using streptavidin-magnetic beads (Streptavidin Magnetic Particles; Roche) and the resultant product was further amplified using the T7 RNA polymerase an approximately 1,000 fold and then DNAase 1 treated. The resultant product was reverse transcribed using the agtgtgagtcacagtagtctcgcgttc splinkerette primer according to the superscript II protocol (Gibco), and subsequently amplified by 30 rounds of nested PCR using the primer for the 3'LTR [ggc caa gaa cag atg gaa cag ctg aat atg]. The flanking sequence in the human genome from endothelium, muscle, and neuroectodermal differentiated cells and undifferentiated MASC was sequenced.

To demonstrate that the same insertion site was present in multiple differentiated progeny, specific primers were generated in the host-flanking genome. Real time PCR amplification (ABI PRISM 7700, Perkin Elmer/Applied Biosystems) was used to quantitate the flanking sequence compared to the eGFP sequence. Reaction conditions for amplification were as follows: 40 cycles of a two step PCR (95° C. for 15 sec, 60° C. for 60 sec) after initial denaturation (95° C. for 10 min.) with 2 µl of DNA solution, 1× TaqMan SYBR GreenUniversal Mix (Perkin Elmer/Applied Biosystems) PCR reaction buffer. Primers used were as follows: Clone A16: LTR primer=CCA-ATA-AAC-CCT-CTT-GCA-GTT-G; Flanking sequence chromosome 7=TCC-TGC-CAC-CAG-AAA-TAA-CC; Clone A 12 chromosome 7 sequence: LTR primer=GGA-GGG-TCT-CCT-CTG-AGT-GAT-T, Flanking sequence=CAG-TGG-CCA-GAT-CTC-ATC-TCA-C; Clone A12 chromosome 1 sequence: LTR=GGA-GGG-TCT-CCT-CTG-AGT-GAT-T; Flanking sequence=GCA-GAC-GAG-GTA-GGC-ACT-TG. The relative amount of the flanking sequence was calculated in comparison with eGFP sequence according to manufacturer's recommendations using the 7700 ABI PRISM Detector Software 1.6.

Neural transplantation: Newborn (P1-P3) male Sprague Dawley rats (Charles River Laboratories) were used in this study. The rats were anaesthetized by cryoanesthesia. The cranium was immobilized using a modified stereotaxic head holder and the scalp reflected to expose the skull. hMASC were harvested with 0.25% trypsin/EDTA, washed twice, and resuspended in PBS. The viability of the hMASC was more than 85%. A 2 μl volume of hMASC suspended in phosphate buffered saline at a concentration of $0.7 \times 10^4$ cells/μl was stereotaxically injected intracerebroventricularly with a tapered glass micropipette attached to a Hamilton syringe using the following coordinates (mm from bregma): AP −0.6, ML 0.8, DV 2.1, toothbar was set at −1. Following the injections, the scalp was sutured and the pups allowed to recover.

Four and 12 weeks after transplantation, the rats were anaesthetized with chloral hydrate (350 mg/kg, i.p.), decapitated the brains removed, frozen in powered dry ice, and stored at −80° C. Fresh frozen brains were sectioned using a cryostat and fixed with 4% paraformaldehyde for 20 min immediately before staining. Sections were incubated for one hour at room temperature with blocking/permeabilization solution consisting of 2% normal donkey serum (Jackson Immuno Labs) and 0.3% triton X. Primary and secondary antibodies were diluted in the same blocking/permeabilization solution for subsequent steps. Primary antibodies (mouse anti human nuclei (1:25), anti human nuclear membrane (1:25) and anti NeuN (1:200) from Chemicon; rabbit anti GFAP (1:250) from DAKO, rabbit anti NF200 (1:300) from Sigma were incubated overnight at 4° C., rinsed 3×10 minutes each in PBS and followed by secondary Cy3 (1:200) anti and FITC (1:100) antibodies (all from Jackson Immuno Labs) for two hours at room temperature. Slides were examined by fluorescence microscopy using a Zeiss Axiovert scope as well as by confocal fluorescence microscopy using a Confocal 1024 microscope.

hMASC Acquire a Neuron, Astrocyte and Oligodendrocyte, Phenotype When Cultured With bFGF.

Neuroectodermal differentiation was done as described in Example 5. Briefly, cells were cultured in FN-coated chamberslides or culture plates with serum-free medium consisting of 60% DMEM-LG, 40% MCDB-201 (Sigma Chemical Co, St Louis, Mo.), supplemented with IX ITS, IX LA-BSA, $10^{-8}$ M dexamethasone, $10^{-4}$ M ascorbic acid 2-phosphate (AA) (all from Sigma), 100 U penicillin and 1,000 U streptomycin (Gibco). In some cultures, we added 100 ng/mL bFGF whereas in other cultures 10 ng/mL EGF+10 ng/mL FGF-8b were added (all from R&D Systems). Cells were not subcultured, but media was exchanged every 3-5 days.

Two weeks after re-plating with bFGF, 26±4% of cells expressed astrocyte (GFAP+), 28±3% oligodendrocyte (MBP+) and 46±5% neuron (NF200+) markers as shown in Table 6.

TABLE 6

Differentiation markers on bFGF and FGF-8b induced hMSC

|  | bFGF (day 7) | bFGF (day 14) | bFGF (day 21) | FGF-8b (day 7) | FGF-8b (day 14) | FGF-8b (day 21) |
|---|---|---|---|---|---|---|
| GFAP | 36 ± 4% | 26 ± 4% | 0 | 0 | 0 | 0 |
| MBP | 35 ± 3% | 28 ± 3% | 4 ± 2% | 0 | 0 | 0 |
| GalC | 30 + x% | 26 ± 5% | 8 ± 3% | 0 | 0 | 0 |
| Nestin | 35 ± 6% | 6 ± 3% | Not tested | 90 ± 10% | 10 ± 6% | Not tested |
| Neuro-D | 20 ± 2% | 0% | Not tested | 50 ± 6% | Not tested | Not tested |
| Tuji | 30 ± 3% | 23 ± 5% | 23 ± 2% | 88 ± 5% | 92 ± 3% | 98 ± 2% |
| PSA-NCAM | 33 ± 2% | 16 ± 3% | Not tested | 40 ± 7% | Not tested | Not tested |
| NF68 | 0 | 26 ± 7% | 22 ± 3% | 0 | 20 ± 3% | Not tested |
| NF160 | 0 | 46 ± 5% | 50 ± 3% | 0 | 65 ± 3% | Not tested |
| NF200 | 0 | 15 ± 2% | 22 ± 5% | 0 | 75 ± 8% | 92 ± 6% |
| NSE | 0 | 40 ± 4% | 82 ± 5% | 0 | 78 ± 3% | 80 ± 8% |
| MAP2-AB | 0 | 40 ± 6% | 80 ± 2% | 0 | 95 ± 4% | 95 ± 3% |
| Tau | 0 | 28 ± 2% | 78 ± 7% | 0 | 93 ± 2% | 92 ± 4% |
| GABA | 0 | 0 | 0 | 0 | 39 ± 4% | 40 ± 2% |
| Parvalbumin | 0 | 0 | 0 | 0 | 28 ± 6% | 35 ± 3% |
| TH | 0 | 0 | 0 | 20 ± 5% | 23 ± 5% | 25 ± 6% |
| DCC | 0 | 0 | 0 | 0 | 25 ± 6% | 28 ± 2% |
| DTP | 0 | 0 | 0 | 0 | 35 ± 7% | 38 ± 3% |
| TrH | 0 | 0 | 0 | 0 | 26 ± 6% | 25 ± 4% |
| Serotonin | 0 | 0 | 0 | 0 | 30 ± 5% | 35 ± 3% |
| Nurrl | 0 | 0 | 0 | 0 | 20 ± 4% | 23 ± 2% |
| c-ret | 0 | 0 | 0 | 0 | 33 ± 3% | 35 ± 5% |

When hMASC were replated at higher cell densities ($2 \times 10^4$ cells/cm$^2$) to induce differentiation, no cells with neuroectodermal phenotype could be detected, suggesting that cell-cell interactions prevent bFGF-induced neuroectodermal differentiation.

The distribution of astrocyte-, oligodendrocyte- and neuron-like cells did not differ when differentiation was induced with hMASC that had undergone 20 or 60 PDs. However, when hMASC expanded for 20 PDs were cultured with bFGF, >50% of cells died while >70% of hMASC culture expanded for >30 PDs survived and acquired a neuron-, astrocyte- or oligodendrocyte-like phenotype. This suggests that not all hMASC can be induced to acquire neural characteristics but that a subpopulation of hMASC that survives long-term in vitro may be responsible for neuronal differentiation. It has been shown that the karyotype of hMASC is normal irrespective of culture duration (Reyes et al., 2001). Differentiation of hMASC into neuroectodermal-like cells is therefore not likely due to transformation of MASC following long-term culture.

Most astrocyte- and oligodendrocyte-like cells died after 3 weeks. Progressive maturation of neuron-like cells was seen throughout culture. After 1 week, bFGF treated hMASC stained positive for NeuroD, Nestin, polysialated neural cell adhesion molecule (PSA-NCAM), and tubulin-β-III (TuJI) (Table 6). After 2 weeks, bFGF treated cells stained positive for NF68, -160, and -200, NSE, MAP2-AB, and Tau. bFGF-induced neurons did not express markers of GABA-ergic, serotonergic or dopaminergic neurons, but expressed glutanate as well as the glutamate-receptors-5, -6 and -7 and N-methyl-D-aspartate (NMDA)-receptor, and $Na^+$-gated voltage channels.

Further confirmation of neuroectodermal differentiation was obtained from cDNA array analysis of two independent hMASC populations induced to differentiate for 14 days with 100 ng/mL bFGF. Expression levels of nestin, otx 1 and otx2Consistent with the immunohistochemical characterization, a >2 fold increase in mRNA for nestin was detected, GFAP, glutamate-receptors 4, 5, and 6, and glutamate, and several sodium-gated voltage channels, but did not detect increases in TH or TrH mRNA levels. A>2 fold increase in mRNA levels was also found for mammalian achaete-scute homolog 1 (MASH I) mRNA, a transcription factor found only in brain (Franco Del Arno et al., 1993) and ephrin-A5 mRNA (O'Leary and Wilkinson, 1999). The astrocyte specific markers GFAP and S100A5, and oligodendrocyte specific markers, myelin-oligodendrocyte glycoprotein precursor and myelin protein zero (PMZ), as well as Huntingtin, and major prion protein precursor mRNA were expressed >2-fold higher after exposure to bFGF. A greater than 2 fold increase was also seen for several glycine receptors, GABA-receptors, the hydroxytryptophan receptor-A and neuronal acetylcholine receptor, glycine transporter proteins, synaptobrevin and synaptosomal-associated protein (SNAP)25. Finally, bFGF induced expression of BDNF and glia-derived neurotrophic factor (GDNF).

Like hMASC, mMASC Acquire a Neuron, Astrocyte and Oligodendrocyte Phenotype when Cultured with bFGF.

MASC derived from other species was tested to determine whether similar results could be obtained. mMASC expanded for 40-90 PDs were replated at 14 cells/cm² in conditions identical to those used for hMASC. After 14 days, mMASC acquired morphologic and phenotypic characteristics of astrocytes (GFAP⁺), oligodendrocytes (MBP⁺) and neurons (NF-200⁺, NSE⁺ and Tau). NF200 and GFAP or MBP were never found in the same cell. In contrast to undifferentiated mMASC, mMASC treated with bFGF were significantly larger and extended processes for >40 μm.

To determine whether neuron-like cells had functional characteristics of neurons, and if bFGF-induced cells showed evidence of voltage-gated $Na^+$ currents a patch clamp was used. No sodium currents or fast spiking behavior was seen in any of the mMASC derived neuron-like cells (n=59), even though some cells expressed calcium currents, and in 4 cells there was evidence of spiking behavior mediated by calcium currents. Thus, bFGF induced cells did not have functional voltage-gated $Na^+$ currents, despite expression of sodium-gated voltage channel mRNA and protein.

hMASC Acquire a Midbrain Dopaminergic, Serotonergic and GABAergic Phenotype When Cultured With EGF and FGF-8b.

FGF-8b, expressed at the mid-hindbrain boundary and by the rostral forebrain, induces differentiation of dopaminergic neurons in midbrain and forebrain and serotonergic neurons in the hindbrain (Ye et al., 1998). In vitro, FGF-8b has been used to induce dopaminergic and serotonergic neurons from murine ES cells (Lee et al., 2000).

hMASC (n=8), expanded=for 20 to 60 PDs, were replated at 2×10⁴ cells/cm² on FN in serum free medium with ITS and AA and with 10 ng/mL FGF-8b and 10 ng/mL EGF. More than 80% of cells survived for 3 weeks. FGF-8b and EGF induced differentiation into cells staining positive for neuronal markers (Table 6) (day 7: PSA-NCAM, Nestin and TuJ1; day 14: NF-68, NF-160, NF-200; and day 21: MAP2-AB, NSE, Tau, and $Na^+$-gated voltage channels) but not oligodendrocytes and astrocytes. In contrast to our observation for bFGF induced differentiation, cells plated at 10⁴ cells/cm² with EGF and FGF-8b did not lead to differentiation. After 2-3 weeks, cells had characteristics of GABAergic (GABA⁺, parvalbumin⁺), dopaminergic (TH⁺, DCC⁺, and DTP⁺) and serotonergic (TrH⁺ and serotonin⁺) neurons (Table 6). Cells also expressed the GABA-A-receptor and glutamate receptors. Cells with a dopaminergic phenotype also stained positive with Abs against the nuclear transcription factor, Nurrl, expressed only in midbrain dopaminergic neurons (Saucedo-Cardenas et al., 1998) as well as the proto-oncogene cRet, a membrane-associated receptor protein tyrosine kinase, which is a component of the glial cell line-derived neurotrophic factor (GDNF) receptor complex expressed on dopaminergic neurons (Trupp et al., 1996). This suggests that FGF-8b induces a phenotype consistent with midbrain dopaminergic neurons.

Again, results from immunohistochemical studies were confirmed by cDNA array analysis on hMASC induced to differentiate for 14 days with FGF-8b+EGF. Consistent with the immunohistochemical characterization, a >2 fold increase in mRNA for TH, TrH, glutamate, several glutamate-receptors, and sodium-gated voltage channels was detected. As parvalbumin and GABA are not present on the array, their expression could not be confirmed by mRNA analysis. Consistent with the almost exclusive neural differentiation seen by immunhistochemnistry, there was no increase in expression of GFAP, S100A5 mRNA nor mRNA for the oligodendrocyte specific marker, PMZ. FGF-8b+EGF induced cells expressed >2 fold more tyrosine kinase receptor (Trk)A, BDNF and GDNF, several glycine-, GABA- and hydroxytryptamine-receptors, and several synaptic proteins.

Coculture with the Glioblastoma Cell Line U87 Enhances Neuron Maturation.

Irrespective of the culture conditions used, hMASC-derived neurons did not survive more than 3-4 weeks in culture. As neither culture contained glial cells after 3 weeks, it is possible that neuronal cells that express both glutamate and glutamate-receptors died due to glutamate toxicity (Anderson and Swanson, 2000). Alternatively, factors required for neural cell survival, differentiation and maturation provided by glial cells might not be present in the cultures (Blondel et al., 2000; Daadi and Weiss, 1999; Wagner et al., 1999). To test this hypothesis, cells from 3-week old FGF-8b+EGF cultures were cocultured with the glioblastoma cell line, U-87, in serum-free medium supplemented with FGF-8b+EGF for an additional 2 weeks.

The glioma cell line, U-87, [American Tissue Cell Collection (Rockville, Md.)] was maintained in DMEM+10% FCS (Hyclone Laboratories, Logan, Utah). Cells from 3-week old FGF-8b+EGF containing cultures were labeled with the lipophylic dye, PKH26 (Sigma), as per manufacturer's recommendations. Labeled cells were replated in FN coated chamber slides in FGF-8b+EGF containing serum free medium together with 1,000 U-87 cells and maintained an additional 2-3 weeks with media changes every 3-5 days. To assure that PKH26 present in MASC-derived cells did not transfer to the U-87 cell line, U-87 cells were cultured in BSA-containing medium and 20 µl PKH26 dye for 7 days. No labeling of glioma cells was detected.

Under these serum-free conditions, U-87 cells ceased to proliferate but survived. hMASC derived neurons were labeled with the membrane dye, PKH26, prior to coculture with U-87 cells to allow us to identify the hMASC-derived cells by fluorescence microscopy. FGF-8b+EGF induced neurons cocultured after 3 weeks with U-87 cells and the same cytokines survived for at least 2 additional weeks. Neurons acquired a more mature morphology with increased cell size as well increased number, length and complexity of the neurites.

The electrophysiological characteristics of PKH26 labeled neural cells derived from hMASC after coculture with U-87 cells by whole-cell current clamp and voltage-clamp after current-injection was evaluated (FIG. 9B). Current-clamp demonstrated spiking behavior in response to injected current in 4/8 of PKH26 labeled hMASC-derived cells present in FGF-8b+EGF/U-87 cultures. The resting membrane potential of spiking and non-spiking cells was −64.9±5.5 mV and −29.7±12.4 mV, respectively. For each cell studied, input resistance of spiking and non-spiking cells was 194.3 (37.3) and 216.3 (52.5) Mohm, respectively. An example of one of the cells in which w observed spiking behavior is shown in FIG. 9B. The top panel shows a family of voltage traces which was elicited from a spiking cell under control conditions. A DC current was first injected in the cell to hold them in the range of −100 to −120 mV. A current injection protocol, as shown in the middle panel, was then used to drive the membrane potential to different levels. As shown in this example, depolarizing current steps that were sufficiently large to bring the cell to threshold for action potential, evoked a single spike. The lower panel shows that the spiking behavior of the cells could be blocked by 1 µM TTX, suggesting that the action potentials are mediated by Na-gated voltage channels. Leak-subtracted current records, obtained in voltage-clamp mode from the same cells (FIG. 9C), demonstrated an inward current that was transient in time course and activated at voltages more positive than −58 mV, as well as outward currents. The transient inward current was blocked reversibly by 1 µM TTX. This pharmacology, together with the transient time course and the voltage-dependent activation of the inward current is typical for voltage-gated $Na^+$ currents, found only in mature neurons and skeletal muscle cells (Sah et al., 1997; Whittemore et al., 1999). Skeletal muscle markers in these neuron-like cells was not detected. These studies suggest that treatment with FGF-8b+EGF and co-culture with glioblastoma cellsfresults innaturation to cells with the fundamental characteristics of excitable neurons, TTX-sensitive voltage-gated $Na^+$ currents.

hMASC Transplanted in Ventricles of Newborn Rats Differentiate in Cells Expressing Astrocyte and Neuronal Markers $1.4×10^4$ hMASC were stereotactically injected in the lateral ventricles of P1-P3 Sprague Dawley rats. After 4 and 12 weeks, animals were sacrificed and analyzed for presence of human cells and evidence of differentiation of hMASC to neuroectoderm. Human cells, identified by staining with a antibodies against human nuclei or human nuclear membrane could be seen in the SVZ up to 400 µm away from the ventricle in animals analyzed after 4 weeks, and after 12 weeks, human cells could also be seen deeper in the brain parenchyma such as in the hippocampus and along the fornix. Some human cells had typical astrocyte morphology and stained positive with anti-GFAP antibodies, whereas other cells stained positive with anti-Neu-N antibodies, NF-200 and anti-human nuclear membrane antibodies. Triple staining showed that human nuclear antigen positive Neu-N positive cells did not coexpress and GFAP.

Summary

The central finding of this work is that single post-natal BM-derived MASC can be induced to differentiate not only into mesodermal cell types but also cells with mature neuronal characteristics, as well as astrocyte and oligodendrocyte characteristics. Time-dependent as well as culture-method-dependent maturation of MASC to cells with neuroectodermal features was shown. Double staining definitively demonstrated that neuronal or glial cells were authentic and results were not due to inappropriately expressed neuronal or glial markers. These results were confirmed at the mRNA level. Retroviral marking studies were used to demonstrate that the neurons, astrocytes and oligodendrocytes were derived from a single MASC that also differentiates into muscle and endothelium, as the sequence of the host cell genomic region flanking the retroviral vector was identical in all lineages. hMASC did not only acquire phenotypic but also electrophysiological characteristics of mature neurons, namely TTX-sensitive voltage-gated $Na^+$ currents. Finally, it was also shown that MASC can differentiate in vivo into cells expressing neuronal and astrocyte markers.

Using retroviral marking of hMASC combined with PCR-based sequencing of the genomic sequence flanking the 3'-LTR of the retroviral insert, it was shown that neurons are derived from the same hMASC that differentiate into astrocytes and oligodendrocytes, as well as into endothelium and muscle (Jordan et al., 1990). This conclusively demonstrates that MASC can, at the single cell level, differentiate to cells of mesodermal and neuroectodermal lineages. The cells with the ability to differentiate not only into mesodermal cell types but also neuroectodermal cell types multipotent adult stem cells, or MASC were re-named. Sanchez-Ramos et al. (Sanchez-Ramos et al., 2000) and Woodbury et al. (Woodbury et al., 2000) showed that populations of human or rodent MSC can express markers of astrocytes and neurons, but not oligodendrocytes in vitro. However, neither study provided evidence that the same cell that acquired neuroectodermal markers could also differentiate into mesodermal cells. Furthermore, neither study showed that cells expressing neuronal markers also acquired functional neuronal characteristics. Thus, although suggestive for neural differentiation, these reports did not conclusively demonstrate neural and glial differentiation from MSC.

It was also shown that hMASC transplanted in the ventricle of newborn rats can migrate in the neurogenic subventricular zone and into the hippocampus where they respond to local cues to differentiate into cells expressing astrocyte and neuronal markers. This model was chosen because migration and differentiation of NSC to specific neuronal phenotypes occurs to a much greater extent when transplantation is done in germinal areas of the brain than in non-neurogenic areas, and when transplants are done in newborn animals compared with adult animals (Bjorklund and Lindvall, 2000; Svendsen and Caldwell, 2000). Although hMASC are multipotent and differentiate into cells outside of the neuroectoderm, hMASC did not form teratomas. The number of cells that had migrated outside the subventricular area was low after 4 weeks, but increased after 12 weeks.

The ease with which MASC can be isolated from postnatal BM, expanded and induced to differentiate in vitro to astrocytes, oligodendrocytes or neuronal cell types may circumvent one of the key problems in NSC transplantation, namely the availability of suitable donor tissue.

Example 11

MASC Differentiation into Hepatocyte-Like Cells

During embryogenesis, the first sign of liver morphogenesis is a thickening of the ventral endodermal epithelium, which occurs between e7.5 and e8.5 in the mouse (Zaret K. S., 2001). Little is known about the signals involved in initial endoderm formation and subsequent endoderm specification. Early in gastrulation (e6-e7) endoderm is not specified, not even in an anterior/posterior direction (Melton D., 1997). However, recent studies showed that ex vivo exposure of endoderm to FGF4 posteriorizes the early endoderm, which is now competent to express hepatic markers (Wells J. M. et al., 1999). By e8.5 in the mouse, definitive endoderm has formed the gut tube and expresses HNF3β (Zaret K. S., 2000). The foregut endoderm is induced to the hepatocyte lineage by acidic (a) FGF and bFGF, both produced by the adjacent cardiac mesoderm (Zaret K. S., 2001), which are required to induce a hepatic fate and not the default pancreatic fate (Zaret K. S., 2001). Basic morphogenetic proteins (BMP's) produced by the transversum mesenchyme are also required as they increase levels of the GATA4 transcription factor which promote the ability of endoderm to respond to FGF's (Zaret K. S., 2001). GATA4 and HNF3β are required for hepatic specification and are important effectors of downstream events leading to hepatocyte differentiation, as they upregulate markers of hepatocyte specific expression such as albumin, among others.

In most instances, mature hepatocytes can undergo several cell divisions and are responsible for hepatic cell replacement. As a result, there has been great controversy about the existence and function of a liver stem cell. During extensive liver necrosis due to chemical injury or when hepatocytes are treated with chemicals that block their proliferation, a population of smaller cells with oval shape, termed oval cells, emerges and proliferates (Petersen, B. E., 2001). These oval cells may constitute the "stem cell" compartment in the liver. Oval cells reside in the smallest units of the biliary tree, called the canals of Herring, from where they migrate into the liver parenchyma (Theise N. D., et al., 1999). Oval cells are bi-potential, giving rise in vitro and in vivo to both hepatocytes and bile ductular epithelium. Oval cells express several hematopoietic markers such as Thy 1.1, CD34, Flt3-receptor, and c-Kit, and also express αFP, CK19, γ-glutamyl-transferase, and OV-6. The origin of oval cells is not known (Petersen, B. E., 2001; Kim T. H. et al, 1997; Petersen, B. E., 2001).

Until recently, it was believed that hepatocytes could only be derived from cells of endodermal origin and their progenitors. However, recent studies suggest that non-endodermal cells may also form hepatocytes in vivo and in vitro (Petersen, B. E., 2001; Pittenger M. F. et al., 1999). Following bone marrow (BM) transplantation, oval cells are derived from the donor BM (Theise N. D., et al., 1999). Transplantation of enriched hematopoietic stem cells (HSC) in FAH$^{-/-}$ mice, an animal model of tyrosenimia type 1, resulted in the proliferation of large numbers of donor LacZ$^+$ hepatocytes and animals had restored biochemical function of the liver (Lagasse E. et al., 2000). Furthermore, single HSC may not only repopulate the hematopoietic system but also contribute to epithelium of lung, skin, liver and gut (Krause D. S. et al., 2001). Exocrine pancreatic tumor cells treated in vitro with dexamethasone (Dex) with or without oncostatin M (OSM) may acquire a hepatocyte phenotype (Shen C. N. et al., 2000). Finally, mouse embryonic stem (ES) cells spontaneously acquire a hepatocyte phenotype, a process that is enhanced by treatment with aFGF, HGF, OSM, and Dex (Hamazaki T. et al., 2001).

It was demonstrated here that single MASC not only differentiate into mesodermal and neuroectodermal cells, but also into cells with morphological, phenotypic and functional characteristics of hepatocytes in vitro.

mMASC, rMASC, and hMASC Acquire a Hepatocyte-Like Phenotype When Cultured With FGF4 and/or HGF.

mMASC, rMASC and hMASC were selected and cultured as described. To determine optimal conditions for MASC differentiation into hepatocyte-like cells, the effect of different extracellular matrix (ECM) components was tested and cytokines known to induce hepatocyte differentiation in vivo or from ES cells (Zaret K. S., 2001) on mMASC or rMASC differentiation to hepatocytes. As differentiation requires cell cycle arrest, the effect of cell density was also tested. To demonstrate differentiation to hepatocyte like cells, cells were stained after 14 days with Abs against albumin, CK18, and HNF3β.

Optimal differentiation of mMASC or rMASC to albumin, CK18 and HNF3β positive epithelioid cells was seen when MASC were plated at $21.5 \times 10^3$ cells/cm$^2$ in the presence of 10 ng/ml FGF4 and 20 ng/ml HGF on Matrigel™ as shown in Table 7A. After 14 days, the percent albumin, CK18 and HNF3β positive epithelioid cells was 61.4±4.7%, and 17.3% of cells were binucleated. When plated on FN, differentiation to CK18 and HNF3 positive epithelioid cells was also seen, even though only 53.1±6.3% of cells stained and fewer (10.9%) binucleated cells were seen.

Culture with either FGF4 or HGF yielded albumin, CK18 and HNF3 positive epithelioid cells, but the percent albumin, CK18 and HNF3β positive cells was higher when mMASC or rMASC were treated with both FGF4 and HGF as shown in Table 7A. Addition of aFGF, bFGF, FGF7, BMP's, or OSM did not increase the percent cells positive for hepatocyte markers, while 1% DMSO and 0.1 mM-10 mM Sodium Butyrate did not support differentiation of mMASC or rMASC to cells positive for hepatocyte markers.

When cell densities between 2.5 and 25×03 cells/cm$^2$ were tested, the highest percent cells with hepatocyte markers was seen in cultures seeded at $21.5 \times 10^3$ cells/cm$^2$. No hepatocyte differentiation was seen when cells were plated at $<12.5 \times 10^3$ cells/cm$^2$.

hMASC were plated at $3-30 \times 10^3$ cells/cm$^2$ on 10 ng/mL FN or 1% Matrigel™ with aFGF, bFGF, FGF7, 1% DMSO, HGF, and/or FGF4. Only cells treated with 10 ng/ml FGF4 alone, 20 ng/ml HGF alone, or a combination of both differentiated into epithelioid cells that expressed albumin, CK18 and HNF3β. hMASC plated at $15-30 \times 10^3$ cell/cm$^2$ differentiated into epithelioid cells whereas hMASC plated at $3 \times 10^3$ cell/cm$^2$ died. Like mMASC or rMASC, the percent albumin, CK18 and HNF3β positive epithelioid cells was higher when hMASC were cultured on Matrigel™ (91.3%±4.4) than on FN (89.5%±5.4), and the percent binucleated cells was higher on Matrigel™ (31.3%) than on FN (28.7%) as shown in Table 7B.

TABLE 7

Optimization of MASC differentiation into hepatocyte like cells.

| | A: Mouse and Rat | | | B: Human | | |
|---|---|---|---|---|---|---|
| | FGF-4 | HGF | FGF4 + HGF | FGF-4 | HGF | FGF-4 + HGF |
| FN | | | | | | |
| Albumin | ++/++ | ++/+ | ++/++ | +++++ | +++++ | +++++ |
| CK18 | ++/++ | ++/+ | +++/++ | +++++ | +++++ | +++++ |
| HNF3β | +++/+++ | +++/+ | ++++/+++ | +++++ | NT | +++++ |
| Matrigel™ | | | | | | |
| Albumin | ++/++ | +/+ | +++/+++ | +++++ | NT | +++++ |
| CK18 | ++/++ | ++/+ | +++/+++ | +++++ | NT | +++++ |
| HNF3β | +++/+++ | +++/++ | ++++/++++ | +++++ | NT | +++++ |
| Collagen | | | | | | |
| Albumin | - | - | - | NT | NT | NT |
| CK18 | - | - | - | NT | NT | NT |
| HNF3β | - | - | - | NT | NT | NT |

− = 0%
+ = 20%,
++ = 30%,
+++ = 40%,
++++ = 60%,
+++++ = 80% cells staining positive for specific markers and
NT = not tested.

Phenotypic Characterization of MASC Differentiation to Hepatocyte-Like Cells

Hepatocyte differentiation was further evaluated over time by immunofluorescence and confocal microscopy for early (HNF3β, GATA4, CK19, αFP) and late (CK18, albumin, HNF1α) markers of hepatocyte differentiation. mMASC or rMASC plated on Matrigel™ with FGF4 and HGF enlarged from 8 μm to 15 μm diameter as shown in Table 8A. On d21-d28, approximately 60% of cells were epithelioid and surrounded by smaller round or spindle shaped cells. Undifferentiated mMASC or rMASC did not express any of the liver specific transcription factors or cytoplasmic markers. After 4 days, cells expressed HNF3β, GATA4 and αFP, low levels of CK 19, and very rare cells stained positive for HNF1α, albumin or CK18. At seven days, the large epithelioid cells stained positive for HNF3β, GATA4, HNF1α with increasing staining for albumin and CK18. Only rare cells expressed αFP. After 14, 21 and 28 days, the large epithelioid cells stained positive for GATA4, HNF3β, HNF1α, CK18 and albumin, but not αFP or CK19. The smaller cells surrounding the nodules of epithelioid cells stained positive for CK19 and αFP.

hMASC was plated on Matrigel™ with FGF4 and HGF or FGF4 alone enlarged from 10-12 μm to 20-30 μm diameter by d21. After 7 days, cells expressed HNF3β, GATA4 and low levels of CK19, while few cells stained positive for albumin or CK18. After 14 and 21 days, >90% of epithelioid cells stained positive for GATA4, HNF3β, HNF1α, HNF4, CK18 and albumin, while only rare cells stained positive for αFP or CK19 as shown in FIG. 10B.

TABLE 8

Immunohistochemistry Pattern of Hepatocyte Marker Expression

| | A: Mouse and Rat | | | | | B: Human | | | | |
|---|---|---|---|---|---|---|---|---|---|---|
| | D4 | D7 | D10 | D14 | D21 | D4 | D7 | D10 | D14 | D21 |
| HNF3β | +/+ | +/+ | +/+ | +/+ | +/+ | NT | + | NT | + | + |
| Gata4 | +/+ | +/+ | +/+ | +/+ | +/+ | NT | + | NT | + | + |
| α-FP | +/+ | +/+ | NT/NT | -/- | -/- | NT | + | NT | - | - |
| HNF1α | -/- | +/+ | NT/NT | +/+ | +/+ | NT | - | NT | + | + |
| Albumin | -/- | +/+ | +/+ | +/+ | +/+ | NT | + | NT | + | + |
| CK18 | -/- | +/+ | +/+ | +/+ | +/+ | NT | - | NT | + | + |

+ = Marker is expressed,
− = Marker is not expressed and
NT = not tested

Hepatocyte-Like Cells are Derived from the Same Single hMASC that Differentiated into Neuroectoderm and Endoderm It has been shown that single mMASC or rMASC differentiate into endothelium, neuroectoderm and CK18 and albumin positive endodermal cells. It has also been shown that single hMASC differentiate into mesoderm and neuroectoderm. The same single hMASC was tested to determine whether they can differentiate into hepatocyte-like cells. MASC were obtained, cultured and expanded as described. For differentiation, mMASC or rMASC were plated at 5-25× $10^3$ cells/cm$^2$ on 0.01-10 μg/ml fibronectin (FN), 0.01-8 μg/ml collagen (Sigma Chemical Co, St. Louis, Mo.), or 1% Matrigel™ (Becton-Dickinson) in serum-free medium [60% low glucose DMEM (DMEM-LG; Gibco-BRL, Grand Island, N.Y.), 40% MCDB-201 (Sigma), supplemented with 1× insulin/transferrin/selenium, 4.7 μg/ml linoleic acid, 1 mg/ml bovine serum albumin (BSA), $10^{-8}$ M dexamethasone, $10^{-4}$ M ascorbic acid 2-phosphate (all from Sigma), 100 U/ml penicillin, 100/ml U streptomycin (Gibco)], with 2% FCS (Hyclone, Logan Utah) and 10 ng/mL each epidermal growth factor (EGF) (Sigma), leukemia inhibitory factor (LIF; Chemicon, Temecula, Calif.), and platelet derived growth factor (PDGF-BB; R&D Systems, Minneapolis, Minn.). hMASC were plated at 15-30×10³ cells/cm² on 0.1 μg/ml FN, or 1% Matrigel™ in the same medium without LIF (Reyes M., 2002). After 8-12 h, media were removed, cells washed twice with phosphate buffered saline (PBS) (Fischer) and cultured in serum-free medium supplemented with 5-50 ng/ml HGF, aFGF, bFGF, FGF4, FGF7, or OSM; or 10 mg/ml dimethyl-sulphoxide (DMSO), or 0.1-1 mM sodium butyrate.

Transduction of hMASC with eGFP was performed using an eGFP-cDNA containing retrovirus and expanded to >5×10⁶ cells. Twenty percent was induced to differentiate into muscle, endothelium, neuroectoderm and endoderm. For clone A16 a single retroviral insertion site was present in undifferentiated MASC as well as mesodermal and neuroectodermal differentiated cells and eGFP⁺ clone A16 MASC differentiated into CK18 and albumin positive cells. The same insertion site was present in FGF4-treated MASC generated from the same cell population (5'-TAG CGGCCGCT-TGAATTCGAACGCGAGACTACTGTGACT CACACT-3', Chromosome 7), proving that single hMASC differentiate into endoderm aside from mesoderm and neuroectoderm.

Quantitative RT-PCR Demonstrates that FGF4 and HGF Induces Hepatocyte Specification and Differentiation.

Hepatocyte differentiation by quantitative RT-PCR was confirmed for early (HNF3β, GATA4, CK19, αFP) and late (CK18, albumin, HNF1α, cytochrome P450) markers of hepatocyte differentiation. RNA was extracted from 3×10⁵ MASC or MASC induced to differentiate to hepatocytes. mRNA was reverse transcribed and cDNA was amplified as follows: 40 cycles of a two step PCR (95° C. for 15", 60° C. for 60") after initial denaturation (95° C. for 10') with 2 μl of DNA solution, 1× TaqMan SYBR Green Universal Mix PCR reaction buffer using a ABI PRISM 7700 (Perkin Elmer/Applied Biosystems). Primers used for amplification are listed in Table 9.

TABLE 9

Primers used

| Primer Name | Primers |
|---|---|
| MOUSE | |
| HNF1α | S: 5'-TTCTAAGCTGAGCCAGCTGCAGACG-3' <br> A: 5'-GCTGAGGTTCTCCGGCTCTTTCAGA-3' |
| HNF3β | S: 5'-CCAACATAGGATCAGATG-3' <br> A: 5'-ACTGGAGCAGCTACTACG-3' |
| GATA4 | S: 5'-AGGCATTACATACAGGCTCACC-3' <br> A: 5'-CTGTGGCCTCTATCACAAGATG-3' |
| CK18 | S: 5'-TGGTACTCTCCTCAATCTGCTG-3' <br> A: 5'-CTCTGGATTGACTGTGGAAGTG-3' |
| CK19 | S: 5'- CATGGTTCTTCTTCAGGTAGGC-3' <br> A: 5'- GCTGCAGATGACTTCAGAACC -3' |
| Albumin | S: 5'-TCAACTGTCAGAGCAGAGAAGC-3' <br> A: 5'-AGACTGCCTTGTGTGGAAGACT-3' |
| αFP | S: 5'-GTGAAACAGACTTCCTGGTCCT-3' <br> A: 5'-GCCCTACAGACCATGAAACAAG-3' |
| TTR | S: 5'-TCTCTCAATTCTGGGGGTTG-3' <br> A: 5'-TTTCACAGCCAACGACTCTG-3' |
| Cyp2b9 | S: 5'-GATGATGTTGGCTGTGATGC-3' <br> A: 5'-CTGGCCACCATGAAAGAGTT-3' |

TABLE 9-continued

Primers used

| Primer Name | Primers |
|---|---|
| Cyp2b13 | S: 5'-CTGCATCAGTGTATGGCATTTT-3' <br> A: 5'-TTTGCTGGAACTGAGACTACCA-3' |
| HUMAN | |
| αFP | S: 5'-TGCAGCCAAAGTGAAGAGGGAAGA-3' <br> A: 5'-CATAGCGAGCAGCCCAAAGAAGAA-3' |
| Albumin | S: 5'-TGC TTG AATGTGCTGATGACAGGG -3' <br> A: 5'-AAGGCAAGTCAGCAGGCATCTCATC-3' |
| CK19 | S: 5'-ATGGCCGAGCAGAACCGGAA-3' <br> A: 5'-CCATGAGCCGCTGGTACTCC-3' |
| GK18 | S: 5'-TGGTACTCTCCTCAATCTGCTG-3' <br> A: 5'-CTCTGGATTGACTGTGGAAGT-3' |
| CYP1B1 | S: 5'-GAGAACGTACCGGCCACTATCACT-3' <br> A: 5'-GTTAGGCCACTTCAGTGGGTCATGAT-3' |
| CYP2B6 | S: 5'-GATCACACCTATATCCCCGGA-3' <br> A: 5'-CACCCTACCACCCATGACCG-3' |
| RAT | |
| HNF1α | S: 5'-AGCTGCTCCTCCATCATCAGA-3' <br> A: 5'-TGTTCCAAGCATTAAGTTTTCTATTCTAA-3' |
| HNF3β | S: 5'-CCTACTCGTACATCTCGCTCATCA-3' <br> A: 5'-CGCTCAGCGTCAGCATCTT-3' |
| CK18 | S: 5'-GCCCTGGACTCCAGCAACT-3' <br> A: 5'-ACTTTGCCATCCACGACCTT-3' |
| CK19 | S: 5'-ACCATGCAGAACCTGAACGAT-3' <br> A: 5'-CACCTCCAGCTCGCCATTAG-3' |
| Albumin | S: 5'-CTGGGAGTGTGCAGATATCAGAGT-3' <br> A: 5'-GAGAAGGTCACCAAGTGCTGTAGT-3' |
| αFP | S: 5'-GTCCTTTCTTCCTCCTGGAGAT-3' <br> A: 5'-CTGTCACTGCTGATTTCTCTGG-3' |
| TTR | S: 5'-CAGCAGTGGTGCTGTAGGAGTA-3' <br> A: 5'-GGGTAGAACTGGACACCAAATC-3' |
| CYP2b1 | S: 5'-GAGTTCTTCTCTGGGTTCCTG-3' <br> A: 5'-ACTGTGGGTCATGGAGAGCTG -3' | mRNA levels were normalized using β-actin (mouse and human) or 18S (rat) as housekeeping genes and compared with mRNA levels in freshly isolated rat or mouse hepatocytes, rat hepatocytes cultured for 7 days, or mRNA from human adult liver RNA purchased from Clontech, Palo Alto, Calif.

Figure 10:
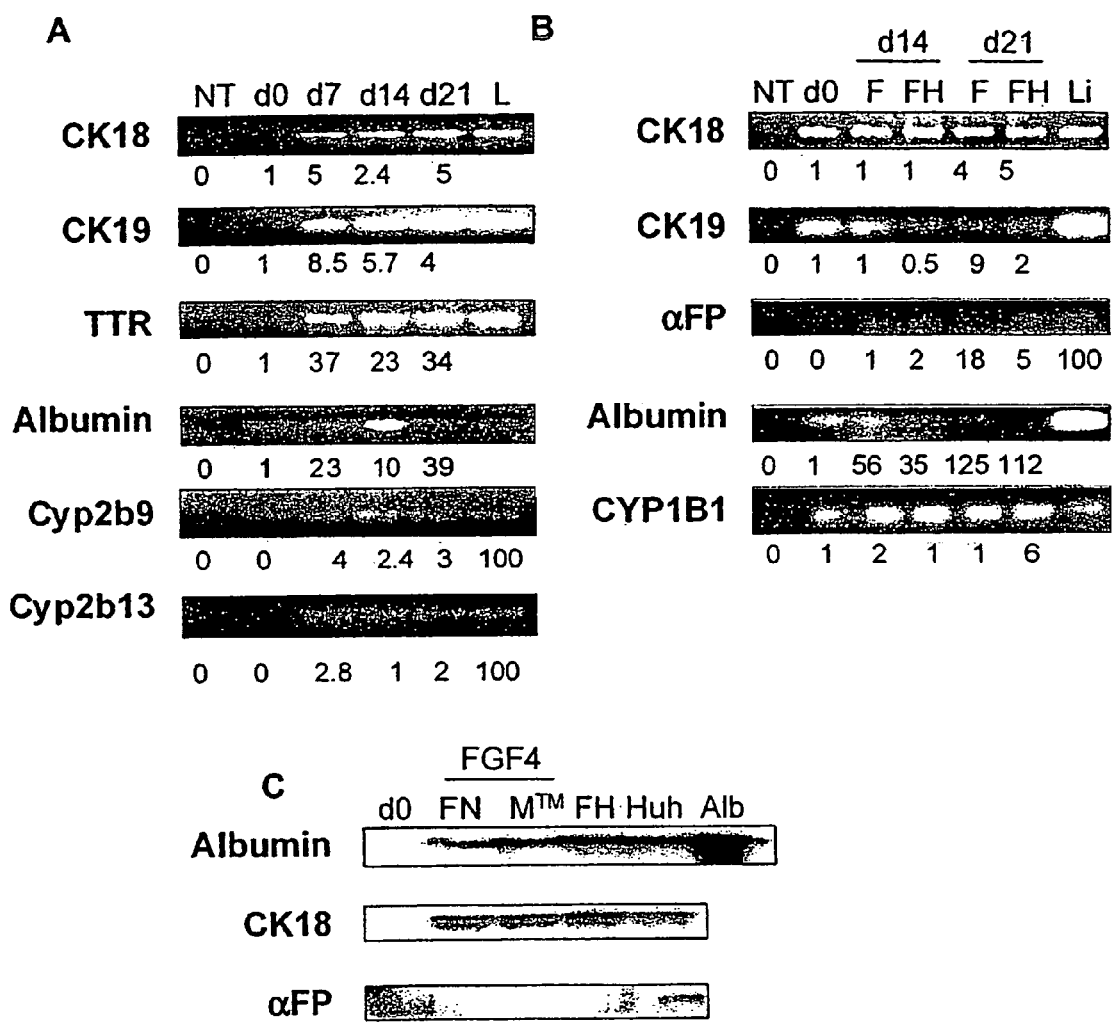
FIG. 10 shows quantitative RT-PCR and Western blot analysis confirming the hepatocyte-like phenotype. Panels A and B show mMASC (A) and hMASC (B) cultured on Matrigel™ with FGF4 and HGF or FGF4 alone for 21 and 28 days respectively. For αFP, Cyp2b9 and Cyp2b13, numbers under the blots are relative to mRNA from liver, as no transcripts were detected in undifferentiated MASC. Li=mouse or human liver mRNA; NT=no-template. Representative example of 5 mouse and 1 human studies, Panel C shows hMASC (B) cultured on Matrigel™ with FGF4 and HGF or FGF4 alone for 21 days. FH=FGF4 and HGF-induced hMASC on Matrigel™, Huh=Huh7 cell line used as control.

On d0, mMASC and rMASC expressed low levels of albumin αFP, CK18, CK19, TTR, HNF3β, HNF1α and GATA4 mRNA, but no CYP2B9 and CYP2B13 (mouse) or CYP2B1 (rat) mRNA (FIG. 10). Following treatment of mMASC or rMASC with FGF4 and HGF, expression of HNF3β and GATA4 mRNA increased on d2, became maximal by d4, decreasing slightly and leveling off by d 14. mRNA for αFP, and CK19 increased after d2, and became maximal by d4 and decreased thereafter. TTR mRNA increased after d4, was maximal by d7 and leveled off. CK18, Albumin, HNF1α and P450 enzyme mRNA increased after d7 and was maximal on d14. Between d14 and d21, FGF4 and HGF induced MASC expressed albumin, TTR, CK18, CYP2B9 and CYP2B 13 (mouse) and CYP2B1 (rat) mRNA.

Undifferentiated hMASC expressed low levels of albumin, CK18, and CK19, CYP1B1, but not αFP (FIG. 10) and CYP2B6 mRNA. Levels of albumin, CK18, CK19, CYP1B1 mRNA increased significantly in hMASC cultured with FGF4 alone or with FGF4 and HGF for 14 days compared to day 0 (MASC) cultures. Levels of albumin, CK18 and CYP1B1 mRNA continued to increase and were higher on d28. Although, CYP1B1 is not a specific hepatocyte marker, its upregulation suggests hepatocyte commitment and maturation. Low levels of CYP2B6, 0.5% to 1.0% of fresh liver mRNA's could be seen on d14 and d21 but not d0. mRNA levels of immature hepatocyte markers (CK19 and αFP) decreased as differentiation progressed and were higher in cultures induced with FGF4 alone, whereas mRNA levels for mature hepatocytes (CK18 and albumin) were higher in FGF4 and HGF-induced hMASC.

Western Blot Demonstrates that FGF4+HGF Induces Hepatocyte Specification and Differentiation Expression of hepatocyte-specific genes was also confirmed by Western Blot and performed as described by Reyes et al. (2000). Abs to αFP, human albumin, CK18 were diluted 1:1000 in blocking buffer. Goat anti-β-actin (1:1000) was from Santa Cruz. Secondary Abs were HRP-linked goat anti-mouse and HRP-linked donkey anti-goat (Amersham, Arlington Heights). ECL was performed according to manufacturers instructions (Amersham). Undifferentiated hMASC did not express CK18, albumin, or αFP protein (FIG. 10B). After treatment for 35 days with FGF4 alone or FGF4 and HGF, hMASC expressed albumin and CK18, but not αFP, consistent with the histochemical analysis.

mMASC, rMASC and hMASC Acquire Hepatocyte Functional Activity

Five different assays were used to determine whether cells with morphologic and phenotypic characteristics of hepatocytes also had functional hepatocyte attributes.

Urea production and secretion by hepatocyte-like cells was measured at various time points throughout differentiation. Urea concentrations were determined by colorimetric assay (Sigma Cat. 640-1) per manufacturer's instructions. Rat hepatocytes grown in monolayer and fetal mouse liver buds were used as positive controls, and culture medium as negative control. The assay can detect urea concentrations as low as 10 mg/ml. As the assay also measures ammonia, samples were assessed before and after urease addition.

No urea or ammonia was detected in culture medium alone. Undifferentiated MASC did not produce urea. Following treatment with FGF4 and HGF, urea production by MASC increased in a time dependent manner. The time course for urea production in mouse and rat cultures was similar. For hMASC treated with FGF4 and HGF, urea was not detected on d4, was similar to mouse and rat cultures by d12, and exceeded that in mouse or rat cultures on d21. Levels of urea produced by MASC-derived hepatocytes were similar to that in monolayer cultures of primary rat hepatocytes. For all three species, significantly more urea was produced by cells differentiated on Matrigel™ compared to FN.

Albumin production was measured at various time points throughout the differentiation. Rat albumin concentrations were determined by a competitive enzyme linked immunoassay (ELISA) described previously (Tzanakakis E. S., et al., 2001; Wells J. M. et al., 2000). Human and mouse albumin concentrations were determined using a similar ELISA method with substitution of human or mouse albumin and anti-human or anti-mouse albumin Abs for the rat components where appropriate. Peroxidase conjugated anti-human-albumin and reference human albumin were from Cappel. Peroxidase conjugated and affinity purified anti-mouse albumin and reference mouse albumin were from Bethyl Laboratories (Montgomery, Tex.). To ensure specificity of the ELISA, human, mouse, and rat Abs were incubated for 2 hrs at 37° C. with 3% BSA in distilled water ($dH_2O$). ELISA's had a sensitivity of at least 1 ng/ml.

Undifferentiated MASC did not secrete albumin. Following treatment with FGF4 and HGF, mMASC, rMASC and hMASC produced albumin in a time dependent manner. As was seen for urea production, MASC differentiated on Matrigel™ produced higher amounts of albumin than when cultured on FN. Mouse, rat, and human cells secreted similar levels of albumin, even though albumin was not detected in human cultures on d3. Levels of albumin produced by mouse, rat and human MASC-derived hepatocytes were similar to those seen in monolayer cultures of primary rat hepatocytes.

Cytochrome P450 activity was next assessed in aggregates of MASC-derived hepatocytes and primary rat liver hepatocyte spheroids using the PROD assay. mMASC-hepatocyte aggregates were formed by plating d14 FGF4 and HGF treated mMASC at $5 \times 10^4$ cells/cm$^2$ on non-tissue culture plates, which were placed on a shaker at 10 revolutions per minute for 5 h. Cell aggregates were transferred to Primaria™ dishes and allowed to compact for 4 days in the presence or absence of 1 mM phenobarbital. hMASC-hepatocyte aggregates were formed by hanging drop method. Briefly, $10^3$ hMASC treated for 24 days with FGF4 and HGF were placed into 100 μL drops with or without 1 mM phenobarbital. After 4 days, aggregates were collected and cytochrome P450 activity assessed by PROD assay. Pentoxyresorufin (PROD) (Molecular Probes, Eugene, Oreg.) is O-dealkylated by Cytochrome P450, changing a non-fluorescent compound into a fluorescent compound, resorufin (Tzanakakis E. S. et al., 2001). Fluorescence intensity caused by PROD metabolism consequently estimates cytochrome P450 (CYP) activity. Assessment and detection of resorufin in situ was performed using confocal microscopy as described (Tzanakakis E. S. et al., 2001).

No PROD activity was seen in aggregates of undifferentiated mMASC or hMASC. However, mMASC (18 days with FGF4 and HGF) and hMASC (28 days, FGF4 alone) induced to form aggregates had significant PROD activity. PROD activity in MASC-derived hepatocyte aggregates was similar to that of primary rat hepatocyte aggregates. A number of different cells have P450 activity, but P450 activity up-regulation by phenobarbital is only seen in hepatocytes. Therefore, P450 was also tested in the presence or absence of phenobarbital. Without phenobarbital, several P450 enzymes partially participate in PROD metabolism giving an inflated fluorescence value for those samples. In contrast, in the phenobarbital induced aggregates, PROD activity is almost wholly metabolized by mouse cytochromes Cyp2b9, Cyp2b10, and Cyp2b13, rat cytochrome Cyp2b1/2 (Tzanakakis E. S. et al., 2001), and in human, by CYP2B6. Therefore increased fluorescent activity is smaller than the actual increase in the protein expression of the stated cytochrome P450 enzymes. When aggregates were cultured for 96 hours with phenobarbital, a 32% to 39% increase in PROD activity was seen, suggesting presence of functional hepatocyte specific Cyp2b9, Cyp2b10, and Cyp2b13 in mMASC and CYP2B6 in hMASC-derived hepatocytes.

MASC-derived hepatocytes were also assessed for their ability to take up LDL by incubating FGF4 treated hMASC with LDL-dil-acil. Cells were co-labeled either with anti-CK18 or anti-Pan-CK and HNF-3β or GATA4 Abs. After 7 days, low level uptake of a-LDL was detected, which increased to become maximal on d21.

Figure 11:
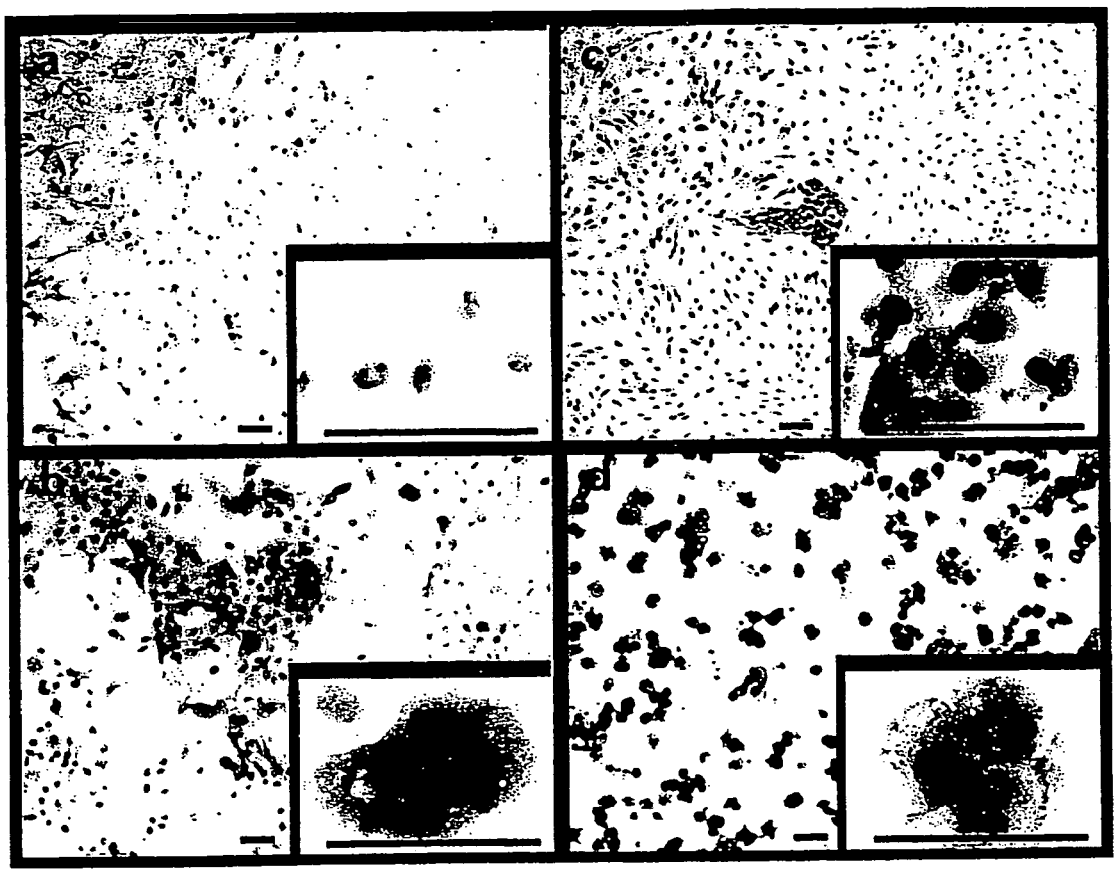
FIG. 11 shows a photomicrograph of hepatocyte-like cells. MASC induced by FGF4 produce glycogen. Glycogen storage is seen as accumulation of dark staining (Representative example of 3 studies). Scale bar=25 μm.

Another metabolic function of hepatocytes is glycogen production or gluconeogenesis. The levels of glycogen storage were analyzed by periodic acid Schiff (PAS) staining of FGF4 and HGF induced mouse MASC and FGF induced hMASC at d3, d7, d14, and d21. For PAS, slides were oxidized in 1% periodic acid for 5' and rinsed 3 times in $dH_2O$. Afterwards slides were treated with Schiff's reagent for 15', rinsed in $dH_2O$ for 5-10', stained with Mayer's hematoxylin for 1' and rinsed in $dH_2O$. Glycogen storage was first seen by d14 and maximum levels were seen after d21 (FIG. 11).

Hepatocyte Isolation and Culture

Hepatocytes were harvested from 4-6 week old male Sprague-Dawley rats as described (Seglen P. O., 1976). Hepatocyte viability after the harvest ranged from 90-95%. Hepatocytes were cultured as described (Tzanakakis E. S. et al., 2001; Tzanakakis E. S. et al., 2001). To form a monolayer, hepatocytes were cultured on 35 mM Fischer culture plates (Fischer Scientific, Pittsburgh, Pa.) coated with 8 g/cm² collagen (Cohesion Technologies, Palo Alto, Calif.). To form spheroids, hepatocytes were cultured on 35-mm Primaria™ dishes (Becton Dickinson). Under both conditions, seeding density was $5 \times 10^4$ cells/cm². 12 h after initial plating, medium was changed to remove dead and unattached cells. Medium was replaced every 48 hours thereafter.

Summary

It has been shown that a single post-natal mouse, rat and human BM-derived MASC can differentiate in vitro into an endodermal cell type with hepatocyte phenotype and function. MASC, cultured under hepatocyte differentiation conditions, expressed in a time-dependent fashion primitive and mature hepatocyte markers, shown by immunofluorescence microscopy of double and triple labeled cells. The protein expression profile was hepatocyte specific and not spurious, as non-hepatocyte markers were not co-expressed with hepatocyte antigens. Results from immunohistochemistry were confirmed by Western blot. In addition, RT-PCR corroborated upregulation of the transcription factors HNF3β and GATA4 known to be important in endoderm specification and transcription factors required for subsequent hepatocyte differentiation, such as HNF3β, and cytoplasmic proteins such as CK19, CK18, αFP and albumin.

Although it was shown that FGF4 alone or both FGF4 and HGF induced MASC into cells with morphological and phenotypic characteristics of hepatocytes, this alone does not prove that cells have differentiated into hepatocytes unless one can demonstrate acquisition of functional characteristics of hepatocytes. Therefore, several functional tests were done in combination to identify functional hepatocytes. mMASC, rMASC or hMASC produced urea and albumin, contained phenobarbital inducible cytochrome P450 activity, could take up Dil-acil-LDL, and contained glycogen granules. Although urea production is characteristic of hepatocyte activity, kidney tubular epithelium also produces urea (Hedlund E. et al., 2001). In contrast, albumin production is a specific test for the presence and metabolic activity of hepatocytes (Hedlund E. et al., 2001). Cytochrome P450, although found in hepatocytes, is also present in many other cell types (Jarukamjom K. et al., 1999). However, Cyp2b1 activity in rat (Tzanakakis E. S. et al., 2001), Cyp2b9 and Cyp2b13 in mouse (Li-Masters T. et al., 2001; Zelko I. Et al., 2000), and CYP2B6 in human is considered relatively hepatocyte specific. Presence of these forms of P450 was shown by RT-PCR. The specificity for hepatocytes is enhanced further when P450 activity is inducible by phenobarbital (Rader D. J. et al., 2000), as shown. Although LDL uptake is seen in hepatocytes (Oh S. H. et al., 2000), other cells such as endothelium have a similar capability (Avital I. et al., 2001). Finally, only hepatocytes can generate and store glycogen. When taken together, these functional tests demonstrate that MASC from mouse, rat or humans treated in vitro with FGF4 and HGF not only express hepatocyte markers but also have functional characteristics consistent with hepatocyte metabolic activities.

Several studies have shown that BM derived cells may differentiate into hepatocyte-like cells in vivo and in vitro (Petersen B. E. et al., 1999; Theise N. D. et al., 2000; Krause D. S. et al., 2001; Pittenger M. F. et al., 1999; Wang S. et al., 2001; Lagasse E. et al., 2000). However, most studies have not addressed the phenotype of the BM cell that differentiates into cells with hepatocyte phenotype. It is unknown whether the cells staining positive for hepatocyte markers had functional characteristics of hepatocytes, and whether cells that differentiate into hepatocytes can also differentiate into mesodermal cells, such as hematopoietic cells. Lagasse et al. demonstrated that $cKit^+Thy_1^{low} Sca1^+Lin^{+-}$ cells present in murine BM differentiate into cells with not only hepatocyte phenotype but also hepatocyte function (Lagasse E. et al., 2000). Even though such results could be seen when as few as 50 cells were transplanted, this study did not prove that the same cell that differentiates into hematopoietic cells also differentiates into hepatocytes. Krause et al showed that a single cell can repopulate the hematopoietic system and give rise to rare hepatocytes. However, no functional assessment of the hepatocytes was done (Krause D. S. et al., 2001). Avital et al recently published that $β_2m^-$, $Thy-1^+$ cells in mouse BM express albumin, HNF4, C/EBPα, and Cytochrome P450 3A2 mRNA and protein (Wilmut I., et al., 1997), a phenotype of hepatocyte progenitors usually found in the liver. Thus, presence of such hepatocyte progenitor cells in BM could explain the in vivo differentiation of bone marrow into hepatocytes noted in recent studies (Krause D. S. et al., 2001; Lagasse E. et al., 2000).

To address the question whether cells giving rise to functional hepatocyte-like cells also give rise to other cell types, retroviral marking was used (Reyes M. et al., 2001; Jiang Y., 2002). It has been recently shown that cells expressing albumin, CK18 and HNF1α can be generated from the same mMASC and rMASC that differentiate into cells with endothelial and neuroectodermal phenotype (Jiang Y., 2002). It is confirmed that similar results are seen for hMASC. Extending recently published studies demonstrating derivation of cells with mesodermal and neuroectodermal phenotype and function from single hMASC (Reyes M., 2002), it is shown here that the same single hMASC also differentiates into cells with hepatocyte morphology and phenotype. Thus, it is demonstrated for the first time that MASC that do not express hepatocyte markers and have no functional hepatocyte activity exist in BM, which depending on the culture conditions, acquire a hepatocyte phenotype and functional characteristics of hepatocytes, or phenotypic and functional characteristics of mesodermal and neuroectodermal cells.

Example 12

Transplantation of LacZ Transgenic MASC to Treat Hemophiliac Mice

MASC were derived from ROSA26 mice containing the β-gal/NEO transgene ($10^6$ cells/mouse) and were I.V. injected into hemophiliac mice (N=5) without prior irradiation. The animals were sacrificed at 1 (N=2) and 2 months (N=3) post-MASC transplantation. Bone marrow cytospins and frozen sections of liver, spleen, skeletal muscle, heart, lung and intestine were stained for presence of β-gal antigen using a FITC-conjugated anti-β-gal antibody and pan-cytokeratin or CD45. Tissues were also analyzed by Q-PCR for the β-gal gene as described in Example 6.

Preliminary analysis indicates that one of the three animals (M3) analyzed at 2 months post-injection had 0.1% of pulmonary epithelial cells derived from the donor cells by immunohistochemistry and Q-PCR. Immunohistochemistry also showed that animal M5 had <1% engraftment of CD45+ donor cells in the spleen, marrow and intestine. Tissues of the animal M4 had some donor derived cells on immunohistochemistry; PCR data on this animal is pending.

All publications, patents and patent applications are incorporated herein by reference as though individually incorporated by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

REFERENCES

Adams, R. H., and Klein, R. (2000). Eph receptors and ephrin ligands. Essential mediators of vascular development. *Trends Cardiovasc Med.* 10:183-188.

Alison, M., and Sarraf, C. (1998). Hepatic stem cells. *J Hepatol* 29: 678-83.

Alizadeh, A. A., M. B. Eisen, R. E. Davis, C. Ma, I. S. Lossos, A. Rosenwald, J. C. Boldrick, H. Sabet, T. Tran, X. Yu, J. I. Powell, L. Yang, G. E. Marti, T. Moore, J. J. Hudson, L. LU. D. B. Lewis, R. Tibshirani, G. Sherlock, W. C. Chan, T. C. Greiner, D. D. Weisenburger, J. O. Armitage, R. Warnke, and L. M. Staudt. 2000. Distinct types of diffuse large B-cell lymphoma identified by gene expression profiling. *Nature.* 403:503-511.

Anderson, C. M., and Swanson, R. A. (2000). Astrocyte glutamate transport: review of properties, regulation, and physiological functions. *Glia* 31:1-14.

Anderson, D. J., Gage, F. H., and Weissman, I. L. (2001). Can stem cells cross lineage boundaries? *Nat Med.,* 393-5.

Arsenijevic, Y., and Weiss, S. (1998). Insulin-like growth facor-I is a differentiation factor for postmitotic CNS stem cell-derived neuronal precursors: distinct actions from those of brain-derived neurotrophic factor. *J Neurosci* 18:118-28.

Asahara, T., Masuda, H., Takahashi, T., Kalka, C., Pastore, C., Silver, M., Kearne, M., Magner, M., and Isner, J. M. (1999). Bone marrow origin of endothelial progenitor cells responsible for postnatal vasculogenesis in physiological and pathological neovascularization. *Circ Res* 85:221-8.

Asahara, T., Murohara, T., Sullivan, A., Silver, M., van der Zee, R., Li, T., Witzenbichler, B., Schatteman, G., and Isner, J. (1997). Isolation of putative progenitor endothelial cells for angiogenesis. *Science* 275, 964-967.

Avital, I., Inderbitzin, D., Aoki, T., Tyan, D. B., Cohen, A. H., Ferraresso, C., Baumhueter, S., Dybdal, N., Kyle, C., and Lasky, L. (1994). Global vascular expression of murine CD34 a sialomucin-like endothelial ligand for L-selectin. *Blood* 84:2554.

Ben-Shushan, E., Thompson, J. R., Gudas, L. J., and Bergman, Y. (1998). Rex-1, a gene encoding a transcription factor expressed in the early embryo, is regulated via Oct-3/4 and Oct-6 binding to an octamer site and a novel protein, Rox-1, binding to an adjacent site. *Mol Cell Biol* 18:1866-78.

Bierhuizen, M. F., Westerman, Y., Visser, T. P., Dimjati, W., Wognum, A. W., and Wagemaker, G. (1997). Enhanced green fluorescent protein as selectable marker of retroviral-mediated gene transfer in immature hematopoietic bone marrow cells. *Blood* 90:3304-15.

Bjorklund, A., and Lindvall, O. (2000). Cell replacement therapies for central nervous system disorders. *Nat Neurosci* 3: 537-44.

Bjornson, C., R. Rietze, B. Reynolds, M. Magli, and A. Vescovi. (1999). Turning brain into blood: a hematopoietic fate adopted by adult neural stem cells in vivo. *Science.* 283: 354-357.

Blondel, O., Collin, C., McCarran, W. J., Zhu, S., Zamostiano, R., Gozes, I., Brenneman, D. E., and McKay, R. D. (2000). A glia-derived signal regulating neuronal differentiation. *J Neurosci.* 20:8012-20.

Bradley, A. (1987). Production and analysis of chimaeric mice; In Teratocarcinomas and ES Cells: A Practical Approach. E. J. Robertson, ed. Oxford: IRL Press, 113-151.

Brazelton, T. R., Rossi, F. M. V., Keshet, G. I., and Blau, H. E. (2000). From Marrow to Brain: Expression of Neuronal Phenotypes in Adult Mice. *Science* 290:1775-1779.

Bruder, S., et al., U.S. Pat. No. 5,736,396

Brustle, O., Jones, K., Learish, R., Karram, K., Choudhary, K., Wiestler, O., Duncan, I., and McKay, R. (1999). ES Cell-Derived Glial Precursors: A Source of Myelinating Transplants. *Science* 285:754-6.

Brustle, O., Spiro, A. C., Karram, K., Choudhary, K., Okabe, S., and McKay, R. D. (1997). ES cells differentiate into oligodendrocytes and myelinate in culture and after spinal cord transplantation. *Proc. Natl. Acad. Sci. USA* 94:14809-14814.

Butler, D., (1999) FDA warns on primate xenotransplants. *Nature* 398:549.

Caplan, A., et al., U.S. Pat. No. 5,486,359
Caplan, A., et al., U.S. Pat. No. 5,811,094
Caplan, A., et al., U.S. Pat. No. 5,837,539

Cassiede P., Dennis, J. E., Ma, F., Caplan, A. I., (1996). Osteochondrogenic potential of marrow mesenchymal progenitor cells exposed to TGF-beta 1 or PDGF-BB as assayed in vivo and in vitro. *J Bone Miner Res.* 9:1264-73.

Cereghini, S. (1996). Liver-enriched transcription factors and hepatocyte differentiation. *FASEB J.* 10:267-82.

Choi, K. (1998). Hemangioblast development and regulation. *Biochem Cell Biol.* 76:947-956.

Choi, K., M. Kennedy, A. Kazarov, J. C. Papadimitriou, and G. Keller. (1998). A common precursor for hematopoietic and endothelial cells. *Development.* 125:725-732.

Ciccolini, F., and Svendsen, C. N. (1998). Fibroblast growth factor 2 (FGF-2) promotes acquisition of epidermal growth factor (EGF) reponsiveness in mouse striata] precursor cells: Identification of neural precursors responding to both EGF and FGF-2. *J Neuroscience* 18:7869-7880.

Clarke, D. L., Johansson, C. B., Wilbertz, J., Veress, B., Nilsson, E., Karlstrom, H., Lendahl, U., and Frisen, J. (2000). Generalized potential of adult NSCs. *Science* 288: 1660-3.

Conway, E. M., Collen, D., and Carmeliet, P. (2001). Molecular mechanisms of blood vessel growth. *Cardiovasc Res.* 49:507-521.

Corbeil, D., Roper, K., Hellwig, A., Tavian, M., Miraglia, S., Watt, S. M., Simmons, P. J., Peault, B., Buck, D. W., and Huttner, W. B. (2000). The human AC 133 HSC antigen is also expressed in epithelial cells and targeted to plasma membrane protrusions. *J Biol. Chem.* 275:5512-5530.

Crosby, H. A., Kelly, D. A., and Strain, A. J. 2001. Human hepatic stem-like cells isolated using c-kit or CD34 can differentiate into biliary epithelium. *Gastroenterology.* 120:534-544.

Daadi, M. M., and Weiss, S. (1999). Generation of tyrosine hydroxylase-producing neurons from precursors of the embryonic and adult forebrain. *J. Neurosci.* 19:4484-97.

Dahlstrand, J., Lardelli, M., and Lendahl, U. (1995). Nestin mRNA expression correlates with the central nervous system progenitor cell state in many, but not all, regions of developing central nervous system. *Brain Res Dev Brain Res.* 84:109-29.

Devon R. S., Porteous D. J., and J., B. A. (1995). Splinkerettes improved vectorettes for greater efficiency in PCR walking. *Nucleic Acids Res* 23:1644-1645.

DiGuisto, et al., U.S. Pat. No. 5,681,599

Doetsch, F., Caille, I., Lim, D. A., Garcia-Verdugo, J. M., and Alvarez-Buylla, A. (1999). Subventricular zone astrocytes are NSCs in the adult mammalian brain. *Cell* 97:703-716.

Eliceiri, B. P., and Cheresh, D. A. (2000). Role of alpha v integrins during angiogenesis. *Cancer J Sci Am.* 6, Suppl 13:S245-249.

Evans, et al., (1992). *J. Am. Med. Assoc.,* 267:239-246.

Faloon, P., Arentson, E., Kazarov, A., Deng, C. X., Porcher, C., Orkin, S., and Choi, K. (2000). Basic fibroblast growth factor positively regulates hematopoietic development. *Development.* 127:1931-1941.

Fei, R., et al., U.S. Pat. No. 5,635,387

Ferrari, G., Cusella-De Angelis, G., Coletta, M., Paolucci, E., Stornaiuolo, A., Cossu, G., and Mavilio, F. (1998). Muscle regeneration by bone marrow-derived myogenic progenitors. *Science* 279:528-30.

Flax, J. D., Sanjay, A., Yang, C., Simonin, C., Wills, A. M., Billinghurst, L. L., Jendoubi, M., Sidman, R. L., Wolfe, J. H., Kim, S. E., and Snyder, E. Y. (1998). Engraftable human NSCs respond to developmental cues replace neurons and express foreign genes. *Nature Biotech* 16:1033-1038.

Fong, G. H., Zhang, L., Bryce, D. M., and Peng, J. (1999). Increased hemangioblast commitment, not vascular disorganization, is the primary defect in flt-1 knock-out mice. *Development.* 126:3015-3025.

Franco Del Arno, F., Gendron-Maguire, M., Swiatek, P. J., and Gridley, T. (1993). Cloning, sequencing and expression pf the mouse mammalian achaete-scute homolog a (MASH I). *Biochem Biophys Acta* 1171:323-7.

Frankel, M. S. (2000). In Search of Stem Cell Policy. *Science* 298:1397.

Fridenshtein, A. (1982). Stromal bone marrow cells and the hematopoietic microenvironment. *Arkh Patol* 44:3-11.

Furcht et al. International Application No. PCT/US00/21387.

Gage, F. H. (2000). Mammalian NSCs. *Science* 287:1433-1438.

Gage, F., Coates, P., Palmer, T., Kuhn, H., Fisher, L., Suhonen, J., Peterson, D., Suhr, S., and Ray, J. (1995). Survival and differentiation of adult neuronal progenitor cells transplanted to the adult brain. *Proc Natl Acad Sci USA* 92:11879-83.

Gehling, U. M., Ergun, S., Schumacher, U., Wagener, C., Pantel, K., Otte, M., Schuch, G., Schafhausen, P., Mende, T., Kilic, N., Kluge, K., Schafer, B., Hossfeld, D. K. and Fiedler, W. (2000). In vitro differentiation of endothelial cells from AC 133-positive progenitor cells. *Blood* 95:3106-3112.

Gritti, A., Frolichsthal-Schoeller, P., Galli, R., Parati, E. A., Cova, L., Pagano, S. F., Bjornson, C. R., and Vescovi, A. L. (1999). Epidermal and fibroblast growth factors behave as mitogenic regulators for a single multipotent stem cell-like population from the subventricular region of the adult mouse forebrain. *J Neurosci.* 19:3287-97.

Gronthos, S., Graves, S., Ohta, S., and Simmons, P. (1994). The STRO-1+ fraction of adult human bone marrow contains the osteogenic precursors. *Blood* 84: 4164-73.

Guenechea, G., Gan, O., Dorrell, C., and Dick, J. E. (2001). Distinct classes of human stem cells that differ in proliferative and self-renewal potential. *Nat J Immunol* 2:75-82.

Gussoni, E., Soneoka, Y., Strickland, C., Buzney, E., Khan, M., Flint, A., Kunkel, L., and Mulligan, R. (1999). Dystrophin expression in the mdx mouse restored by stem cell transplantation. *Nature* 401:390-4.

Hamazaki, T., Iiboshi, Y., Oka, M., Papst, P. J., Meacham, A. M., Zon, L. I., and Terada, N. 2001. Hepatic maturation in differentiating embryonic stem cells in vitro. *FEBS Lett* 497:15-19.

Haralabopoulos, G. C., D. S. Grant, H. K. Kleinman, and M. E. Maragoudakis. (1997). Thrombin promotes endothelial cell alignment in Matrigel in vitro and angiogenesis in vivo. *Am J Physiol.* 273:C239-245.

Hedlund, E., Gustafsson, J. A., and Warner, M. (2001). Cytochrome P450 in the brain; a review. *Curr Drug Metab* 2:245-263.

Hill, B., Rozler, E., Travis, M., Chen, S., Zannetino, A., Simmons, P., Galy, A., Chen, B., Hoffman, R. (1996). High-level expression of a novel epitope of CD59 identifies a subset of CD34+ bone marrow cells highly enriched for pluripotent stem cells. *Exp Hematol.* 8:93643.

Hirashima, M., H. Kataoka, S. Nishikawa, N. Matsuyoshi, and S. Nishikawa. (1999). Maturation of ES cells into endothelial cells in an in vitro model of vasculogenesis. *Blood.* 93:1253-1263.

Holash, J., Maisonpierre, P. C., Compton, D., Boland, P., Alexander, C. R., Zagzag, D., Yancopoulos, G. D., and Wiegand, S. J. (1999). Vessel cooption, regression, and growth in tumors mediated by angiopoietins and VEGF. *Science.* 284:994-998.

Hu, Z., Evarts, R. P., Fujio, K., Marsden, E. R., and Thorgeirsson, S. S. (1993). Expression of hepatocyte growth factor and c-met genes during hepatic differentiation and liver development in the rat. *Am J Pathol.* 142:1823-30.

Iyer, V. R., Eisen, M. B., Ross, D. T., Schuler, G., Moore, T., Lee, J. C. F., Trent, J. M., Staudt, L. M., Hudson, J. J., Boguski, M. S., Lashkari, D., Shalon, D., Boistein, D., and Brown, P. O. (1999). The transcriptional program in the response of human fibroblasts to serum. *Science.* 283:83-87.

Jackson, K., Majka, S. M., Wang, H., Pocius, J., Hartley, C., Majesky, M. W., Entman, M. L., Michael, L., Hirschi, K. K., and M. A., G. (2001). Regeneration of ischemic cardiac muscle and vascular endothelium by adult stem cells. *J Clin Invest* 107:1395-1402.

Jackson, K., Mi, T., and Goodell, M. A. (1999). Hematopoietic potential of stem cells isolated from murine skeletal muscle. *Proc Natl Acad Sci USA* 96:14482-6.

Jaiswal, N., et al., (1997). *J Cell Biochem.* 64(2):295-312.

Jarukamjorn, K., Sakuma, T., Miyaura, J., and Nemoto, N. (1999). Different regulation of the expression of mouse hepatic cytochrome P450 2B enzymes by glucocorticoid and phenobarbital. *Arch Biochem Biophys* 369:89-99.

Jiang, Y. 2002. Submitted.

Johansson, C. B., Momma, S., Clarke, D. L., Risling, M., Lendahl, U., and Frisen, J. (1999). Identification of a NSC in the adult mammalian central nervous system. *Cell.* 96:25-34.

Johnstone, B., Hering, T. M., Caplan, A. I., Goldgberg, V. M., Yoo, J. U. (1998). In vitro chondrogenesis of bone marrow-derived mesenchymal progenitor cells. *Exp Cell Res.* 1:265-72.

Jordan, C. T., and Van Zant, G. (1998). Recent progress in identifying genes regulating HSC function and fate. *Curr Opin Cell Biol.* 10:716-20.

Jordan, C., McKearn, J., and Lemischka, I. (1990). Cellular and developmental properties of fetal HSCs. *Cell* 61:953-963.

Kim, T. H., Mars, W. M., Stolz, D. B., Petersen, B. E., and Michalopoulos, G. K. (1997). Extracellular matrix remodeling at the early stages of liver regeneration in the rat. *Hepatology* 26:896-904.

Kopen, G., D. Prockop, and D. Phinney. 1999. Marrow stromal cells migrate throughout forebrain and cerebellum, and they differentiate into astrocytes after injection into neonatal mouse brains. Proc Natl Acad Sci USA. 96:10711-10716.

Kourembanas, S., Morita, T., Christou, H., Liu, Y., Koike, H., Brodsky, D., Arthur, V., and Mitsial, S. A. (1998). Hypoxic responses of vascular cells. *Chest.* 11 (Suppl 1):25S-28S.

Krause, D. S., Theise, N. D., Collector, M. I., Henegariu, O., Hwang, S., Gardner, R., Neutzel, S., and Sharkis, S. I. (2001). Multi-organ, multi-lineage engraftment by a single bone marrow-derived stem cell. *Cell* 105:369-77.

Lagasse, E., Connors, H., Al-Dhalimy, M., Reitsma, M., Dohse, M., Osborne, L., Wang, X., Finegold, M., Weissman, I. L., and Grompe, M. (2000). Purified hematopoietic stem cells can differentiate into hepatocytes in vivo. *Nat Med.* 6:1229-1234.

Larsson, J., Goumans, M. J., Sjostrand, L. J., van Rooijen, M. A., Ward, D., Leveen, P., Xu, X., ten Dijke, P., Mummery, C. L., and Karlsson, S. (2001). Abnormal angiogenesis but intact hematopoietic potential in TGF-beta type I receptor-deficient mice. *EMBO J.* 20:1663-1673.

Lazar, A., Peshwa, M. V., Wu, F. J., Chi, C. M., Cerra, F. B., and Hu, W. S. (1995). Formation of porcine hepatocyte spheroids for use in a bioartificial liver. *Cell Transplant* 4:259-68.

Lee, S. H., Lumelsky, N., Studer, L., Auerbach, J. M., and McKay, R. D. (2000). Efficient generation of midbrain and hindbrain neurons from mouse ES cells. *Nat Biotechnol* 18:675-9.

Lewis, I. D., Almeida-Porada, G., Du, J., Lemischka, I. R., Moore, K. A., Zanjani, E. D., and Verfaillie, C. M. (2001). Long-term repopulating cord blood stem cells are preserved after ex-vivo culture in a non-contact system. *Blood* 97:441-9.

Li, C. X., and Poznansky, M. J. (1990). Characterization of the ZO-1 protein in endothelial and other cell lines. *J Cell Sci.* 2:231-7. 97:231-237.

Li-Masters, T., and Morgan, E. T. 2001. Effects of bacterial lipopolysaccharide on Phenobarbital-induced CYP2B expression in mice. Drug *Metab Dispos* 29:252-257.

Lin, Y., Weisdorf, D. J., Solovey, A., and Hebbel, R. P. (2000). Origins of circulating endothelial cells and endothelial outgrowth from blood. *J Clin Inves.t* 105:71-7.

Liu, S., Qu, Y., Stewart, T. J., Howard, M. J., Chakrabortty, S., Holekamp, T. F., and McDonald, J. W. (2000). ES cells differentiate into oligodendrocytes and myelinate in culture and after spinal cord transplantation. *Proc Natl Acad Sci USA* 97:6126-31.

Mahley, R. W., and Ji, Z. S. (1999). Remnant lipoprotein metabolism: key pathways involving cell-surface heparan sulfate proteoglycans and apolipoprotein E. *J Lipid Res* 40:1-16.

Martin, G. R. (1981). Isolation of a pluripotent cell line from early mouse embryos cultured in medium conditioned by teratocaracinoma stem cells. *Proc Natl Acad Sci U.S.A.* 12:7634-8.

Masinovsky, B., U.S. Pat. No. 5,837,670

Mathon, N. F., Malcolm, D. S., Harrisingh, M. C., Cheng, L., and Lloyd, A. C. (2001). Lack of Replicative Senescence in Normal Rodent Glia. *Science* 291:872-875.

McGlave, et al., U.S. Pat. No. 5,460,964

Meager, A. (1999). Cytokine regulation of cellular adhesion molecule expression in inflammation. *Cytokine Growth Factor Rev.* 10:27-39.

Medvinsky, A., and Dzierzak, E. (1996). Definitive hematopoiesis is autonomously initiated by the AGM region. *Cell.* 86:897.

Melton, D. (1997). Signals for tissue induction and organ formation in vertebrate embryos. *Harvey Lect* 93:49-64.

Mezey, E., Chandross, K. J., Harta, G., Maki, R. A., and McKercher, S. R. (2000). Turning Blood into Brain: Cells Bearing Neuronal Antigens Generated in vivo from Bone Marrow. *Science* 290:1779-1782.

Miyajima, A., Kinoshita, T., Tanaka, M., Kamiya, A., Mukouyama, Y., arid Hara, T. (2000). Role of Oncostatin M in hematopoiesis and liver development. *Cytokine Growth Factor Rev* 11:177-183.

Morrison, S. J., White, P. M., Zock, C., and Anderson, D. J. (1999). Prospective identification isolation by flow cytometry and in vivo self-renewal of multipotent mammalian neural crest stem cells. *Cell.* 96:737-749.

Nichols, J., Zevnik, B., Anastassiadis, K., Niwa, H., Klewe-Nebenius, D., Chambers, I., Scholer, H., and Smith, A. (1998). Formation of pluripotent stem cells in the mammalian embryo depends on the POU transcription factor Oct 4. *Cell* 95:379-91.

Nishikawa, S., Nishikawa, S., Hirashima, M., Matsuyoshi, N., and Kodama, H. (1998). Progressive lineage analysis by cell sorting and culture identifies FLKI+VEcadherin+ cells at a diverging point of endothelial and hemopoietic lineages. *Development.* 125:1747-1757.

Nishikawa, S. I., Nishikawa, S., Kawamoto, H., Yoshida, H., Kizumoto, M., Kataoka, H. and Katsura, Y. (1998). In vitro generation of lymphohematopoietic cells from endothelial cells purified from murine embryos. *Immunity.* 8:761-769.

Niwa, H., Miyazaki, J., and Smith, A. G. (2000). Quantitative expression of Oct-3/4 defines differentiation, dedifferentiation or self-renewal of ES cells. *Nat Genet* 24:372-6.

Nolta, J., Dao, M., Wells, S., Smogorzewska, E., and Kohn, D. (1996). Transduction of pluripotent human HSCs demonstrated by clonal analysis after engraftment in immune-deficient mice. *Proc Natl Acad Sci USA* 93:2414-9.

Odorico, J. S., Kaufman, D. S., and Thomson, J. A. (2001). Multilineage differentiation from human ES cell lines. *Stem Cells* 19:193-204.

Oh, S. H., Miyazaki, M., Kouchi, H., Inoue, Y., Sakaguchi, M., Tsuji, T., Shima, N., Higashio, K., and Namba, M. (2000). Hepatocyte growth factor induces differentiation of adult rat bone marrow cells into a hepatocyte lineage in vitro. *Biochem Biophys Res Commun* 279:500-504.

Okabe, S., Forsberg-Nilsson, K., Spiro, A. C., Segal, M., and McKay, R. D. (1996). Development of neuronal precursor cells and functional postmitotic neurons from ES cells in vitro. *Mech Dev* 59:89-102.

O'Leary, D. D., and Wilkinson, D. G. (1999). Eph receptors and ephrins in neural development. *Cuff Opin Neurobiol* 9:65-73.

Orkin, S. (1998). Embryonic stem cells and transgenic mice in the study of hematopoiesis. *Int. J. Dev. Biol.* 42:927-34.

Orlic, D., Kajstura, J., Chimenti, S., Jakoniuk, I., Anderson, S. M., Li, B., Pickel, J., McKay, R., Nadal-Ginard, B., Bodine, D. M., Leri, A., and Anversa, P. (2001). Bone marrow cells regenerate infarcted myocardium. *Nature* 410:701-5.

O'Shea, K. (1999). ES cell models of development. *Anat Rec* 15:3241.

Palmer, T. D., Markakis, E. A., Willhoite, A. R., Safar, F., and Gage, F. H. (1999). Fibroblast growth factor-2 activates a latent neurogenic program in NSCs from diverse regions of the adult CNS. *J Neurosci* 19:8487-97.

Palmer, T. D., Takahashi, J., and Gage, F. H. (1997). The adult rat hippocampus contains primordial NSCs. *Mol Cell Neurosci* 8:389-404.

Partanen, J., and D. J. Dumont. (1999). Functions of Tie 1 and Tie2 receptor tyrosine kinases in vascular development. *Curr Top Microbiol Immunol.* 237:159-172.

Peault, B. 1996. Hematopoiedc stem cell emergence in embryonic life: developmental hematology revisited. J. *Hematother.* 5:369.

Peichev, M., Naiyer, A. J., Pereira, D., Zhu, Z., Lane, W. J., Williams, M., Oz, M. C., Hicklin, D. J., Witte, L., Moore, M. A., and Rafii, S. (2000). Expression of VEGFR 2 and AC133 by circulating human CD34(+) cells identifies a population of functional endothelial precursors. *Blood* 95:952-958.

Peshwa M V, WU F J, Follstad B D, Cerra, F. B., and Hu, W. S. 1994. Kinetics of hepatocyte spheroid formation. *Biotechnology Progress* 10:460-466.

Petersen, B. E., Bowen, W. C., Patrene, K. D., Mars, W. M., Sullivan, A. K., Murase, N., Boggs, S. S., Greenberger, J. S., and Goff, J. P. (1999). Bone marrow as a potential source of hepatic oval cells. *Science* 284:1168-1170.

Petersen, B. E. 2001. Hepatic "stem" cells: coming full circle. *Blood Cells Mol Dis* 27:590-600.

Petersen, B. E., Bowen, W. C., Patrene, K. D., Mars, W. M., Sullivan, A. K., Murase, N., Boggs, S. S., Greenberger, J. S., and Goff, J. P. 1999. Bone marrow as a potential source of hepatic oval cells. Science 284:1168-1170.

Petzelbauer, P., Halama, T., and Groger, M. (2000). Endothelial adherens junctions. *JInvestig Dermatol Symp Proc.* 5:10-13.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human MSCs. *Science* 284:143-147.

Pittenger, M., U.S. Pat. No. 5,827,740

Ploemacher, R. E., and Brons, N. H. (1988). Isolation of hemopoietic stem cell subsets from murine bone marrow: 1. Radioprotective ability of purified cell suspensions differing in the proportion of day-7 and day-12 CFU-S. *Exp Hematol* 16:21-6.

Potten, C. (1998). Stem cells in gastrointestinal epithelium: numbers, characteristics and death. *Philos Trans R Soc Lond B Biol Sci* 353:821-30.

Prochazka, M., H. R. Gaskins, L. D. Shultz, and E. H. Leiter. (1992). The nonobese diabetic scid mouse: model for spontaneous thymomagenesis associated with immunodeficiency. *Proc Natl Acad Sci USA.* 89:3290-3294.

Rader, D. J., and Dugi, K. A. (2000). The endothelium and lipoproteins: insights from recent cell biology and animal studies. *Semin Thromb Hemost* 26:521-528.

Rafii, S., F. Shapiro, J. Rimarachin, R. Nachman, B. Ferris, B. Weksler, M. Moore, arid A. Asch. (1994). Isolation and characterization of human bone marrow microvascular endothelial cells: hematopoietic progenitor cell adhesion. *Blood.* 84:10-20.

Rafii, S., Shapiro, F., Pettengell, R., Ferris, B., Nachman, R., Moore, M., and Asch, A. (1995). Human bone marrow microvascular endothelial cells support long-term proliferation and differentiation of myeloid and megakaryocytic progenitors. *Blood* 86:3353-61.

Reinhardt, R. L., Kboruts, A., Merica, R., Zell, T., and Jenkins, M. K. (2001). Visualizing the generation of memory CD4 T cells in the whole body. *Nature* 401:101-105.

Reubinoff, B. E., Pera, M. F., Fong, C. Y., Trounson, A., and Bongso, A. (2000). ES cell lines from human blastocysts: somatic differentiation in vitro. *Nat Biotech* 18:399404.

Reyes, M., and Verfaillie, C. M. (2001). Characterization of multipotent adult progenitor cells, a subpopulation of mesenchymal stem cells. *Ann NY Acad Sci* 938:231-233; discussion 233-235.

Reyes, M., Lund, T., Lenvik, T., Aguiar, D., Koodie, L., and Verfaillie, C. M. (2001). Purification and ex vivo expansion of postnatal human marrow mesodermal progenitor cells. *Blood.* 98:2615-2625.

Reynolds, B., and Weiss, S. (1992). Generation of neurons and astrocytes from isolated cells of the adult mammalian central nervous system. *Science* 255:1707-10.

Reynolds, B., and Weiss, S. (1996). Clonal and population analyses demonstrate that an EGF-responsive mammalian embryonic CNS precursor is a stem cell. *Dev Biol* 175:1-13

Ribatti, D., A. Vacca, B. Nico, L. Roncali, and F. Dammacco. (2001). Postnatal vasculogenesis. *Mech Dev.* 100:157-163.

Richards, L. J., Kilpatrick, T. J., and Bartlett, P. F. (1992). De novo generation of neuronal cells from the adult mouse brain. *Proc Natl Acad Sci USA.* 89:8591-5.

Rideout, W. M., 3rd, Wakayama, T., Wutz, A., Eggan, K., Jackson-Grusby, L., Dausman, J., Yanagimachi, R., and Jaenisch, R. (2000). Generation of mice from wild-type and targeted ES cells by nuclear cloning. *Nat Genet* 24:109-10.

Robertson, S. M., Kennedy, M., Shannon, J. M., Keller, G. (2000). A transitional stage in the commitment of mesoderm to hematopoiesis requiring the transcription factor SCL/tal-1. *Development.* 11:2447-59.

Rosenberg, J. B., P. A. Foster, R. J. Kaufman, E. A. Vokac, M. Moussalli, P. A. Kroner, and R. R. Montgomery. (1998). Intracellular trafficking of factor VIII to von Willebrand factor storage granules. *J Clin Invest.* 101:613-624.

Rozga, J., Arnaout, W. S., and Demetriou, A. A. (2001). Isolation, characterization, -derived hepatocyte stem cells. *Biochem Biophys Res Commun* 288:156-164.

Ryder, E. F., Snyder, E. Y., and Cepko, C. L. (1990). Establishment and characterization of multipotent neural cell lines using retrovirus vector-mediated oncogene transfer. *J Neurobiol* 21:356-375.

Sah, D. W., Ray, J., and Gage, F. H. (1997). Regulation of voltage- and ligand-gated currents in rat hippocampal progenitor cells in vitro. *J Neurobiol* 32:95-110.

Sanchez-Ramos, J., Song, S., Cardozo-Pelaez, F., Hazzi, C., Stedeford, T., Willing, A., Freeman, T. B., Saporta, S., Janssen, W., Patel, N., Cooper, D. R., and Sanberg, P. R. (2000). Adult bone marrow stromal cells differentiate into neural cells in vitro. *Exp Neurol.* 164:247-56.

Saucedo-Cardenas, O., Quintana-Hau, J. D., Le, W. D., Smidt, M. P., Cox, J. J., De Mayo, F., Burbach, J. P., and Conneely, 0. M. (1998). Nurrl is essential for the induction of the dopaminergic phenotype and the survival of ventral mesencephalic late dopaminergic precursor neurons. *Proc Natl Acad Sci USA* 95: 4013-8.

Scherf, U., D. T. Ross, M. Waltham, L. H. Smith, J. K. Lee, L. Tanabe, K. W. Kohn, W. C. Reinhold, T. G. Myers, D. T. Andrews, D. A. Scudiero, M. B. Eisen, E. A. Sausville, Y.

Pommier, D. Botstein, P. O. Brown, and J. N. Weinstein. (2000). A gene expression database for the molecular pharmacology of cancer. *Nat Biotech.* 24:236-244.

Scholer, H. R., Hatzopoulos, A. K., Balling, R., Suzuki, N., and Gruss, P. (1989). A family of octamer-specific proteins present during mouse embryogenesis: evidence for germ-line-specific expression of an Oct factor. *EMBO J.* 8.2543-50.

Schuldiner, M., Yanuka, O., Itskovitz-Eldor, J., Melton, D. A., and Benvenisty, N. (2000). From the cover: effects of eight growth factors on the differentiation of cells derived from human ES cells. *Proc Natl Acad Sci USA* 97:11307-12.

Schwartz, et al., U.S. Pat. No. 759,793

Seglen, P. O. (1976). Preparation of isolated rat liver cells. *Methods Cell Biol* 13:29-83.

Shamblott, M., Axelman, J., Wang, S., Bugg, E., Littlefield, J., Donovan, P., Blumenthal, P., Huggins, G., Gearhart, J.: (1998) Derivation of pluripotent stem cells from cultured human primordial germ cells. *Proc. Natl. Acad. Sci. U.S.A.* 95:13726-31.

Shen, C. N., Slack, J. M., and Tosh, D. (2000). Molecular basis of transdifferentiation of pancreas to liver. *Nat Cell Biol.* 2:879-887.

Shi, Q., S. Rafii, M. Hong-De Wu, E. S. Wijelath, C. Yu, A. Ishida, Y. Fujita, S. Kothari, R. Mohle, L. R. Sauvage, M. A. S. Moore, R. F. Storb, and W. P. Hammond. (1998). Evidence for circulating bone marrow-derived endothelial cells. *Blood* 92:362-367.

Shih, C. C., Y. Weng, A. Mamelak, T. LeBon, M. C. Hu, and S. Forman. (2001). Identification of a candidate human neurohematopoietic stem-cell population. *Blood* 98:2412-2422.

Simeone, A. (1998). Otx1 and Otx2 in the development and evolution of the mammalian brain. *EMBO* 117:6790-8.

Simmons, P., et al., U.S. Pat. No. 5,677,136

Soule H D, et al. (1973) A human cell line from a pleural effusion derived from a breast carcinoma. J Natl Cancer Inst; 51(5):1409-16.

Southern, P. J., Blount, P., and Oldstone, M. B. (1984). Analysis of persistent virus infections by in situ hybridization to whole-mouse sections. *Nature* 312:555-8.

Steeber, D. A., and T. Tedder, F. (2001). Adhesion molecule cascades direct lymphocyte recirculation and leukocyte migration during inflammation. *Immunol Res.* 22:299-317.

Steinberg, D., Pittman, R. C. and Carew, T. E. (1985). Mechanisms involved in the uptake and degradation of low density lipoprotein by the artery wall in vivo. *Ann NY Acad Sci.* 454:195-206.

Studer, L., Spenger, C., Seiler, R., Othberg, A., Lindvall, O., and Odin, P. (1996). Effects of brain-derived neurotrophic factor on neuronal structure of dopaminergic neurons in dissociated cultures of human fetal mesencephalon. *Exp Brain Res* 108:328-36.

Suhonen, J., Peterson, D., Ray, J., and Gage, F. (1996). Differentiation of adult hippocampus-derived progenitors into olfactory neurons in vivo. *Nature* 383:624-7.

Svendsen, C. N., and Caldwell, M. A. (2000). NSCs in the developing central nervous system: implications for cell therapy through transplantation. *Prog Brain Res.* 127:13-34.

Svendsen, C. N., Caldwell, M. A., Ostenfeld, T. (1999). Human neural stem cells: Isolation, expansion and transplantation. *Brain Path* 9:499-513.

Tang, D. G., Tokumoto, Y. M., Apperly, J. A., Lloyd, A. C., and Raff, M. C. (2001). Lack of replicative senescence in cultured rat oligodendrocyte precursor cells. Science 291: 868-71.

Tedder, T., Steeber, D., Chen, A., and Engel, P. (1995). The selections: vascular adhesion molecules. *FASEB J.* 9:866.

Theise, N. D., Badve, S., Saxena, R., Henegariu, O., Sell, S., Crawford, J. M., and Krause, D. S. (2000). Derivation of hepatocytes from bone marrow cells in mice after radiation-induced myeloablation. *Hepatology* 31:23540.

Theise, N. D., Saxena, R., Portmann, B. C., Thung, S. N., Yee, H., Chiriboga, L., Kumar, A., and Crawford, J. M. (1999). The canals of Hering and hepatic stem cells in humans. *Hepatology* 30:1425-1433.

Thomson, J. A., Itskovitz-Eldor, J., Shapiro, S. S., Waknitz, M. A., Swiergiel, J. J., Marshall, V. S., and Jones, J. M. (1998). ES cell lines derived from human blastocysts. *Science* 282:114-7.

Thomson, J., Kalisman J., Golos, J., Durning, M., Harris, C., Becker, R., Hearn, J. (1995) Isolation of a primate embryonic stem cell line. *Proc. Natl. Acad. Sci. USA.* 92:7844-8, Trupp, M., Arenas, E., Fainzilber, M., Nilsson, A. S., Sieber, B. A., Grigoriou, M., Kilkenny, C., Salazar-Grueso, E., Pachnis, V., and Arumae, U. (1996). Functional receptor for GDNF encoded by the c-ret proto-oncogene. *Nature* 381:785-9.

Tsai, R. Y. and McKay, R. D. (2000). Cell contact regulates fate choice by cortical stem cells. *J. Neurosci.* 20:3725-35.

Tsukamoto, et al., U.S. Pat. No. 5,750,397

Tsukamoto, et al., U.S. Pat. No. 5,716,827

Tzanakakis, E. S., Hansen, L. K., and Hu, W. S. (2001). The role of actin filaments and microtubules in hepatocyte spheroid self-assembly. *Cell Motil Cytoskeleton* 48:175-189.

Tzanakakis, E. S., Hsiao, C. C., Matsushita, T., Remmel, R. P., and Hu, W. S. (2001). Probing enhanced cytochrome P450 2B1/2 activity in rat hepatocyte spheroids through confocal laser scanning microscopy. *Cell Transplant.* 10:329342.

Uchida, N., Buck, D. W., He, D., Reitsma, M. J., Masek, M., Phan, T. V., Tsukamoto, A. S., Gage, F. H., and Weissman, I. L. (2000). Direct isolation of human central nervous system stem cells. *Proc Natl Acad Sci USA.* 97:14720-14725.

Van Rijen, H., van Kempen, M. J., Analbers, L. J., Rook, M. B., van Ginneken, A. C., Gros, D., and Jongsma, H. J. (1997). Gap junctions in human umbilical cord endothelial cells contain multiple connexins. *Am J Physiol.* 272:C117-130.

Verfaillie, C., Miller, W., Boylan, K., McGlave, P. (1992). Selection of benign primitive hematopoietic progenitors in chronic myelogenous leukemia on the basis of HLA-DR antigen expression. *Blood.* 79:1003-1010.

Vescovi, A. L., Paraati, E. A., Gritti, A., Poulin, P., Ferrario, M., Wanke, E., Frolichsthal-Schoeller, P., Cova, L., Arcellana-Panlilio, M., Colombo, A., and Galli, R. (1999). Isolation and cloning of multipotential stem cells from the embryonic human CNS and establishment of transplantable human NSC lines by epigenetic stimulation. *Exp Neurol* 156:71-83.

Vescovi, A., Reynolds, B., Fraser, D., and Weiss, S. (1993). bFGF regulates the proliferative fate of unipotent (neuronal) and bipotent (neuronal/astroglial) EGF-generated CNS progenitor cells. *Neuron* 11: 951-66.

Vischer, U. M., H. Barth, and C. B. Wollheim. (2000). Regulated von Willebrand factor secretion is associated with agonist-specific patterns of cytoskeletal remodeling in cultured endothelial cells. *Arterioscler Thromb Vasc Biol.* 20:883-891.

Wagner, D. D., Olmsted, J. B., and Marder, V. J. (1982). Immunolocalization of von Willebrand protein in Weibel-Palade bodies of human endothelial cells. *J. Cell Biol.* 95:355-360.

Wagner, J., Akerud, P., Castro, D. S., Holm, P. C., Canals, J. M., Snyder, E. Y., Perlmann, T., and Arenas, E. (1999). Induction of a midbrain dopaminergic phenotype in Nurrl-overexpressing NSCs by type I astrocytes. *Nat Biotech* 17:653-9.

Wakitani, S., Saito, T., and Caplan, A. (1995). Myogenic cells derived from rat bone marrow MSCs exposed to 5-azacytidine. *Muscle Nerve* 18:1417-26.

Wang, X., AI-Dhalimy, M., Lagasse, E., Finegold, M., and Grompe, M. (2001). Liver repopulation and correction of metabolic liver disease by transplanted adult mouse pancreatic cells. *Am J Pathol* 158:571-579.

Watt, F. (1997). Epidermal stem cells: markers patterning and the control of stem cell fate. *Philos Trans R Soc Lond B Biol Sci* 353: 831-6.

Watt, S., Gschmeissner, S., and Bates, P. (1995). PECAM-1: its expression and function as a cell adhesion molecule on hemopoietic and endothelial cells. *Leuk Lymph.* 17:229.

Weiss, M. J., Orkin, S. H. (1995) GATA transcription factors: key regulators of hematopoiesis. *Exp Hematol.* 2:99-107.

Weissman, I. L. (2000). Translating stem and progenitor cell biology to the clinic: barriers and opportunities. *Science* 287:1442-6.

Wells, J. M., and Melton, D. A. (2000). Early mouse endoderm is patterned by soluble factors from adjacent germ layers. *Development.* 127:1563-72.

Wells, J. M., and Melton, D. A. (1999). Vertebrate endoderm development. *Annu Rev Cell Dev Biol* 15:393-410.

Whittemore, S. R., Morassutti, D. J., Walters, W. M., Liu, R. H., and Magnuson, D. S. (1999). Mitogen and substrate differentially affect the lineage restriction of adult rat subventricular zone neural precursor cell populations. *Exp Cell Res* 252:75-95.

Williams, R. L., Hilton, D. J., Pease, S., Willson, T. A., Stewart, C. If, Gearing, D. P., Wagner, E. F., Metcalf, D., Nicola, N. A., and Gough, N. M. (1988). Myeloid leukemia inhibitory factor maintains the developmental potential of ES cells. *Nature* 336:684-7.

Wilmut, I., Schnieke, A. E., McWhir, J., Kind, A. J., and Campbell, K. H. (1997). Viable offspring derived from fetal and adult mammalian cells. *Nature* 385:810-3.

Woodbury, D., Schwarz, E. J., Prockop, D. J., and Black, I. B. (2000). Adult rat and human bone marrow stromal cells differentiate into neurons. *J Neurosci Res* 15:364-70.

Yamashita, J., Itoh, H., Hirashima, M., Ogawa, M., Nishikawa, S., Yurugi, T., Naito, M., Nakao, K., and Nishikawa, S. (2000). Flk1-positive cells derived from ES cells serve as vascular progenitors. *Nature.* 408:92-96.

Yang, J., Nagavarapu, U., Relloma, K., Sjaastad, M. D., Moss, W. C., Passaniti, A., and Herron, G. S. (2001). Telomerized human microvasculature is functional in viva. *Nat Biotechnol.* 19:219-224.

Ye, W., Shimamura, K., Rubenstein, J., Hynes, M., and Rosenthal, A. (1998). FGF and Shh signals control dopaminergic and serotonergic cell fate in the anterior neural plate. *Cell* 93:755-66.

Yoneya, T., Tahara, T., Nagao, K., Yamada, Y., Yamamoto, T., Osawa, M., Miyatani, S., and Nishikawa, M. (2001). Molecular cloning of delta-4, a new mouse and human Notch ligand. *J Biochem.* 129:27-34.

Yoo, J. U., Barthel, T. S., Nishimura, K., Solchaga, L., Caplan, A. I., Goldberg, V. M., Johnstone, B. (1998). Then chondrogenic potential of human bone-marrow-derived mesenchymal progenitor cells. *J Bone Joint Surg Am.* 12:1745-57.

Young, H., et al., U.S. Pat. No. 5,827,735

Zambrowicz, B. P., Imamoto, A., Hering, S., Herzenberg, L. A., Kerr, W. G., and Soriano, P. (1997). Disruption of overlapping transcripts in the ROSA beta geo 26 gene trap strain leads to widespread expression of beta-galactosidase in mouse embryos and hematopoietic cells. *Proc Natl Acad Sci USA.* 94:3789-94.

Zaret, K. S. (2000). Liver specification and early morphogenesis. *Mech Dev* 92:83-88.

Zaret, K. S. (2001). Hepatocyte differentiation: from the endoderm and beyond. *Curr Opin Genet Dev.* 11:568-574.

Zelko, I., and Negishi, M. (2000). Phenobarbital-elicited activation of nuclear receptor CAR in induction of cytochrome P450 genes. *Biochem Biophys Res Commun.* 277:1-6.

Zhao, R. C. H., Jiang, Y., and Verfaillie, C. M. (2000). A model of human p210BCW"BL mediated CML by transducing primary normal human CD34+ cells with a BCR/ABL containing retroviral vector. *Blood* 97:2406-12.

Ziegler, B., M. Valtieri, G. Porada, R. De Maria, R. Muller, B. Masella, M. Gabbianelli, 1. Casella, E. Pelosi, T. Bock, E. Zanjani, and C. Peschle. (1999). KDR Receptor: A Key Marker Defining HSCs. *Science.* 285:1553 1558.

What is claimed is:

1. A method for identifying an agent that is a differentiation factor, the method comprising:
   (a) contacting (1) a desired agent with (2) isolated expanded human multipotent, non-embryonic, non-germ, cells that can differentiate into at least one cell type of each of the endodermal, ectodermal and mesodermal embryonic lineages and express telomerase; and
   (b) determining whether the agent of step (a) affects differentiation of the telomerase-expressing cells into a desired differentiated progeny, where affecting differentiation indicates an agent that is a differentiation factor, wherein the telomerase-expressing cells have undergone at least 10-40 cell doublings in culture.

2. The method of claim 1 wherein the telomerase-expressing cells express oct3/4.

3. The method of claim 1, wherein differentiation is into an endodermal cell type.

4. The method of claim 1, wherein differentiation is into a mesodermal cell type.

5. The method of claim 1, wherein differentiation is into an ectodermal cell type.

6. The method of claim 1, wherein the telomerase-expressing cells have undergone greater than 40 cell doublings.

7. The method of claim 1, wherein the effect on differentiation is assayed by changes in protein expression, RNA expression, or morphology.

* * * * *